US007148021B2

(12) United States Patent
Chi et al.

(10) Patent No.: US 7,148,021 B2
(45) Date of Patent: Dec. 12, 2006

(54) HUMAN ZONA PELLUCIDA PROTEINS AND METHODS OF THEIR USE IN DIAGNOSING MALE INFERTILITY

(75) Inventors: Ting-Fung Chi, Yorktown, VA (US); Zhiyong Lin, Norfolk, VA (US); Ke-Wen Dong, Chesapeake, VA (US); Ming-I Hsu, Virginia Beach, VA (US); Jr-Gang Cheng, Virginia Beach, VA (US); Heming Zheng, Norfolk, VA (US); Sergio C. Oehninger, Norfolk, VA (US); William E. Gibbons, Norfolk, VA (US)

(73) Assignees: Eastern Virginia Meical School, Norfolk, VA (US); Trinity Biomedical Technology Corporation, Norfolk, VA (US)

( * ) Notice: Subject to any disclaimer, the term of this patent is extended or adjusted under 35 U.S.C. 154(b) by 47 days.

(21) Appl. No.: 10/209,664

(22) Filed: Aug. 1, 2002

(65) Prior Publication Data

US 2003/0148930 A1 Aug. 7, 2003

Related U.S. Application Data

(60) Provisional application No. 60/339,632, filed on Dec. 11, 2001, provisional application No. 60/309,532, filed on Aug. 2, 2001, provisional application No. 60/309,553, filed on Aug. 2, 2001, provisional application No. 60/309,664, filed on Aug. 2, 2001.

(51) Int. Cl.
*G01N 33/53* (2006.01)
(52) U.S. Cl. .............................. 435/7.1; 514/8; 530/350
(58) Field of Classification Search ................ 435/7.1, 435/69.1, 7.5; 530/350; 514/2, 8; 424/9.1
See application file for complete search history.

(56) References Cited

U.S. PATENT DOCUMENTS

| | | | |
|---|---|---|---|
| 4,399,216 A | 8/1983 | Axel et al. | |
| 4,444,879 A | 4/1984 | Foster et al. | |
| 4,554,101 A | 11/1985 | Hopp | |
| 4,634,665 A | 1/1987 | Axel et al. | |
| 4,861,718 A | 8/1989 | Hirata et al. | |
| 4,889,803 A | 12/1989 | Revel et al. | |
| 4,960,704 A | 10/1990 | Ingolia et al. | |
| 5,034,322 A | 7/1991 | Rogers et al. | |
| 5,179,017 A | 1/1993 | Axel et al. | |
| 5,272,071 A | 12/1993 | Chappel | |
| 5,352,605 A | 10/1994 | Fraley et al. | |
| 5,618,698 A | 4/1997 | Lin | |
| 5,626,846 A * | 5/1997 | Dean ........................ | 424/184.1 |
| 5,641,487 A | 6/1997 | Dean | |
| 5,641,670 A | 6/1997 | Treco et al. | |
| 5,650,321 A | 7/1997 | Levy | |
| 5,672,488 A * | 9/1997 | Dean ........................ | 435/69.3 |
| 5,703,057 A | 12/1997 | Johnston et al. | |
| 5,710,038 A | 1/1998 | Mes-Masson et al. | |
| 5,766,924 A | 6/1998 | Levy | |
| 5,817,793 A | 10/1998 | Levy | |
| 5,821,350 A | 10/1998 | Huang et al. | |
| 5,837,497 A | 11/1998 | Harris | |
| 5,851,763 A | 12/1998 | Heym et al. | |
| 5,851,796 A | 12/1998 | Schatz | |
| 5,851,817 A | 12/1998 | Hardy et al. | |
| 5,869,053 A | 2/1999 | Stern et al. | |
| 5,888,981 A | 3/1999 | Bujard et al. | |
| 5,891,718 A | 4/1999 | Hobart et al. | |
| 5,916,768 A | 6/1999 | Dean | |
| 5,922,927 A | 7/1999 | Bujard et al. | |
| 5,925,541 A | 7/1999 | Goldstein et al. | |
| 5,962,326 A | 10/1999 | Shimada et al. | |
| 5,968,773 A | 10/1999 | Heddle et al. | |
| 5,976,545 A * | 11/1999 | Harris et al. ............. | 424/192.1 |
| 5,981,228 A | 11/1999 | Harris et al. | |
| 5,989,550 A | 11/1999 | Harris et al. | |

(Continued)

FOREIGN PATENT DOCUMENTS

EP 0488470 5/1997

(Continued)

OTHER PUBLICATIONS

Bercegeay S, Jean M, Lucas H, Barriere P. Composition of human zona pellucida as revealed by SDS-PAGE after silver staining.Mol Reprod Dev. Jul. 1995;41(3):355-9.*

(Continued)

*Primary Examiner*—Jon Weber
*Assistant Examiner*—Robert B. Mondesi
(74) *Attorney, Agent, or Firm*—Wilmer Cutler Pickering Hale and Dorr LLP

(57) ABSTRACT

Reagents, methods, and kits are described that are useful for fertility testing and that in many cases provides much faster, convenient and rapid determination of male infertility. The reagents described include properly glycosylated human ZP3, ZP2, ZP1, glycosylated peptides thereof, fusion proteins such as green fluorescent protein—ZP3, non-covalent complexes of ZP2 with ZP3, fusion protein of ZP2–ZP3, solid phase materials such as agarose beads coated with binding agents such as ZP3, and other artificial zona. Methods are provided that, in many cases convert a complex biological event into a well defined biochemical binding event based on one or more of the reagents. Such methods are much easier to set up and monitor, allowing more convenient and inexpensive diagnostic testing for male fertility. The acrosome reaction is detected in other embodiments by virtue of quantitating one or more released substances. Kits are further provided that contain one or more reagents useful for testing at a diagnostic laboratory or other facility.

19 Claims, 5 Drawing Sheets

U.S. PATENT DOCUMENTS

| | | | |
|---|---|---|---|
| 6,001,599 | A | 12/1999 | Harris et al. |
| 6,027,727 | A | 2/2000 | Harris et al. |
| 6,132,952 | A | 10/2000 | Cohen et al. |
| 6,264,953 | B1 | 7/2001 | Dunbar |
| 2002/0028470 | A1 | 3/2002 | Dong et al. |
| 2002/0172982 | A1 | 11/2002 | Dong et al. |

FOREIGN PATENT DOCUMENTS

| | | |
|---|---|---|
| WO | 90/15624 | 12/1990 |
| WO | 92/03548 | 3/1992 |
| WO | WO 92/03548 | 3/1992 |
| WO | 93/14786 | 8/1993 |
| WO | 94/10304 | 5/1994 |
| WO | 94/11019 | 5/1994 |
| WO | WO 94/11019 | 5/1994 |
| WO | 94/22472 | 10/1994 |
| WO | 95/27206 | 10/1995 |
| WO | 96/05305 | 2/1996 |
| WO | 96/06113 | 2/1996 |
| WO | 98/37185 | 8/1998 |
| WO | 99/34825 | 7/1999 |
| WO | 99/42581 | 8/1999 |
| WO | WO 99/42581 | 8/1999 |
| WO | 99/52544 | 10/1999 |
| WO | 99/64626 | 12/1999 |
| WO | 99/64627 | 12/1999 |
| WO | 99/65520 | 12/1999 |
| WO | 99/65928 | 12/1999 |

OTHER PUBLICATIONS

Moos J, Faundes D, Kopf GS, Schultz RM. Composition of the human zona pellucida and modifications following fertilization. Hum Reprod. Sep. 1995;10(9):2467-71.*

Barratt, C.L.R. et al, "Glycosylation of human recombinant ZP3 is necessary to induce the human acrosome reaction", Human Reproduction, Aug. 1994, Abstract No. 033, Vol. 9, Supp. 4, p. 20.

Christopher L.R. Barratt, et al., "Induction of the human acrosome reaction by rhuZP3", Human sperm acrosome reaction, Eds P. Fénichel, J. Parinaud, Colloque INSERM/John Libbey Eurotext Ltd., 1995, vol. 236, p. 105-122.

Stephen J. Beebe, et al., "Recombinant Mouse ZP3 Inhibits Sperm Binding and Induces the Acrosome Reaction", Developmental Biology, 1992, vol. 151, pp. 48-54.

Jeffrey D. Bleil et al., "Mammalian Sperm-Egg Interaction: Identification of a Glycoprotein in Mouse Egg Zonae Pellucidae Possessing Receptor Activity for Sperm", Cell, Jul. 1980, vol. 20, p. 873-882.

I.A. Brewis et al., "Recombinant human zona pellucida glycoprotein 3 induces calcium influx and acrosome reaction in human spermatozoa", Molecular. Human Reproduction, 1996, vol. 2, No. 8, pp. 583-589.

Lani J. Burkman, Ph.D., et al., The hemizona assay (HZA): development of a diagnostic test for the binding of human spermatozoa to the human hemizona pellucida to predict fertilization potential*†‡.

D.J. Burks et al., "Interaction of a Tyrosine Kinase from Human Sperm with the Zona Pellucida at Fertilization", Science, Jul. 7, 1995, vol. 269, pp. 83-86.

Margaret E. Chamberlin et al. "Human homology of the mouse sperm receptor", Proc. Natl. Acad. Sci. USA, Aug. 1990, vol. 87, pp. 6014-6018.

Neil R. Chapman, et al., "The role of carbohydrate in sperm-ZP3 adhesion", Molecular Human Reproduction, 1996, vol. 2, No. 10, pp. 767-774.

Neil R. Chapman et al., "Sperm-zona interaction and recombinant DNA technology", Molecular Human Reproduction, 1997, vol. 3, No. 8, pp. 646-650.

John M. Chirgwin, et al., "Isolation of Biologically Active Ribonucleic Acid from Sources Enriched in Ribonuclease", Biochemistry, 1979, vol. 18, No. 24, pp. 5294-5299.

Nicholas L. Cross et al., "Two Simple Methods for Detecting Acrosome-Reacted Human Sperm", Gamete Research, 1986, vol. 15, pp. 213-226.

Ke Wen Dong et al., Charcterization of the biologic activities of a recombinant human zona pellucida protein 3 expressed in human ovarian teratocarcinoma (PA-1) cells, Am J Obstet Gynecol, Apr. 2001, pp. 835-844.

B.S. Dunbar, et al., "The Mammalian Zona Pellucida: its Biochemistry, Immunochemistry, Molecular Biology, and Developmental Expression", Reprod. Fertil. Dev., 1994, vol. 6, pp. 331-347.

Bonnie S. Dunbar, et al., "Identification of the Three Major Proteins of Porcine and Rabbit Zona Pellucidae by High Resolution Two-Dimensional Gel Electrophoresis: Comparison with Serum, Follicular Fluid, and Ovarian Cell Proteins", Biology of Reproduction, 1981, vol. 24, pp. 1111-1124.

Harven M. Florman, et al., "O-Linked Oligosaccharides of Mouse Egg ZP3 Account for Its Sperm Receptor Activity", Cell, May 1985, vol. 41, pp. 313-324.

Daniel R. Franken et al., "Inhibition of G protein in human sperm and its influence on acrosome reaction and zona pellucida binding", Fertility and Sterility, Dec. 1996, vol. 66, No. 6, pp. 1009-1011.

Michiko N. Fukuda et al., "Embryonal Lactosaminoglycan. the Structure of Branched Lactosaminoglycans with Novel Disialosyl (Sialyl $\alpha 2 \rightarrow$ 9 Sialyl) Terminals Isolated from PA1 Human Embryonal Carcinoma Cells", The Journal of Biological Chemistry, 1985, vol. 260, No. 11, pp. 6623-6631.

Tatsuhiko Furukawa eta l., "A Heparin Binding Protein Whose Expression Increases during Differentiation of Embryonal Carcinoma Cells to Parietal Endoderm Cells: cDNA Cloning and Sequence Analysis", J. Biochem., 1990, vol. 108, pp. 297-302.

Klaus-Dieter Hinsch et al., "Identification of ouse ZP3 Protein in Mammalian Oocytes with Antisera against Synthetic ZP3 Peptides", Biology of Reproduction, 1994, vol. 51, pp. 193-204.

Ross A. Kinloch eta l., "Genomic Organization and Polypeptide Primary Structure of Zona Pellucida Glycoprotein hZP3, the Hamster Sperm Receptor", Developmental Biology, 1990, vol. 142, pp. 414-421.

R.A. Kinloch et al., Developmental Biology, 1991, vol. 145, pp. 203-204.

Vaughan H. Lee at al., "Identification and Structural Characterization of the 75-kDa Rabbit Zona Pellucida Protein", The Journal of Biological Chemistry, 1993, vol. 268, No. 17, pp. 12412-12417.

Ajit Varki, "Metabolic Radiolabeling of Glycoconjugates", Methods in Enzymology, 1994, vol. 230, No. 2, pp. 16-32.

Li-Fang Liang et al., "Oocyte-Specific Expression of Mouse ZP-2: Developmental Regulation of the Zona Pellucida Genes", Molecular and Cellular Biology, Apr. 1990, vol. 10, No. 4, pp. 1507-1515.

Li-Fang Liang et al., "Conservation of Mammalian Secondary Sperm Receptor Genes Enables the Promoter of the Human Gene to Function in Mouse Oocytes", Developmental Biology, 1993, vol. 156, pp. 399-408.

J.A. Lust et al., Sequence, Expression and Function of an mRNA Encoding a Soluble Form of the Human Interleukin-6 Receptor (sIL-6R).

R.A.J. Mcllhinney et al., "Characterization of the Fibronectin Synthesized by Human Germ Cell Tumors", Cancer Research, Mar. 1983, vol. 43, pp. 1282-1288.

Sergio Oehninger, M.D., et al., "Nature of the inhibitory effect of complex saccharide moieties on the tight binding of human spermatozoa to the human zona pellucida", Fertility and Sterility, Jan. 1991, vol. 55, No. 1, pp. 165-169.

Sergio Oehninger, M.D. et al., "Clinical significance of human sperm-zona pellucida binding", Fertility and Sterility, Jun. 1997, vol. 67, No. 6, pp. 1121-1127.

Sarvamangala V. Prasad, et al., "Evaluating Zona Pellucida Structure and Function Using Antibodies to Rabbit 55 kDa ZP Protein Expressed in Baculovirus Expression System", Molecular Reproduction and Development, 1996, vol. 43, pp. 519-529.

Marice J. Ringuette et al., "Oocytespecific gene expression: Molecular characterization of a cDNA coding for ZP-3, the sperm receptor of the mouse zona pellucida", Proc. Natl. Acad. Sci. USA, Jun. 1986, vol. 83, pp. 431-435.

Patricia M. Salingm, "Mammalian sperm interaction with extracellular matrices of the egg", Oxf. Rev. Reprod. Biol., vol. 11, pp. 339-388.

Patrica M. Saling, "How the Egg Regulates Sperm Function during Gamete Interaction: Facts and Fantasies", Biology of Reproduction, 1991, vol. 44, pp. 246-251.

J. Sambrook et al., "Transfection of Coprecipitates of Calcium Phosphate and DNA", Molecular Cloning, A Laboratory Manual, 2nd ed., 1989, pp. 16.32-16.37.

R.B. Shabanowitz et al., "Characterization of the human zona pellucida from fertilized and unfertilized eggs", J. Reprod. Fert., 1988, vol. 82, pp. 151-161.

T.M. Timmons et al., "Antigens of Mammalian Zona Pellucida", Perspectives in Immunoreproduction Conception and Contraception, 1988, Chapter 16, pp. 242-260.

P. Thillai-Koothan et al., "Cloning, sequencing and oocyte-specific expression of the marmoset sperm receptor protein, ZP3", Zygote.

Marcel Van Duin et al., Recombinant Human Zona Pellucida Protein ZP3 Produced by Chinese Hamster Ovary Cells Induces the Human Sperm Acrosome Reaction and Promotes Sperm-Egg Fusion, Biology of Reproduction, 1994, vol. 51, pp. 607-617.

Ajit Varki, "Biological roles of oligosaccharides: all of the theories are correct", Glycobiology, 1993, vol. 3, No. 2, pp. 97-130.

Paul M. Wassarman, "Zona Pellucida Glycoproteins", Ann. Rev. Biochem., 1988, vol. 57, pp. 415-442.

Paul M. Wassarman, "Profile of a mammalian sperm receptor", Development, 1990, vol. 108, pp. 1-17.

P.M. Wassarman, "Regulation of mammalian fertilization by zona pellucida glycoprotems", J. Reprod. Fert. Suppl., 1990, vol. 42, pp. 79-87.

A.J. Whitmarsh et al., "Biological activity of recombinant human ZP3 produced in vitro: potential for a sperm function test", Molecular Human Reproduction, 1996, vol. 2, No. 12, pp. 911-919.

Latif, R. and P. Graves. 2000. "Techniques in Thyroidology: Fluorescent Probes: Looking Backward and Looking Forward." *Thyroid*. vol. 10, No. 5.

Dong, Ke Wen et al. 2001. "Characterization of the Biologic Activities of a Recombinant Human Zona Pellucida Protein 3 Expressed in Human Ovarian Teratocarcinoma (PA-1) Cells." *Am. J. Obstet. Gynecol.* vol. 184, pp. 835-844.

Zhao, Ming et al. May 2002. "Conserved Furin Cleavage Site Not Essential for Secretion and Integration of ZP3 into the Extracellular Egg Coat of Transgenic Mice." *Molecular and Cellular Biology.* vol. 22, No. 9, pp. 3111-3120.

Mar. 21, 2005. Communication from European Patent Office regarding EP 02753427.0.

Harrison, R. G. May 25-27, 1960. "Proceedings of the Society for the Study of Fertility." *Annual Conference.* London.

Hartmann, John F. et al. Oct. 1972. "Early Contact Interactions Between Mammalian Gametes *In Vitro*: Evidence That the Vitellus Influences Adherence Between Sperm and Zona Pellucida." *Proc. Nat. Acad. Sci. USA.* vol. 69, No. 10, pp. 2767-2769.

O'Farrell, Patrick H. May 25, 1975. "High Resolution Two-Dimensional Electrophoresis of Proteins." *The Journal of Biological Chemistry.* vol. 250, No. 10, pp. 4007-4021.

Russell, Lonnie et al. Jul. 1979. "Morphologic Characteristics of the Chemically Induced Acrosome Reaction in Human Spermatozoa." *Fertility and Sterility.* vol. 32, No. 1, pp. 87-92.

Saling, Patricia M. et al. 1979. "An Ultrastructural Study of Epididymal Mouse Spermatozoa Binding to Zonae Pellucidae in Vitro: Sequential Relationship to the Acrosome Reaction." *J. Exp. Zool.* vol. 209, pp. 229-238.

Bleil, Jeffrey D. and Paul M. Wassarman. 1980. "Structure and Function of the Zona Pellucida: Identification and Characterization of the Proteins of the Mouse Oocyte's Zona Pellucida." *Developmental Biology.* vol. 76, pp. 185-202.

Maggio, Edward T., ed. *Enzyme-Immunoassay.* pp. 186-187.

Hook, Ernest B. Sep. 1981. "Rates of Chromosome Abnormalities at Different Maternal Ages." *Obstetrics and Gynecology.* vol. 58, No. 3, pp. 282-285.

Koehler, James K. 1981. "Surface Alterations During the Capacitation of Mammalian Spermatozoa." *American Journal of Primatology.* vol. 1, pp. 131-141.

Yanagimachi, Ryuzo et al. 1981. "Sperm Autoantigens and Fertilization: II. Effects of Anti-Guinea Pig Sperm Autoantibodies on Sperm-Ovum Interactions." *Biology of Reproduction.* vol. 24, pp. 512-518.

Greve, Jeffrey M. et al. Dec. 1982. "Biosynthesis of the Major Zona Pellucida Glycoprotein Secreted by Oocytes During Mammalian Oogenesis." *Cell.* vol. 31 (Part 2), pp. 749-759.

Ficsor, Gyula et al. Apr. 1983. "Gelatin-Substrate Film Technique for Detection of Acrosin in Single Mammalian Sperm." *Fertility and Sterility.* vol. 39, No. 4, pp. 548-552.

Bleil, Jeffrey D. and Paul M. Wassarman. 1983. "Sperm-Egg Interactions in the Mouse: Sequence of Events and Induction of the Acrosome Reaction by a Zona Pellucida Glycoprotein." *Developmental Biology.* vol. 95, pp. 317-324.

Mack, S. et al. 1983. "Acrosomal Enzymes of Human Spermatozoa Before and After In Vitro Capacitation." *Biology of Reproduction.* vol. 28, pp. 1032-1042.

Hyne, R. V. et al. 1984. "Sodium Requirement for Capacitation and Membrane Fusion During the Guinea-Pig Sperm Acrosome Reaction." *J. Reprod. Fert.* vol. 70, pp. 83-94.

Ward, Cynthia R. and Bayard T. Storey. 1984. "Determination of the Time Course of Capacitation in Mouse Spermatozoa Using a Chlortetracycline Fluorescence Assay." *Developmental Biology.* vol. 104, pp. 287-296.

Bleil, Jeffrey D. and Paul M. Wassarman. Apr. 1986. "Autoradiographic Visualization of the Mouse Egg's Sperm Receptor Bound to Sperm." *The Journal of Cell Biology.* vol. 102, pp. 1363-1371.

Menken, Jane et al. Sep. 26, 1986. "Age and Infertility." *Science.* vol. 233, pp. 1389-1394.

Barbosa, James A. et al. Nov. 1987. "Site-Directed Mutagenesis of Class I HLA Genes: Role of Glycosylation in Surface Expression and Functional Recognition." *J. Exp. Med.* vol. 166, pp. 1329-1350.

Fournier-Delpech, Suzanne and Michel Courot. 1987. "Sperm—Zona Pellucida Binding Activity." *Oxford Reviews of Reproductive Biology.* vol. 9, pp. 294-300.

Lee, Michael A. et al. Oct. 1987. "Capacitation and Acrosome Reactions in Human Spermatozoa Monitored by a Chlortetracycline Fluorescence Assay." *Fertility and Sterility.* vol. 48, No. 4, pp. 649-658.

Timmons, T. M. et al. 1987. "Use of Specific Monoclonal and Polyclonal Antibodies to Define Distinct Antigens of the Porcine Zonae Pellucidae." *Biology of Reproduction.* vol. 36, pp. 1275-1287.

Burkman, Lani J. et al. Apr. 1988. "The Hemizona Assay (HZA): Development of a Diagnostic Test for the Binding of Human Spermatozoa to the Human Hemizona Pellucida to Predict Fertilization Potential." *Fertility and Sterility.* vol. 49, No. 4, pp. 688-697.

Bleil, Jeffrey D. and Paul M. Wassarman. Sep. 1988. "Galactose at the Nonreducing Terminus of O-Linked Oligosaccharides of Mouse Egg Zona Pellucida Glycoprotein ZP3 Is Essential for the Glycoprotein's Sperm Receptor Activity." *Proc. Natl. Acad. Sci. USA.* vol. 85, pp. 6778-6782.

Kinloch, Ross A. et al. Sep. 1988. "Primary Structure of the Mouse Sperm Receptor Polypeptide Determined by Genomic Cloning." *Proc. Natl. Acad. Sci. USA.* vol. 85, pp. 6409-6413.

Mansour, Suzanne L. et al. Nov. 24, 1988. "Disruption of the Proto-Oncogene *int*-2 in Mouse Embryo-Derived Stem Cells: A General Strategy for Targeting Mutations to Non-Selectable Genes." *Nature.* vol. 336, No. 6197, pp. 348-352.

Cross, Nicholas L. et al. 1988. "Induction of Acrosome Reactions by the Human Zona Pellucida." *Biology of Reproduction.* vol. 38, pp. 235-244.

Liu, De Yi et al. Nov. 1988. "A Human Sperm-Zona Pellucida Binding Test Using Oocytes That Failed to Fertilize In Vitro." *Fertility and Sterility.* vol. 50, No. 5, pp. 782-788.

Macek, Mary Beth and Barry D. Shur. 1988. "Protein-Carbohydrate Complementarity in Mammalian Gamete Recognition." *Gamete Research.* vol. 20, pp. 93-109.

Shabanowitz, R. B. and M. G. O'Rand. 1988. "Characterization of the Human Zona Pellucida from Fertilized and Unfertilized Eggs." vol. 82, pp. 151-161.

Bleil, Jeffrey D. et al. 1988. "Identification of a Secondary Sperm Receptor in the Mouse Egg Zona Pellucida: Role in Maintenance of Binding of Acrosome-Reacted Sperm to Eggs." *Developmental Biology.* vol. 128, pp. 376-385.

Kennedy, W.P. et al. May/Jun. 1989. "A Simple, Clinical Assay to Evaluate the Acrosin Activity of Human Spermatozoa." *Journal of Andrology.* vol. 10, No. 3, pp. 221-231.

Leyton, Lisette and Patricia Saling. Jun. 1989. "Evidence That Aggregation of Mouse Sperm Receptors by ZP3 Triggers the Acrosome Reaction." *The Journal of Cell Biology.* vol. 108, pp. 2163-2168.

Vazquez, Monica H. et al. 1989. "Interaction of Mouse Sperm With Purified Sperm Receptors Covalently Linked to Silica Beads." *Journal of Cell Science.* vol. 92, pp. 713-722.

Oehninger, Sergio et al. Jan. 1990. "Antagonistic and Agonistic Properties of Saccharide Moieties in the Hemizona Assay." *Fertility and Sterility.* vol. 53, No. 1, pp. 143-149.

Chamberlin, Margaret E. and Jurrien Dean. Aug. 1990. "Human Homolog of the Mouse Sperm Receptor." *Proc. Natl. Acad. Sci. USA.* vol. 87, pp. 6014-6018.

Jones, R. 1990. "Identification and Functions of Mammalian Sperm-Egg Recognition Molecules During Fertilization." *J. Reprod. Fert., Suppl.* vol. 42, pp. 89-105.

Kopf, G. S. 1990. "Zona Pellucida-Mediated Signal Transuction in Mammalian Spermatozoa." *J. Reprod. Fert., Suppl.* vol. 42, pp. 33-49.

Oehninger, Sergio et al. Jan. 1991. "Nature of the Inhibitory Effect of Complex Saccharide Moieties on the Tight Binding of Human Spermatozoa to the Human Zona Pellucida." *Fertility and Sterility.* vol. 55, No. 1, pp. 165-169.

Schwoebel, Eric et al. Apr. 15, 1991. "Isolation and Characterization of a Full-Length cDNA Encoding the 55-kDa Rabbit Zona Pellucida Protein." *The Journal of Biological Chemistry.* vol. 266, No. 11, pp. 7214-7219.

Oehninger, Sergio et al. May 1991. "Recurrent Failure of In Vitro Fertilization: Role of the Hemizona Assay in the Sequential Diagnosis of Specific Sperm-Oocyte Defects." *Am. J. Obstet. Gynecol.* vol. 164, pp. 1210-1215.

Kinloch, Ross A. et al. Nov. 1991. "Embryonal Carcinoma Cells Transfected with ZP3 Genes Differentially Glycosylate Similar Polypeptides and Secrete Active Mouse Sperm Receptor." *The Journal of Cell Biology.* vol. 115, No. 3, pp. 655-664.

Academic Press, Inc. 1991. "Errata." *Developmental Biology.* vol. 145, pp. 203-204.

Aarons, David et al. 1991. "Acrosome Reaction Induced by Immunoaggregation of a Proteinase Inhibitor Bound to the Murine Sperm Head." *Molecular Reproduction and Development.* vol. 30, pp. 258-264.

Macek, Mary Beth et al. 1991. "Aggregation of β-1,4-Galactosyltransferase on Mouse Sperm Induces the Acrosome Reaction." *Developmental Biology.* vol. 147, pp. 440-444.

Mortillo, Steven and Paul M. Wassarman. 1991. "Differential Binding of Gold-Labeled Zona Pellucida Glycoproteins mZP2 and mZP3 to Mouse Sperm Membrane Compartments." *Development.* vol. 113, pp. 141-149.

Wassarman, Paul M. and Steven Mortillo. 1991. "Structure of the Mouse Egg Extracellular Coat, the Zona Pellucida." *International Review of Cytology.* vol. 130, pp. 85-87.

Dean, Jurrien. Apr. 1992. "Biology of Mammalian Fertilization: Role of the Zona Pellucida." *The Journal of Clinical Investigation, Inc.* vol. 89, pp. 1055-1059.

Oehninger, Sergio. 1992. "Diagnostic Significance of Sperm-Zona Pellucida." *Reproductive Medicine Review.* vol. 1, pp. 57-81.

Oehninger, S. et al. 1992. "Hemizona Assay and Its Impact on the Identification and Treatment of Human Sperm Dysfunctions." *Andrologia.* vol. 24, pp. 307-321.

Prasher, Douglas C. et al. 1992. "Primary Structure of the *Aequorea Victoria* Green-Fluorescent Protein." *Gene.* vol. 111, pp. 229-233.

Rosiere, Thomas K. and Paul M. Wassarman. 1992. "Identification of a Region of Mouse Zona Pellucida Glycoprotein mZP3 That Possesses Sperm Receptor Activity." *Developmental Biology.* vol. 154, pp. 309-317.

Salzberger, Z. et al. 1992. "Loss of Acid Phosphatase from Rat Spermatozoa as a Method for Assessing the Acrosome Reaction." *Andrologia.* vol. 24, pp. 155-159.

Van Duin, Marcel et al. 1992. "Cloning and Characterization of the Human Sperm Receptor Ligand ZP3: Evidence for a Second Polymorphic Allele with a Different Frequency in the Caucasian and Japanese Populations." *Genomics.* vol. 14, pp. 1064-1070.

Thillai-Koothan, P. et al. May 1993, "Cloning, Sequencing and Oocyte-Specific Expression of the Marmoset Sperm Receptor Protein, ZP3." *Zygote.* vol. 1, pp. 93-101.

Toner, James P. and Jill Taylor Flood. Jun. 1993. "Fertility After the Age of 40." *Perimenopausal Health Care.* vol. 20, No. 2, pp. 261-272.

Patankar, Manish S. et al. Oct. 15, 1993. "A Revised Structure for Fucoidan May Explain Some of Its Biological Activities." *The Journal of Biological Chemistry.* vol. 268, No. 29, pp. 21770-21776.

Oehninger, Sergio et al. 1993. "The Specificity of Human Spermatozoa/Zona Pellucida Interaction Under Hemizona Assay Conditions." *Molecular Reproduction and Development.* vol. 35, pp. 57-61.

Yurewicz, Edward C. et al. 1993. "Porcine Zona Pellucida ZP3α Glycoprotein Mediates Binding of the Biotin-Labeled $M_r$ 55,000 Family (ZP3) to Boar Sperm Membrane Vesicles." *Molecular Reproduction and Development.* vol. 36, pp. 382-389.

Wang, Shengxian and Tulle Hazelrigg. Jun. 2, 1994. "Implications for *bcd* mRNA Localization from Spatial Distribution of *exu* Protein in *Drosophila* Oogenesis." *Nature.* vol. 369, pp. 400-403.

Arts, Eugene G. J. M. et al. Nov. 1994. "A New Method to Detect Acrosome-Reacted Spermatozoa Using Biotinylated Soybean Trypsin Inhibitor." *Fertility and Sterility.* vol. 62, No. 5, pp. 1044-1055.

Bielfeld, Peter et al. Dec. 1994. "Are Capacitation or Calcium Ion Influx Required for the Human Sperm Acrosome Reaction?" *Fertility and Sterility.* vol. 62, No. 6, pp. 1255-1261.

Flach, Jean et al. Dec 1994. "A Yeast RNA-Binding Protein Shuttles Between the Nucleus and the Cytoplasm." *Molecular and Cellular Biology.* vol. 14, No. 12, pp. 8399-8407.

Gupta, S.K. et al. 1994. "Immunoreactivity With Native Zona Pellucida of Antibodies Against a 19 Amino Acid Synthetic Peptide Corresponding to Human ZP3." *Journal of Reproductive Immunology.* vol. 27, pp. 241-247.

Harris, Jeffrey D. et al. 1994. "Cloning and Characterization of Zona Pellucida Genes and cDNAs from a Variety of Mammalian Species: The ZPA, ZPB and ZPC Gene Families." *DNA Sequence—The Journal of Sequencing and Mapping.* vol. 4, pp. 361-393.

Inouye, Satoshi and Frederick I. Tsuji. 1994. "Evidence for Redox Forms of the *Aequorea* Green Fluorescent Protein." *FEBS Letters.* vol. 351, pp. 211-214.

Van Duin, Marcel et al. 1994. "Recombinant Human Zona Pellucida Protein ZP3 Produced by Chinese Hamster Ovary Cells Induces the Human Sperm Acrosome Reaction and Promotes Sperm-Egg Fusion." *Biology of Reproduction.* vol. 51, pp. 607-617.

Kinloch, Ross A. et al. Jan. 1995. "Mapping the Mouse ZP3 Combining Site for Sperm by Exon Swapping and Site-Directed Mutagenesis." *Proc. Natl. Acad. Sci. USA.* vol. 92, pp. 263-267.

Marshall, John et al. Feb. 1995. "The Jellyfish Green Fluorescent Protein: A New Tool for Studying Ion Channel Expression and Function." *Neuron.* vol. 14, pp. 211-215.

Oehninger, Sergio et al. Feb 1995. "Factors Affecting Fertilization: Endometrial Placental Protein 14 Reduces the Capacity of Human Spermatozoa to Bind to the Human Zona Pellucida." *Fertility and Sterility.* vol. 63, No. 2, pp. 377-383.

Henkel, Ralf et al. May/Jun. 1995. "Acrosin Activity of Human Spermatozoa by Means of a Simple Gelatinolytic Technique: A Method Useful for IVF." *Journal of Andrology.* vol. 16, No. 3, pp. 272-277.

Perry, Raquel L. et al. Jul. 1995. "A Time Course Study of Capacitation and the Acrosome Reaction in Human Spermatozoa Using a Revised Chlortetracycline Pattern Classification." *Fertility and Sterility.* vol. 64, No. 1, pp. 150-159.

Dell, Anne et al. Oct. 13, 1995. "Structural Analysis of the Oligosaccharides Derived from Glycodelin, a Human Glycoprotein with Potent Immunosuppressive and Contraceptive Activities." *The Journal of Biological Chemistry*. vol. 270, No. 41, pp. 24116-24126.

Clark, Gary F. et al. 1995. "New Concepts in Human Sperm-Zona Pellucida Interaction." *Human Reproduction*. vol. 10, Supplement 1, pp. 31-37.

Gupta, S.K. et al. 1995. "Localization of Epitopes for Monoclonal Antibodies at the N-Terminus of the Porcine Zona Pellucida Glycoprotein pZPC." *Molecular Reproduction and Development*. vol. 42, pp. 220-225.

Kipersztok, Simon et al. 1995. "POM-ZP3, a Bipartite Transcript Derived from Human ZP3 and a *POM121* Homologue." *Genomics*. vol. 25, pp. 354-359.

MacKenna, A. 1995. "Contribution of the Male Factor to Unexplained Infertility: A Review." *International Journal of Andrology*. vol. 18 , Suppl. 1, pp. 58-61.

Stearns, Tim. 1995. "The Green Revolution: Green Fluorescent Protein Allows Gene Expression and Protein Localization to be Observed in Living Cells." *Current Biology*. vol. 5, No. 3, pp. 262-264.

Wassarman, Paul M. and Eveline S. Litscher. 1995. "Sperm—Egg Recognition Mechanisms in Mammals." *Current Topics in Developmental Biology*. vol. 30, pp. 1-19.

Oehninger, Sergio et al. Jan. 1996. "Use of a Specific Zona Pellucida (ZP) Protein 3 Antiserum as a Clinical Marker for Human ZP Integrity and Function." *Fertility and Sterility*. vol. 65, No. 1, pp. 139-145.

Litscher, Eveline S. and Paul M. Wassarman. Aug. 1996. "Recombinant Hamster Sperm Receptors that Exhibit Species-Specific Binding to Sperm." *Zygote*. vol. 4, pp. 229-236.

Cheng, Feng-Pang et al. Nov./Dec. 1996. "Use of Peanut Agglutinin to Assess the Acrosomal Status and the Zona Pellucida-Induced Acrosome Reaction in Stallion Spermatozoa." *Journal of Andrology*. vol. 17, No. 6, pp. 674-682.

Morris, Howard R. et al. Dec. 13, 1996. "Gender-Specific Glycosylation of Human Glycodelin Affects Its Contraceptive Activity." *The Journal of Biological Chemistry*. vol. 271, No. 50, pp. 32159-32167.

Barros, C. et al. 1996. "Early Steps of Sperm-Egg Interactions During Mammalian Fertilization." *Cell Biology International*. vol. 20, No. 1, pp. 33-39.

Chapman, Neil R. and Christopher L.R. Barratt. 1996. "The Role of Carbohydrate in Sperm-ZP3 Adhesion." *Molecular Human Reproduction*. vol. 2, No. 10, pp. 767-774.

Clark, Gary F. et al. 1996. "A Role for Glycoconjugates in Human Development: The Human Feto-Embryonic Defence System Hypothesis." *Human Reproduction*. vol. 11, No. 3, pp. 467-473.

Clark, Gary F. et al. 1996. "Role for Glycoconjugates in Cellular Communication in the Human Reproductive System." *Molecular Human Reproduction*. vol. 2, No. 7, pp. 513-517.

Liu, De Yi and H.W. Gordon Baker. 1996. "A Simple Method for Assessment of the Human Acrosome Reaction of Spermatozoa Bound to the Zona Pellucida: Lack of Relationship With Ionophore A23187-Induced Acrosome Reaction." *Human Reproduction*. vol. 11, No. 3, pp. 551-557.

Mortimer, David and Lynn Fraser. 1996. "Consensus Workshop on Advanced Diagnostic Andrology Techniques: ESHRE Andrology Special Interest Group." *Human Reproduction*. vol. 11, No. 7, pp. 1463-1479.

Whitmarsh, A.J. et al. 1996. "Biological Activity of Recombinant Human ZP3 Produced *In Vitro*: Potential for a Sperm Function Test." *Molecular Human Reproduction*. vol. 2, No. 12, pp. 911-919.

Oehninger, Sergio et al. Mar. 1997. "Approaching the Next Millennium: How Should We Manage Andrology Diagnosis in the Intracytoplasmic Sperm Injection Era?" *Fertility and Sterility*. vol. 67, No. 3, pp. 434-436.

Oehninger, Sergio et al. Jun. 1997. "Clinical Significance of Human Sperm-Zona Pellucida Binding." *Fertility and Sterility*. vol. 67, No. 6, pp. 1121-1127.

Bagavant, Harini et al. 1997. "Immunogenicity and Contraceptive Potential of a Human Zona Pellucida 3 Peptide Vaccine." *Biology of Reproduction*. vol. 56, pp. 764-770.

Carver-Ward, J. A. et al. 1997, "Genetics: Comparative Flow Cytometric Analysis of the Human Sperm Acrosome Reaction Using CD46 Antibody and Lectins." *Journal of Assisted Reproduction and Genetics*. vol. 14, No. 2, pp. 111-119.

Franken, D. R. et al. 1997. "Zona Pellucida Mediated Acrosome Reaction and Sperm Morphology." *Andrologia*. vol. 29, pp. 311-317.

Hansen, Jan E. et al. 1997. "O-GLYCBASE Version 2.0: A Revised Database of O-Glycosylated Proteins." *Nucleic Acid Research*. vol. 25, No. 1, pp. 278-282.

Kohn, F.M. et al. 1997. "Detection of Human Sperm Acrosome Reaction: Comparison Between Methods Using Double Staining, *Pisum sativum* Agglutinin, Concanavalin A and Transmission Electron Microscopy." *Human Reproduction*. vol. 12, No. 4, pp. 714-721.

Liu, Chengyu et al. 1997. "Zona Pellucida Glycoprotein mZP3 Bioactivity Is Not Dependent on the Extent of Glycosylation of Its Polypeptide or on Sulfation and Sialylation of Its Oligosaccharides." *Journal of Cell Science*. vol. 110, pp. 745-752.

Margalit, I. et al. 1997. "A Novel Method for Evaluating the Acrosomal Status of Mammalian Spermatozoa." *Archives of Andrology*. vol. 38, pp. 87-99.

Mortensen, Richard et al. 1997. "Selection of Transfected Mammalian Cells." *Current Protocols in Molecular Biology*. pp. 9.5.1-9.5.6.

Patankar, Manish S. et al. 1997. "Expression of Glycans Linked to Natural Killer Cell Inhibition on the Human Zona Pellucida." *Molecular Human Reproduction*. vol. 3, No. 6, pp. 501-505.

Shalgi, R. and T. Raz. 1997. "The Role of Carbohydrate Residues in Mammalian Fertilization." *Histol Histopathol*. vol. 12, pp. 813-822.

Arkin, Shy. Feb. 20, 1998. "Protein Glycosylation." www.bio.cam.ac.uk/~sa232/tex/MVSTIA_4-8_Shy/node13.html. Printed Feb. 4, 1999.

Chen, Jie et al. May 1998. "Inactivation of the Mouse Sperm Receptor, mZP3, by Site-Directed Mutagenesis of Individual Serine Residues Located at the Combining Site for Sperm." *Proc. Natl. Acad. Sci. USA*. vol. 95, pp. 6193-6197.

Hansen, Jan. Aug. 4, 1998. "NetOGlyc 2.0 Prediction Server: Center for Biological Sequence Analysis." www.cbs.dtu.dk/services/NetOGlyc/. Printed Feb. 4, 1999.

Chuang, Alex T. and Stuart S. Howards. Nov. 1998. "Male Infertility: Evaluation and Nonsurgical Therapy." *Office Management of Urologic Problems*. vol. 25, No. 4, pp. 703-713.

Greenhouse, Stephen et al. 1998. "Insights from Model Systems: Genetic Causes of Female Infertility: Targeted Mutagenesis in Mice." *Am. J. Hum. Genet*. vol. 62, pp. 1282-1287.

Hansen, Jan E. et al. 1998. "NetOglyc: Prediction of Mucin Type O-Glycosylation Sites Based on Sequence Context and Surface Accessibility." *Glycoconjugate Journal*. vol. 15, pp. 115-130.

Henkel, R. et al. 1998. "Zona Pellucida as Physiological Trigger for the Induction of Acrosome Reaction." *Adrologia*. vol. 30, pp. 275-280.

Oehninger, S. et al. 1998. "Involvement of Selectin-Like Carbohydrate Binding Specificity in Human Gamete Interaction." *Andrologia*. vol. 30, pp. 269-274.

Ozgur, Kemal et al. 1998. "Direct Evidence for the Involvement of Carbohydrate Sequences in Human Sperm-Zona Pellucida Binding." *Molecular Human Reproduction*. vol. 4, No. 4, pp. 318-324.

Jaiswal, B.S. et al. 1999. "Detection of Partial and Complete Acrosome Reaction in Human Spermatozoa: Which Inducers and Probes to Use?" *Molecular Human Reproduction*. vol. 5, No. 3, pp. 214-219.

Dean, Jurien. Jun. 24, 2000. "Maternal Effects on Folliculogenesis, Fertilization and Early Development." *Program & Abstracts: The Endocrine Society's 82nd Annual Meeting*. Ooctye Development Symposium Session.

Patra, Ashok K. et al. 2000. "Refolding, Structural Transition and Spermatozoa-Binding of Recombinant Bonnet Monkey (*Macaca radiata*) Zona Pellucida Glycoprotein-C Expressed in *Escherichia coli*." *Eur. J. Biochem*. vol. 267, pp. 7075-7081.

Pietrobon, Elisa O. et al. Jan./Feb. 2001. "Detection of the Mouse Acrosome Reaction by Acid Phosphatase. Comparison With Chlortetracycline and Electron Microscopy." *Journal of Andrology.* vol. 22, No. 1, pp. 96-103.

Dong, Ke Wen et al. Apr. 2001. "Characterization of the Biologic Activities of a Recombinant Human Zona Pellucida Protein 3 Expressed in Human Ovarian Teratocarcinoma (PA-1) Cells." *Am. J. Obstet. Gynecol.* vol. 184, pp. 835-844.

Esterhuizen, A.D. et al. 2001. "Clinical Importance of Zona Pellucida-Induced Acrosome Reaction and Its Predictive Value for IVF." *Human Reproduction.* vol. 16, No. 1, pp. 138-144.

Topfer-Petersen E. et al. 1990. "Cell biology of acrosomal proteins." *Andrologia;* vol. 22, No. 1, pp. 110-121.

Kolluri, SK et al. 1995. "Nucleotide sequence of cDNA encoding bonnet monkey (Macaca radiata) zona pellucida glycoprotein-ZP3." *Reprod. Fert. Dev.* vol. 7, No. 5, pp. 1209-1212.

Bruch, J et al. 1996. "Mapping of type I loci from human chromosome 7 reveals segments of conserved synteny on pig chromosomes 3, 9, and 18." *Cytogenet. Cell. Genet.* vol. 73, No. 3, pp. 164-167.

Epifano, O. et al. Nov. 1995. "Mouse ZP1 encodes a zona pellucida protein homologous to egg envelope proteins in mammals and fish." *J. Biol. Chem.* vol. 270, No. 45, pp. 27254-27258.

Lou, YH et al. Oct. 1995. "Altered target organ. A mechanism of postrecovery resistance to murine autoimmune oophoritis." *J. Immunol.* vol. 155, No. 7, pp. 3667-3673.

Aitken, RJ et al. May 1995. "Redox regulation of tyrosine phosphorylation in human spermatazoa and its role in the control of human sperm function." *J. Cell. Sci.* vol. 108, No. 5, pp. 2017-2025.

Nata, K. et al. Jun. 1995. "The structure of the Aplysia kurodai gene encoding ADP-ribosyl cyclase, a second-messenger enzyme." *Gene.* vol. 158, No. 2, pp. 213-218.

Bercegeay, S. et al. 1995. "Composition of Human Zona Pellucida as Revealed by SDS-PAGE After Silver Staining." *Molecular Reproduction and Development.* 41, p. 355-359.

Naz, RK et al. Dec. 1994. "Molecular identities of human sperm proteins that bind human zona pellucida: nature of sperm-zona interaction, tyrosine kinase activity, and the involvement of FA-1." *Mol. Reprod. Dev.* vol. 39, No. 4, pp. 397-408.

Bagavant, H. et al. Sep. 1994. "Antifertility effects of porcine zona pellucida-3 immunization using permissible adjuvants in female bonnet monkeys (Macaca radiato): reversibility, effect on follicular development and hormonal profiles." *J. Reprod. Fert.*, vol. 102, No. 1, pp. 17-25.

Hinsch, KD et al. Oct. 1994. "Anti-ZP3 antibodies binding to the human zona pellucida: effect of oocyte-storage conditions." *Am. J. Reprod. Immunol.* vol. 32, No. 3, pp. 146-151.

Wydner, KS et al. Sep. 1994. "Use of an intron polymorphism to localize the tropoelastin gene to mouse chromosome 5 in a region of linkage conservation with human chromosome 7." *Genomics.* vol. 23, No. 1, pp. 125-131.

Cui, KH et al. Jan. 1994. "Sex determination of preimplantation embryos by human testis-determining gene amplification." *Lancet.* vol. 343, No. 8889, pp. 79-82.

Crozet, N. May 1994. "Acrosome reaction and fertilization." *Contracept. Fertil. Sex.* vol. 22, No. 5, pp. 328-330.

Bagavant, H. et al. Dec. 1993. "Block in porcine gamete interaction by polyclonal antibodies to a pig ZP3 beta fragment having partial sequence homology to human ZP3." *J. Reprod. Immunol.* vol. 25, No. 3, pp. 277-283.

Yurewicz, EC et al. May 1993. "Generation and characterization of site-directed antisera against an amino-terminal segment of a 55 kDa sperm adhesive glycoprotein from zona pellucida of pig oocytes." *J. Reprod. Fertil.* vol. 98, No. 1, pp. 147-152.

Yurewicz, EC et al. Aug. 1993. "Nucleotide sequence of cDNA encoding ZP3 alpha, a sperm-binding glycoprotein from zona pellucida of pig oocyte." *Biochim. Biophys. Acta.* vol. 1174, No. 2, pp. 211-214.

Van Duin, M. et al. 1993. "The human gene for zona pellucida glycoprotein ZP3 and a second polymorphic locus are located on chromosome 7." *Cytogenet. Cell. Genet.* vol. 63, No. 2, pp. 111-113.

Rhim, SH et al. Jan. 1992. "Autoimmune disease of the ovary induced by a ZP3 peptide from the mouse zona pellucida." *J. Clin. Invest.* vol. 89, No. 1, pp. 28-35.

Yurewicz, EC et al. Oct. 1992. "Porcine oocyte zona pellucida M(r) 55,000 glycoproteins: identification of O-glycosylated domains." *Mol. Reprod. Dev.* vol. 33, No. 2, pp. 182-188.

Paterson, M. et al. Apr. 1992. "Analysis of the contraceptive potential of antibodies against native and deglycosylated porcine ZP3 in vivo and in vitro." *Biol. Reprod.* vol. 46, No. 4, pp. 523-534.

Tulsiani, DR et al. Jan. 1992. "Evidence for the presence of high-mannose/hybrid oligosaccharide chain(s) on the mouse ZP2 and ZP3." *Biol. Reprod.* vol. 46, No. 1, pp. 93-100.

Rosiere, Thomas K. et al. 1992. "Identification of a Region of Mouse Zona Pellucida Glycoprotein mZP3 That Possesses Sperm Receptor Activity." *Developmental Biology.* 154, p. 309-317.

Naz, RK et al. May 1991. "Role of membrane phosphotyrosine proteins in human spermatozoal function." *J. Cell. Sci.* vol. 99, No. 1, pp. 157-165.

Koyama, K. et al. Nov. 1991. "Blocking of human sperm-zona interaction by monoclonal antibodies to a glycoprotein family (ZP4) of porcine zona pellucia." *Biol. Reprod.* vol. 45, No. 5, pp. 727-735.

Yurewicz, EC et al. Oct. 1991. "Isolation, composition, and biological activity of sugar chains of porcine oocyte zona pellucida 55K glycoproteins." *Mol. Reprod. Dev.* vol. 30, No. 2, pp. 126-134.

Millar, SE et al. Dec. 1991. "Oocyte-specific factors bind a conserved upstream sequence required for mouse zona pellucida promoter activity." *Mol. Cell. Biol.* vol. 11, No. 12, pp. 6197-6204.

Keenan, JA et al. Jan. 1991. "Endocrine response in rabbits immunized with native versus deglycosylated porcine zona pellucida antigens." *Biol. Reprod.* vol. 44, No. 1, pp. 150-156.

Naz, RK et al. May 1991. "Human spermatozoal FA-1 binds with ZP3 of porcine zona pellucida." *J. Reprod. Immunol.* vol. 20, No. 1, pp. 43-58.

Hasegawa, A. Feb. 1991. "Isolation of four major glycoprotein families (ZP1, ZP2, ZP3, ZP4) of porcine zona pellucida and characterization of antisera raised to each glycoprotein family." *Nippon Sanka Fujinka Gakkni Zasshi.* vol. 43, No. 2, pp. 221-226.

Saling, Patricia M. 1991. "How the Egg Regulates Sperm Function During Gamete Interaction: Facts and Fantasies." *Biology of Reproduction.* 44, p. 246-251.

Von-Bernhardi, R. et al. Jan.-Feb. 1990. "Round-headed spermatozoa: a model to study the role of the acrosome in early events of gamete interaction." *Andrologia.* vol. 22, No. 1, pp. 12-20.

Shabanowitz, RB. Aug. 1990. "Mouse antibodies to human zona pellucida: evidence that human ZP3 is strongly immunogenic and contains two distinct isomer chains." *Biol. Reprod.* vol. 43, No. 2, pp. 260-270.

Kinloch, RA and Wasserman, PM. Dec. 1989. "Profile of a mammalian sperm receptor gene." *New Biol.* vol. 1, No. 3, pp. 232-238.

Saling, Patricia M. 1989. Mammalian Sperm Interaction with Extracellular Matrices of the Egg. *Oxf. Rev. Reprod. Biol.* vol. 11, pp. 339-388.

Conover, JC and Gwatkin, RB. Jul. 1988. "Fertilization of zona-drilled mouse oocytes treated with a monoclonal antibody to the zona glycoprotein, ZP3." *J. Exp. Zool.* vol. 247, No. 1, pp. 113-118.

Shabanowitz, RB and O'Rand, MG. 1988. "Molecular changes in the human zona pellucida associated with fertilization and human sperm-zona interactions." *Ann. N.Y. Acad. Sci.* vol. 541, pp. 621-632.

Oehninger, S. et al. 1992. "Male infertility: the impact of assisted reproductive technologies." *Curr. Opin. Obstet. Gynecol.* vol. 4, pp. 185-196.

Tsubamoto, H. et al. 1999. "Expression of recombinant human zona pellucida protein 2 and its binding capacity to spermatazoa." *Biol. Reprod.* vol. 61, pp. 1649-1654.

Yanagimachi, R. 1981. "Mechanisms of fertilization in mammals", In Mastroianni L Jr and Biggers JD (eds): *Fertilization and Embryonic Development In Vitro.* New York, Plenum Press, pp. 81-182.

Chalfie, M. et al. Feb. 1994. "Green fluorescent protein as a marker for gene expression." *Science.* vol. 263, No. 5148, pp. 802-805.

Irvine, D. S. 1998. "Epidemiology and aetiology of male infertility." *Hum. Reprod.* vol. 13, No. 1, pp. 33-44.

\* cited by examiner

Acrosin activity after induced by calcium ionophore A23187, progesterone and negative control.

FIG. 5

MetGluLeuSerTyrArgLeuPheIleCysLeuLeuLeuTrpGlySerThrGluLeuCysTyrProGlnProLeuTrpLeuLeuGlnGlyGlyAlaSer
1               5                  10                 15                 20                 25                 30

HisProGluThrSerValGlnProValLeuValGlyCysGlnGluAlaThrLeuMetValSerLysAspLeuPheGlyThrGlyLysLeuIle
          35                 40                 45                 50                 55                 60                 65

ArgAlaAlaAspLeuThrGlyProGluAlaCysGluProLeuValSerMetAspThrGluProValValArgPheGluValGlyLeuHisGluCys
          70                 75                 80                 85                 90                 95

GlyAsnSerMetGlnValThrAspAspAlaLeuValTyrSerThrPheLeuLeuHisAspProArgProValGlyAsnLeuSerIleValArgThrAsn
100                105                110                115                120                125                130

ArgAlaGluIleProIleGluCysArgTyrProArgGlnGlyAsnValSerSerGlnAlaIleLeuProThrTrpLeuProPheArgThrThrValPheSerGlu
          135                140                145                150                155                160                165

GluLysLeuThrPheSerLeuArgLeuMetGluAsnTrpAsnAlaGluSerProThrPheHisLeuGlyAspAlaAlaAlaHisLeuGlnAlaGlu
          170                175                180                185                190                195                200

IleHisThrGlySerHisValProLeuArgLeuPheValAspHisCysValAlaThrProThrTyrHisThrIleValAspPheHis
          205                210                215                220                225                230                235

GlyCysLeuValAspGlyLeuThrAspAlaSerSerAlaPheLysValProArgGlyProGlyAspThrLeuGlnPheThrValAspValPheHisAlaAsn
          240                245                250                255                260                265                270

AspSerArgAsnMetIleTyrIleThrCysHisLeuLysValThrLeuAlaGluAsnAspProAspGluLeuAsnLysAlaCysSerPheSerLysProSerAsn
          275                280                285                290                295                300                305

SerTrpPheProValGluGlyProAlaAspIleCysGlnCysCysAsnLysGlyAspCysGlyThrProSerHisSerArgArgGlnProHisValMetSerGln
          310                315                320                325                330                335                340

TrpSerArgSerAlaSerArgAsnArgArgHisValThrGlyGluAlaAspThrValGlyProLeuIlePheLeuAspArgArgGlyAspHisGluVal
          345                350                355                360                365                370                375

GluGlnTrpAlaLeuProSerAspThrSerValValGlyLeuAlaValValSerLeuThrLeuValIleLeuValThrArgArg
          380                385                390                395                400                405                410

CysArgThrAlaSerHisProValSerAlaSerGlu (SEQ ID NO: 1)
          415                420

SEQUENCE LISTING

<160> NUMBER OF SEQ ID NOS: 1

<210> SEQ ID NO 1
<211> LENGTH: 424
<212> TYPE: PRT
<213> ORGANISM: Homo sapiens

<400> SEQUENCE: 1

```
Met Glu Leu Ser Tyr Arg Leu Phe Ile Cys Leu Leu Leu Trp Gly Ser
1               5                  10                  15

Thr Glu Leu Cys Tyr Pro Gln Pro Leu Trp Leu Leu Gln Gly Gly Ala
            20                  25                  30

Ser His Pro Glu Thr Ser Val Gln Pro Val Leu Val Glu Cys Gln Glu
        35                  40                  45

Ala Thr Leu Met Val Met Val Ser Lys Asp Leu Phe Gly Thr Gly Lys
    50                  55                  60

Leu Ile Arg Ala Ala Asp Leu Thr Leu Gly Pro Glu Ala Cys Glu Pro
65                  70                  75                  80

Leu Val Ser Met Asp Thr Glu Asp Val Val Arg Phe Glu Val Gly Leu
                85                  90                  95

His Glu Cys Gly Asn Ser Met Gln Val Thr Asp Asp Ala Leu Val Tyr
            100                 105                 110

Ser Thr Phe Leu Leu His Asp Pro Arg Pro Val Gly Asn Leu Ser Ile
        115                 120                 125

Val Arg Thr Asn Arg Ala Glu Ile Pro Ile Glu Cys Arg Tyr Pro Arg
    130                 135                 140

Gln Gly Asn Val Ser Ser Gln Ala Ile Leu Pro Thr Trp Leu Pro Phe
145                 150                 155                 160

Arg Thr Thr Val Phe Ser Glu Glu Lys Leu Thr Phe Ser Leu Arg Leu
                165                 170                 175

Met Glu Glu Asn Trp Asn Ala Glu Lys Arg Ser Pro Thr Phe His Leu
            180                 185                 190

Gly Asp Ala Ala His Leu Gln Ala Glu Ile His Thr Gly Ser His Val
        195                 200                 205

Pro Leu Arg Leu Phe Val Asp His Cys Val Ala Thr Pro Thr Pro Asp
    210                 215                 220

Gln Asn Ala Ser Pro Tyr His Thr Ile Val Asp Phe His Gly Cys Leu
225                 230                 235                 240

Val Asp Gly Leu Thr Asp Ala Ser Ser Ala Phe Lys Val Pro Arg Pro
                245                 250                 255

Gly Pro Asp Thr Leu Gln Phe Thr Val Asp Val Phe His Phe Ala Asn
            260                 265                 270

Asp Ser Arg Asn Met Ile Tyr Ile Thr Cys His Leu Lys Val Thr Leu
        275                 280                 285
```

-continued

```
Ala Glu Gln Asp Pro Asp Glu Leu Asn Lys Ala Cys Ser Phe Ser Lys
    290             295                 300

Pro Ser Asn Ser Trp Phe Pro Val Glu Gly Pro Ala Asp Ile Cys Gln
305             310                 315                 320

Cys Cys Asn Lys Gly Asp Cys Gly Thr Pro Ser His Ser Arg Arg Gln
            325             330                 335

Pro His Val Met Ser Gln Trp Ser Arg Ser Ala Ser Arg Asn Arg Arg
            340             345                 350

His Val Thr Glu Glu Ala Asp Val Thr Val Gly Pro Leu Ile Phe Leu
        355             360             365

Asp Arg Arg Gly Asp His Glu Val Glu Gln Trp Ala Leu Pro Ser Asp
    370             375             380

Thr Ser Val Val Leu Leu Gly Val Gly Leu Ala Val Val Val Ser Leu
385             390             395             400

Thr Leu Thr Ala Val Ile Leu Val Leu Thr Arg Arg Cys Arg Thr Ala
            405             410                 415

Ser His Pro Val Ser Ala Ser Glu
            420
```

HUMAN ZONA PELLUCIDA PROTEINS AND METHODS OF THEIR USE IN DIAGNOSING MALE INFERTILITY

REFERENCE TO RELATED APPLICATIONS

This application receives priority from U.S. No. 60/309,532 filed Aug. 2, 2001 entitled "Recombinant Human ZP3 to Diagnose Male Infertility," U.S. No. 60/309,553 filed Aug. 2, 2001 entitled "Human ZP2–ZP3 Complex as Sperm Binding Agent," U.S. No. 60/339,632 filed Dec. 11, 2001 entitled "Using Released Substance After Acrosome Reaction to Detect Male Infertility," and U.S. No. 60/309,664 filed Aug. 2, 2001 entitled "Enzymes for Sperm Functionality."

FIELD OF THE INVENTION

The invention relates to diagnosis of male infertility and more specifically to the use of ZP2 and ZP3 proteins in diagnostics.

BACKGROUND OF THE INVENTION

Infertility is a significant medical problem affecting a large proportion of the population. About half of the causes of infertility arise in the male (generally the sperm or seminal fluid) and usually no specific cause can be identified, even after thorough evaluation. Several diagnostic tests for such evaluations have been developed and provide some useful information. Generally, studies of patients having unexplained infertility using these tests have reported defects in capacitation and sperm motion characteristics, binding of spermatozoa to the zona pellucida, acrosome reaction, acrosin activity of spermatozoa, and the ability of the spermatozoa to penetrate zona-free oocytes (Mackenna et al, 1995). However, only when such tests identify one or more abnormalities can more specific and cost-effective treatment regimens be instituted (Chuang et al, 1998).

An important clinical test for evaluation of male fertility uses the acrosome reaction whereby acrosin and other acrosome enzymes in sperm are released by simulation of contact with an egg or by actual contact with an egg. Almost all methods for detecting the acrosome reaction monitor a morphological change during the acrosome reaction. The most widely used methods utilize optical microscopy, wherein spermatozoa are visualized after staining. Different chemical agents such as calorimetric dyes and fluorophore labeled lectins and antibodies may be used. However the results of these tests often differ depending on the characteristics of the different agents used.

The problems of acrosome reaction tests arise from several factors, including the timing of capacitation, the reaction medium, the inducing agents, and the timing of reaction. Furthermore, the detection methods may significantly impact the final result. For example, a stain in the outer acrosome membrane typically gives a different result than a stain in the inner acrosome membrane. Perhaps the most reliable method for detection of the AR is electron microscopy. Unfortunately this procedure cannot be used routinely because it is expensive and labor-intensive. Most present methods utilize an optical microscope, wherein spermatozoa are stained for the visualization of their acrosomal status. Membrane changes in the spermatozoa lead to loss of the acrosomal cap, which may be determined morphologically. However, these traditional morphological methods still are labor-intensive and generate unreliable results. More accurate and convenient methods are greatly needed for detecting AR.

Of course, more specific chemical details of the AR beyond the morphological changes are known and might be relied on for diagnosing causes of male infertility. An early development in this field has been the use of calcium ionophores to stimulate morphological changes that can be observed. A recent study of zona-induced AR (ZIAR) had found that such induction had a high predictive value for IVF results (Esterhuizen A D, 2001). Physiologically, AR is induced by zona pellucida protein and followed by the liberation of several acrosomal enzymes and other constituents that facilitate penetration of the zona. Although the AR is an important step during fertilization, this sperm function generally is not diagnosed correctly and easily by present methods. Generally, most AR studies to date have focused on the morphological change by using chemical ($Ca^{2+}$ ionophore A23187). Two major problems to date prevent widespread adoption of these techniques: 1) ($Ca^{2+}$) induced AR responses do not have the same clinical values as ZIAR (Franken D R et al, 1997); and 2) AR detection by morphological changes is subjective and labor-intensive.

Biochemical tests have been designed around assay of AR releasing acrosin and other acrosomal contents. The acrosin protein has been chosen as a marker to detect AR because it accounts for almost 20% of the total acrosomal protein. Unfortunately, despite many efforts, a reliable assay method using acrosin activity to indicate AR has not been suitably commercialized. One reason for this lack of good success is that acrosin is inhibited by two different trypsin inhibitors that exits in human seminal plasma (inhibitors (HUSI) I and II as described by E. Fink, et. Al, 1971 and H. Schiessler, et al, 1974). Both inhibitors greatly interfere with acrosin activity. A second assay for acrosin activity is the photometric enzyme method, wherein a sperm is treated with triton X-100 for lysis and to convert proacrosin to acrosin. Although this method could measure total amount of acrosin activity, it generally does not determine the amount of true acrosin activity from acrosome reacted human sperm.

Other related tests used in the modern assisted reproductive technologies field include basic semen analysis, computer-assisted evaluation of sperm motion characteristics, inducibility of the acrosome reaction, and bioassays that assess gamete interaction, which includes the hemizona assay and sperm-hamster egg penetration assay (Oehninger et al., 1997). However, the hemizona assay is too expensive, since this assay requires human egg, to become routine bioassay. And the sperm-hamster egg penetration assay needs to be implemented before its introduction as a routine clinical tool (Oehninger et al., 1997). Thus, a convenient and accurate assay that can assess the spermatozoa-oocyte interaction is necessary for today's infertility clinical therapies.

More speculation in this area considers possible use of the zona pellucida glycoproteins, which play an exclusive role in mediating the binding between spermatozoa and oocyte. ZP3 mediates an initial binding (Leyton and Saling, 1989; Aarons, et al., 1991; Macek et al., 1991) and ZP2 possibly mediates a secondary binding of spermatozoa to zona pellucida (Bleil and Wassarman, 1980; Bleil et al., 1988). The primary binding is mediated by ZP3 and its specific receptors located on the sperm plasma membrane. The zona pellucida glycoproteins are highly glycosylated and possess both Asn- (N-) linked and Ser/Thr- (O-) linked oligosaccharides. Different carbohydrates on ZP3, such as galactose in an alpha-linkage, N-acetylglucosamine in a beta-linkage, were suggested as complementary sperm receptors mediating the primary binding between a spermatozoon and the zona pellucida (Shalgi and Raz, 1997).

Studies with 125I labeled mouse egg ZP3 and ZP2 revealed 125I-ZP3 on the acrosomal cap region of spermatozoa, and the 125I-ZP2 bound preferentially to acrosome-reacted spermatozoa (Bleil and Wassarman, 1986). Studies with anti-mouse ZP3 polyclonal antisera and monoclonal antibodies indicated that antibodies do not affect primary binding of acrosome-intact sperm to eggs or secondary binding following the acrosome reaction. This indicates that complex multiple steps that require protein of specific structure mediate the sperm to egg interaction. Unfortunately, the primary binding is difficult to detect on acrosome reacted spermatozoa, since this binding occurs on the sperm plasma membrane. A further complication is that the sperm plasma membrane fuses with the outer acrosome membrane during the acrosome reaction and is destroyed or disappears after the acrosome reaction, which signal fades away.

On the other hand, secondary binding in contrast appears stronger, more irreversible and more persistent as it is mediated by proacrosin/acrosin on the inner acrosome matrx. membrane of the acrosome-reacted spermatozoa and the ZP2 in the zona pellucida (Hyne et al., 1984; Yanagimachi, 1981). That is, a complex *zona pellucida* structure undergoes complex changes based on multiple specific biochemicals. However, with the ZP2 only, it cannot bind to acrosome intact spermatozoa because without acrosome reaction the inner acrosome membrane will not be exposed. The rhZP2 expressed in *Escherichia coli,* with two hours incubation of human spermatozoa with rhZP2 in vitro, an immunofluorescent study indicated that rhZP2 bound only to acrosome-reacted spermatozoa (Tsubamoto et al., 1999).

These detailed studies, carried out by many researchers around the world indicate that the recognition between sperm and egg is a complex and incompletely understood process. The complexity revealed by the literature in this area is an indication of the difficulty in finding a good test for diagnosis male infertility. Despite this work, a generally suitable test is lacking.

The relative lack of progress in this field is unfortunate because any mutations on the ZP2 or ZP3 genes or on the genes of membrane receptors of spermatozoa might create the binding dysfunction. Today, this binding dysfunction will not be found until these patients having been go through some infertility therapies. The infertility therapies, however, is a time and money consuming procedure. Moreover, this procedure exposes the female patients under a rugged physical and mental stress. These unnecessary sufferings should and can be avoided, if patients can access the specific therapies they need in the early stage of treatment.

The need for a high quality infertility test increases with time. During the last decade, the number of infertile couple climbed significantly and will reach 6.36 million at year 2005 in U.S. Unfortunately, although spermatozoa abnormalities are a problem in up to 40% of infertile couples (Oehninger et al., 1992), an accurate and correct test that reveals information about such sperm abnormalities is lacking. This lack impacts infertility therapy, which is a time and money consuming procedure that exposes female patients to rugged physical and mental stress. Still further, infertile couples often race with time trying to solve this problem while their inability to conceive may recede with age. Accordingly, simple and accurate sperm binding diagnostic tools are needed to guide couples into needed therapies, and will benefit infertile patients physically, emotionally and financially.

SUMMARY OF THE INVENTION

A wide range of materials and methods were discovered that directly alleviate problems described above. Superior materials were discovered that provide new methodologies, improvements were discovered for existing methods and new methods and uses discovered such as pregnancy avoidance as well as infertility analysis techniques.

Such materials include, for example, ZP3, highly purified ZP3, ZP3/ZP2 complexes, ZP3/ZP2 fusion proteins, ZP3/ZP2/ZP1 complexes, ZP3/ZP2/ZP1 fusion proteins, complexes, conjugates and fusion proteins with detection agents such as fluors (including GFP), enzymes and other reagents and derivatives thereof. Embodiments also provide improved diagnostics through new methods such as an acrosome weighting system to compensate for qualitative differences in observed morphologies, new and more accurate methods to detect the acrosome reaction, and improved reagents and the like.

An embodiment of the invention, accordingly, is a high quality reagent for testing male infertility, comprising a properly glycosylated sperm binding glycopeptide complexed to a detection agent. In another embodiment such a reagent is provided wherein the glycopeptide is selected from the group consisting of: properly glycosylated rhZP3;, properly glycosylated peptide comprising at least one binding site for human sperm; properly glycosylated peptide comprising at least two binding sites for human sperm, properly glycosylated peptide comprising at least three binding sites for human sperm; rhZP3; rhZP3/ZP2 complex; rhZP3/ZP2 fusion protein prepared as a single gene product; and rhZP3/ZP2/ZP1.

Yet another embodiment is a reagent that comprises recombinantly produced ZP2 capable of forming a ZP2/ZP3 complex upon incubation with ZP3. Yet another embodiment is a reagent comprising recombinant ZP2/ZP3 complex capable of binding specifically to human sperm.

Yet another embodiment is a kit for testing male infertility, comprising a reagent as described herein and at least a buffer salt or salt solution. Yet another embodiment is a method for detecting infertility of a male, comprising the step of contacting a reagent as described herein with a sperm sample of the male. Yet another embodiment is a method for detecting infertility of a male, comprising providing a high quality reagent as described herein, contacting a sperm sample of the male with the reagent for a period of time sufficient to allow binding between the glycoprotein and the sperm, and detecting the detection agent bound to sperm.

Yet another embodiment is a method for determining infertility of a male, comprising detecting one or more substances released from a sperm sample upon induction of the acrosome reaction in sperm of the sample. In an embodiment the one or more substances are selected from the group consisting of an enzyme, acid phosphatase, protein, membrane fragment, phospholipid, cholesterol, peptide, lipoprotein, nucleotide, nucleoside and glycoprotein.

Yet another embodiment is an acrosome scoring method for determining infertility of a male, comprising inducing acrosome reaction in a sample of sperm from the male, detecting at least two different morphological types of acrosome reacted sperm, and calculating a score based on differential weighting of the detected at least two different morphological types of acrosome reacted sperm.

Yet another embodiment is an artificial zona for detecting sperm binding, comprising a solid phase and at least one sperm binding agent comprising a minimum portion of rhZP3 that contains sperm binding site that binds sperm.

DESCRIPTION OF THE FIGURES

FIG. 5 shows the amino acid sequence of the human ZP3 protein (SEQ ID NO: 1).

DETAILED DESCRIPTION OF THE INVENTION

Figure 1:
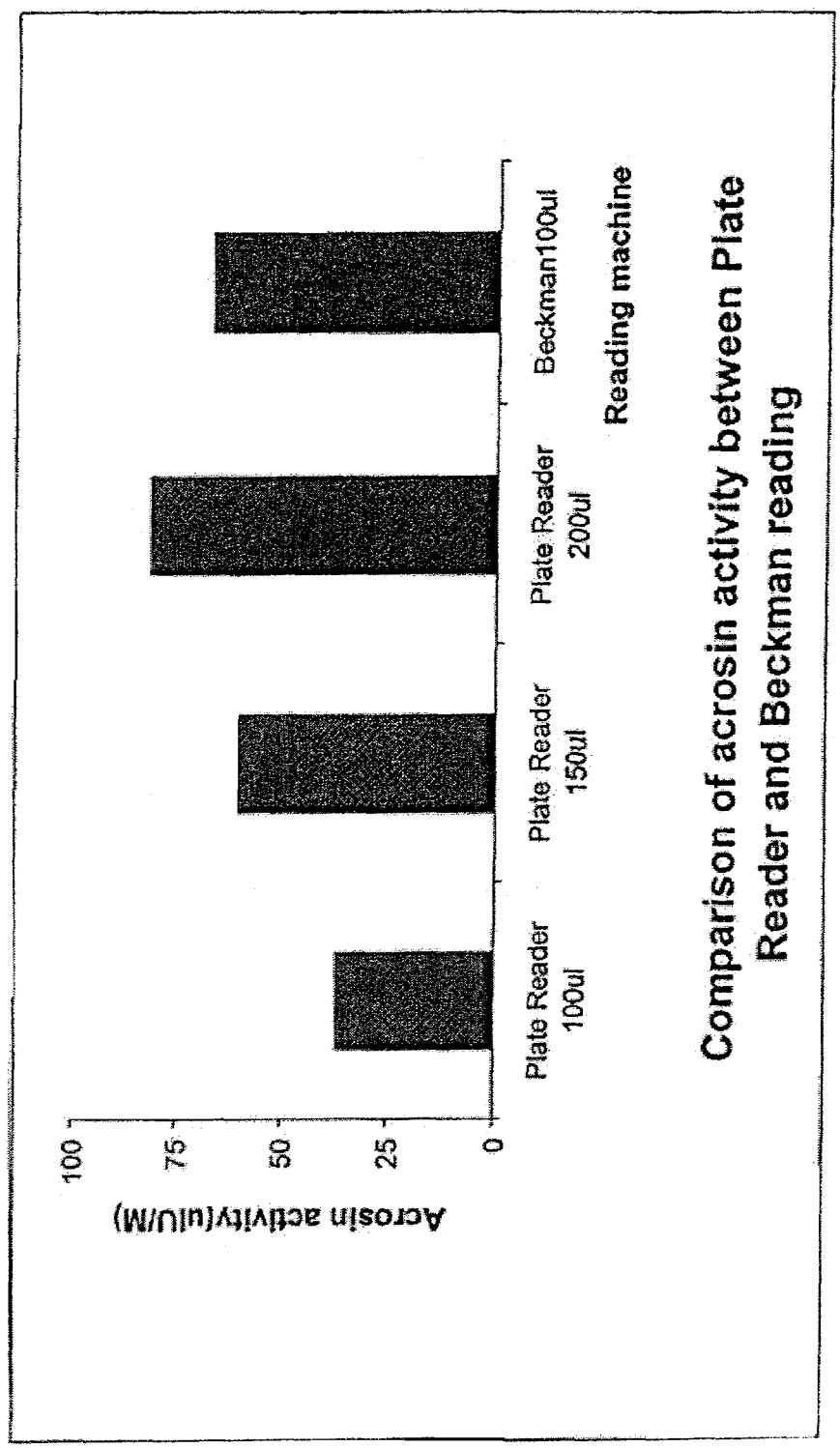
FIG. 1 presents results showing the dose-dependent induction of AR of live sperm in suspension by recombinant human ZP3.
Figure 2:
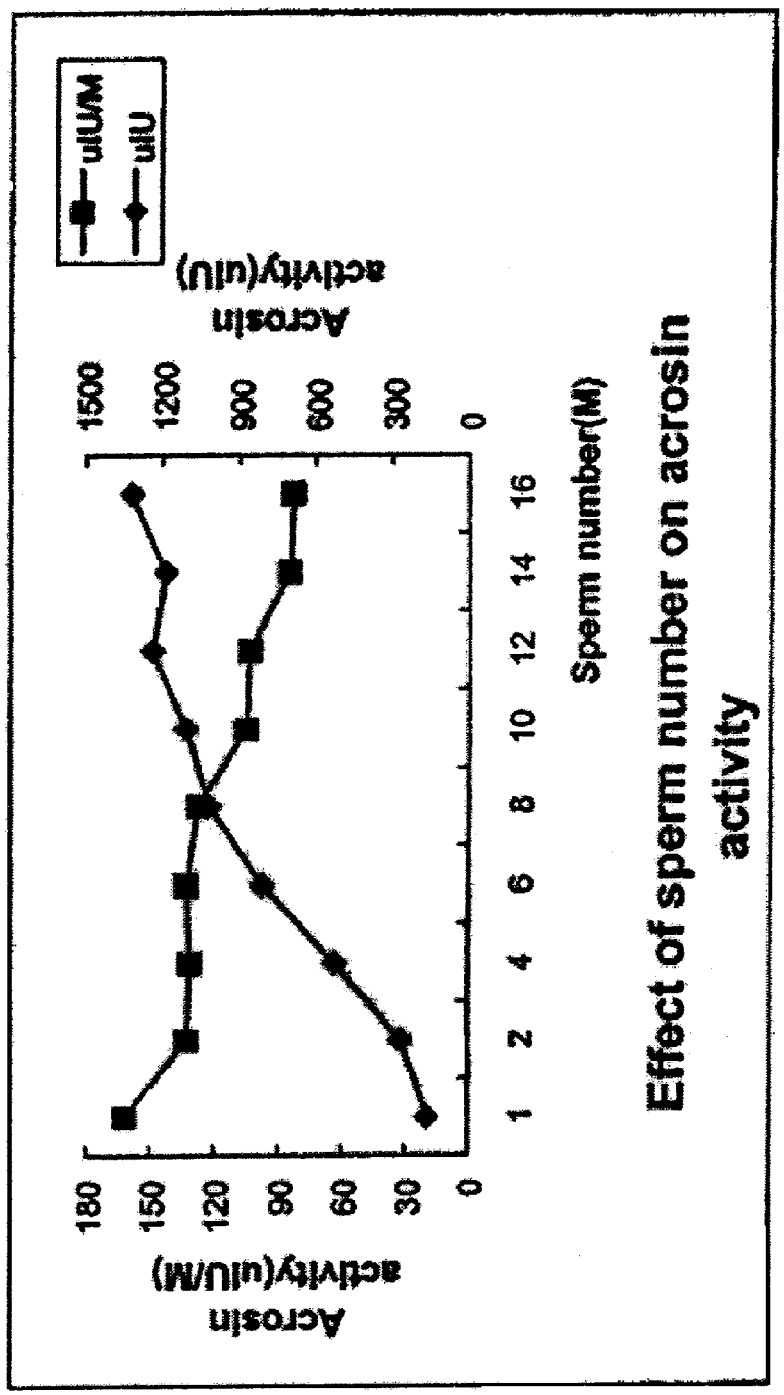
FIG. 2 shows the time course of AR induced by recombinant human ZP3.
Figure 3:
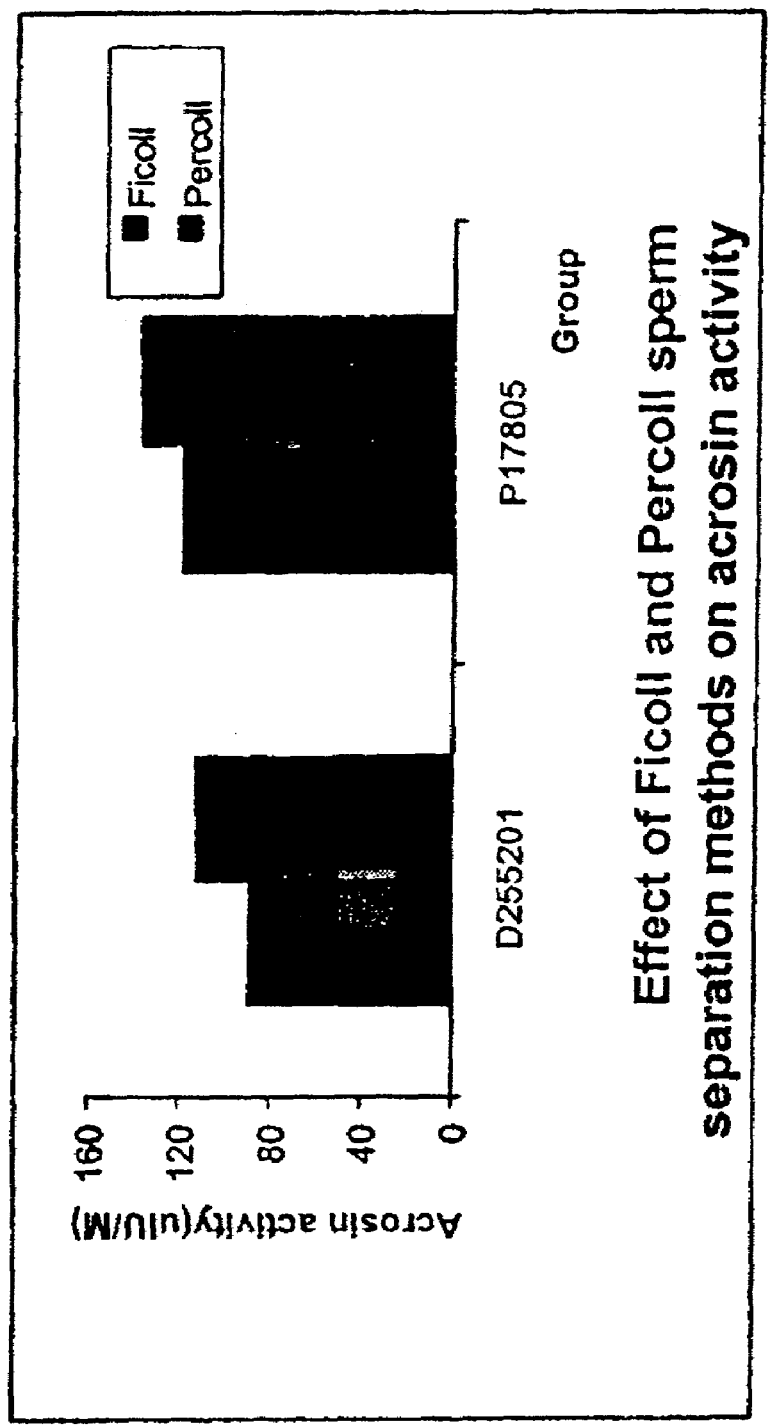
FIG. 3 shows acrosin activity of acrosome reacted human sperm as measured by spectrometry.
Figure 4:
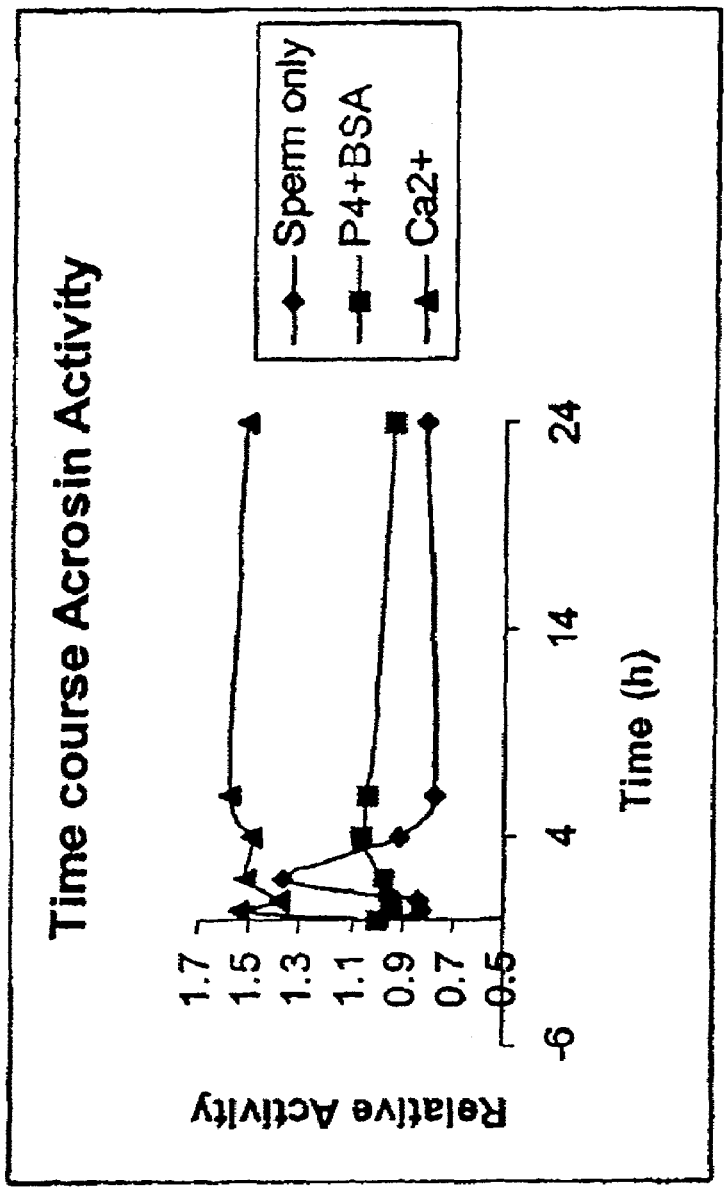
FIG. 4 shows a correlation between calcium ion concentration and the activity of acrosin released from acrosome reacted sperm.

It was found that previously known techniques for assessing sperm performance do not accurately simulate the true in vivo situation and thus suffer inaccuracy. In contrast, a number of discoveries were made that, in many embodiments more faithfully emulate native molecular interactions to yield more accurate and more convenient diagnostic test results. In many embodiments these interactions are coupled to detection systems to provide convenient and rapid assays.

While addressing the above mentioned problems it was found that primary components of a system should be the sperm binding and recognition proteins. Several discoveries were made that pertain to new and improved proteins and methods of their use that more accurately simulate the in vivo system. Other discoveries pertain to the production of these new research and clinical tools, and methods for their use in evaluating sperm function. In particular, several discoveries were made relating to ZP3 and ZP2 biochemistry, cell biology for making higher fidelity ZP3 and ZP2, and related diagnostic technologies that provide more convenient and rapid options for evaluating sperm.

Particularly desirable embodiments of the invention provide more rapid biochemical testing of two diagnostic events in sperm to egg recognition: 1) binding of sperm to zona pellucida protein; and 2) acrosome reaction following the binding. Embodiments allow better separation of test events, better sensitivity of detection and faster quantitation. These embodiments are reviewed in two areas: A) advanced protein agents for male fertility testing; and B) advanced procedures for fertility testing. Particularly desirable embodiments combine one or more advanced protein agents with one or more advanced procedures for more accurate, more convenient and less costly testing. The advanced protein agents also may be used in other fields such as contraception, as will be appreciated upon reading the specification.

A. Advanced Protein Agents for Male Fertility Testing

More correctly glycosylated ZP3 As reviewed by Dong et al., correctly glycosylated ZP3 protein, and particularly recombinant human ZP3 made by a human cell line such as PA-1 (ATCC No. CRL-1572) provides superior selectivity and binding to human sperm. See U.S. application Ser. No. 09/252,828 entitled Recombinant Biologically Active Human Zona Pellucida Protein 3 (hZP 3) to Test Male Fertility and filed Feb. 19, 1999, the contents of which are incorporated by reference in their entireties, particularly details for preparing PA-1 and 293 cells and expressing rhZP3 in those cells as well as alternative procedures that provide a suitable glycosylation pattern of rhZP3 protein and peptides. Procedures were discovered, as detailed below and in the examples, for preparing recombinant human ZP3 as a reagent from cells.

In preferred embodiments the procedures exemplified in U.S. patent application Ser. No. 09/252,828 are followed to prepare recombinant human ZP3 in PA-1 cells. Generally, full-length human ZP3 cDNA or a portion thereof containing an essential glycosylated binding region as described in this patent application may be generated by RT-PCR using mRNA isolated from human ovarian cells. A 1,278 bp DNA fragment (full length of human ZP3 cDNA) or shorter fragment may be obtained after PCR amplification and further characterized by restriction mapping, Southern blot analysis and sequencing of both strands according to a preferred sequence shown in Chamberlin and Dean, 1990 may be used to demonstrate the expression of a 47 kD protein for the full length protein. Most preferably PA-1 is used to produce this protein, as the inventors found that, using antibody against human ZP3, western blot analysis of seven human ovarian cell lines including Caov-3, Caob-4, OVCAR-3, EB2, PA-1, SK-OV-3, and SW626 demonstrated that PA-1 produced rhZP3. Preferably the PA-1 cells or are grown in high density, suspension culture.

In order to obtain high levels of expression of ZP3 in mammalian cells, the ZP3 cDNA preferably is inserted into a pcDNA3.1 vector (Invitrogen, Carlsbad, Calif.) with a strong promoter such as the CMV promoter. To insure biological activity of ZP3, preferably a human ovarian cell is used to express the recombinant ZP3 of seven human ovarian cell lines (EB2, Caov-3, PA-1, Caob-4, OVCAR-3, SK-OV-3, and SW626) from ATCC (Rockville, Md.) and transiently transfected with pcDNA/ZP3 expression construct. Only PA-1 cells exhibited high expression of ZP3 with biological activity and are preferred. Preferably a pcDNA/ZP3 expression construct is transferred into PA-1 cells and treated with neomycin for selection of stable transfection. After, for example, three months of treatment, clones may be selected.

Isolation and purification procedures A wide variety of isolation and purification procedures for ZP3, ZP2, ZP1 as whole proteins, glycosylated fragments, complexes, conjugates and as fusion proteins may be used in embodiments of the invention. Data were obtained that indicate that recombinant human ZP3 prepared by PA-1 cells has superior biological activity and acts as both ligand to sperm and an inducer of the acrosomal reaction. The data show successful demonstration of rhZP3 inhibiting sperm binding in the hemizona assay by dramatically decreasing the hemizona index. Furthermore, data were obtained that establish the ability of rhZP3 to induce the sperm acrosomal reaction. These results clearly demonstrate that the synthesized rhZP3 is a biologically active recombinant ZP3. Each of the techniques most preferably uses a human glycosylated ZP3 and/or ZP2 and/or ZP1.

ZP3, ZP2, ZP1 Complexes, Fragments and Fusion Proteins for Detection

In another embodiment of the invention ZP3 (or an active component thereof) or optionally ZP2, ZP1 or a combination thereof is labeled with a marker such as by conjugation with a readout protein, a colorigenic agent and/or fluorometric agent. The complex is useful for more rapid and convenient test formats to evaluate sperm. In one embodiment a ZP3 or active glycosylated fragment is labeled with a small fluorescent marker and fluorescence is used to qualify or quantify ZP3 that binds to sperm from a sample. In another embodiment ZP3 or active glycosylated fragment is conjugated with another readout protein that generates a visual signal, such as green fluorescent protein.

A related and surprising discovery was that ZP3 continues to properly bind to sperm after ligation to a large protein (GEP) region. In a desirable embodiment ZP3 is coupled to another protein, either chemically in vitro or by expression by a common gene sequence in vivo. In another desirable embodiment, a fragment of hZP3 that contains at least one sperm binding site, including specific glycosylated sties as described in U.S. application Ser. No. 09/252,828 is used either alone or in combination with other proteins, peptides or detection agents. In yet another embodiment the N-terminal conserved region is combined with the sperm binding domain in tandem repeat or fused with one or more epitope tags such as c-Myc, hemagglutinin (Ha), V5, multiple histidines or green fluorescence protein (GFP).

In order to develop commercialized male infertility diagnosis methods, a very sensitive reporter protein, green fluorescence protein (GFP), was fused with rhZP3 (rhZP3/GFP). In various embodiments, the GFP tag provides at least three advantages.

One advantage of these embodiments is that they allow monitoring of GFP-ZP3 expression. With a fluorescent tag, GFP/ZP3 production can be monitored to determine optimum expression conditions from PA-1 cells. Parameters regarding cell passage, growth conditions, seeding density and culture mediums then can be easily acquired and used to produce other recombinant proteins. Furthermore, this information can be applied to protein expression in a bioreactor to produce large quantities of recombinant human ZP3.

Another advantage is the ability to follow OD508 absorbance to locate GFP and evaluate purification enrichment of GFP-ZP3. After establishing a purification scheme, that scheme can be automated for lower costs.

A third advantage is use of labeled ZP3 as part of a sperm binding component. Here, ZP3 or active fragments thereof having a detectable tag can be used as part of sperm binding assay component. With a reporter tag like GFP, the tag itself can be adapted in a sperm-binding assay monitored by flow cytometry or by a fluorescence microscope. Thus, the fusion protein with ZP3 or active fragments thereof can be used to develop diagnosis methods for male infertility. This embodiment is exemplified by the formation and use of ZP3/GFP as described below.

Although a variety of optical tags are used in embodiments, GFP is particularly desirable. The cloning of the wild-type GFP gene (wtGFP; Prasher et al., 1992; Inouye & Tsuji, 1994) and its subsequent expression in heterologous systems (Chalfie et al., 1994; Inouye & Tsuji, 1994; Wang & Hazelrigg, 1994) established GFP as a novel and very useful genetic reporter system. When expressed in either eukaryotic or prokaryotic cells and illuminated by blue or UV light, GFP yields a bright green fluorescence. Detection of ZP3 or ZP3 active glycosylated fragments of GFP and its variants can be performed in living cells and tissues as well as fixed samples. GFP has been expressed as fusions to many proteins. It is desired that chimeric genes encoding either N- or C-terminal fusions to GFP retain the normal biological activity of the heterologous partner, as well as maintaining fluorescent properties similar to native GFP (Wang and Hazelrigg, 1994; Marshall et al., 1995; Stearns, 1995). The use of GFP and its variants provide a "fluorescent tag" on the protein, which allows for in vivo and in vitro localization of the fusion protein. Chimeric bioactive rhZP3 or rhZP3 fragments with green fluorescent protein as well as the use of rhZP2, and/or rhZP1 may be used as described throughout this disclosure for developing diagnosis methods of male infertility.

Desirably, fragments of the ZP3 N-terminal conserved region, and sperm binding domain that bind to sperm are used instead of the whole protein and in fact can give higher potencies (biological effect per unit weight). Fragments comprising at least one binding site region as described in U.S. application Ser. No. 09/252,828 entitled "Recombinant Biologically Active Human Zona Pellucida Protein 3 (hZP 3) to Test Male Fertility" filed : Feb. 19, 1999 are particularly desirable. Most desirably, an active fragment is coupled to a reporter such as GFP. Indeed, it was found that a fusion of ZP3 DNA (5' end) with GFP DNA (3' end) encoded a biologically active fusion protein. To ensure the free rotation of the two proteins, a penta-peptide (Asp-Asp-Asp-Asp-Lys) was used to link the protein portions. This penta-peptide sequence is recognized and cleaved by Enterokinase Max; Invitrogen). The sequence was inserted between the two proteins, which was intended to avoid a possible blocking effect of GFP on the folding of rhZP3 and gives an opportunity for removing the GFP when GFP affects the binding of rhZP3 to human sperm. As glycosylation of the glycoprotein is dependent upon the signal peptide, the signal peptide of human ZP3, with a six-histidine residue at its 3' end was inserted between the CMV promoter and the 3' end of the GFP. This construct was transfected into PA-1 cells, which were treated with neomycin to select for stable transfected cells. After two months selection by neomycin, seven positive clones were selected.

Using the teachings provided herein, recombinant EGFP-ZP3 protein was identified and purified ZP3 obtained. RT-PCR of the mRNA isolated from these clones, with human ZP3's specific primers, displayed high expression levels of human ZP3. ELISA analysis using the monoclonal anti-GFP (Clontech) demonstrated expression of rhZP3 by the cells. Two of the seven positive clones were chosen for subsequent study, as they expressed the highest levels of ZP3 with biological activity. To further identify the recombinant ZP3/GFP, Western Blot analysis was carried out by using two antibodies, an antibody against human ZP3 and a monoclonal antibody against 6×His tag. Western Blot analysis of this protein reveals that it was hybridized with both antibodies and has an expected molecular weight, approximately 90 KD.

Western Blot analysis of the synthesized EGFP-ZP3 was carried out using two antibodies, an antibody against human ZP3 and a monoclonal antibody against Histidine-tag. As described above, a hexahistidine was inserted in the front of the fusion protein sequence for protein purification, allowing use of the affinity column Ni-NTA for protein purification. To facilitate the purification, a Blue Affi-gel is used to remove albumin and protease from culture medium. Then the WGA column is used to catch all glycoprotein from the medium through the Blue gel. The elute from the WGA column was applied to the equilibrated Ni-NTA resin in a batch purification procedure. For a pilot experiment, the concentration of imidazole useful to elute target protein was evaluated. Different concentrations of imidazole were used to elute protein, i.e., 20 mM, 40 mM, 80 mM, 100 mM, 160 mM and 200 mM. With this method, ZP3/GFP was isolated at a 10–30% purity.

The binding activity of fusion protein EGFP/ZP3 was evaluated using flow cytometry. Flow cytometry can quantitate components or structural features of cells primarily by optical means. Although it makes measurements on one cell at a time, this method can process thousands of cells in a fluid stream passing through the path of laser beams in a few seconds. Since different cell types can be distinguished by quantitative structural features, flow cytometry can be used to count a large population of different cell types in a mixture. Data were obtained showing that when EGFP/ZP3 bound to human spermatozoa, via true binding, after washing the treated sample, the fusion protein could still bind to the receptor on the sperm plasma membrane. When these samples were analyzed by flow cytometry, the number of spermatozoa binding with EGFP/ZP3 were counted and the percentage of binding cells assessed. The data indicated that approximately 60% of the human spermatozoa bound to rhZP3/GFP with 3 hours capacitation. After washing, 30–40% of human spermatozoa remained bound to rhZP3/GFP, indicating specific binding. Such specific binding increased following increased capacitation time from 3 to 4 hours. In contrast, human spermatozoa did not bind to GFP itself (5 ug, 10 time higher concentration than that of rhZP3/GFP).

The specific embodiments outlined above may be carried out a variety of ways as the skilled artisan will readily appreciate. Example 11 further exemplifies the purification of rhZP3/GFP and uses an assay that detects biological binding activity to determine that the fusion protein made works. In an advantageous embodiment, the protein described in Example 11 is further purified by FPLC. Alternatively, in order to reach a higher purity of rhZP3/GFP or other conjugate or fusion protein an immunoaffinity chromatography may be employed. The latter example describes an embodiment of preparing and using immunoaffinity separation.

ZP2–ZP3 complexes Coupling of ZP2 with ZP3 provides even more accurate, sensitive and convenient tests for determining causes of male infertility in embodiments of the invention. Methods were discovered for the synthesis of ZP2–ZP3 complexes and their use. The conjugates may be formed either covalently or non-covalently and optionally in the form of filaments. Such complexes are also useful as contraceptives either alone or in combination with other agents. In these embodiments ZP2/ZP3 complexes are provided in a solution form, coated on a solid surface such as a latex surface, a jelly, or other dispersion, preferably in amounts (per individual dose) of at least 10 ug, 100 ug, 1 mg, 10 mg or even more than 100 mg.

In a particularly desirable embodiment a ZP2–ZP3 complex protein can be prepared in at least three ways. In a first way the complex is constructed by forming the proteins, or portions thereof separately. The proteins (or portions) are denatured, mixed together and renatured to form complexes that have activities of both ZP3 and ZP2. In a second way, a nucleic acid is formed that encodes both proteins (or portions of one or both proteins) and is expressed to make a hybrid protein, having desirable activity. In a third way, vectors that separately encode the two proteins (or portion(s) thereof) co-express in a common host cell the two proteins, which may assemble (preferably) inside the host cell or outside the host cell. In yet another embodiment a vector is prepared and used that expresses both proteins as separate polypeptides from a single DNA. In many embodiments ZP1, ZP2 and ZP3 are human forms of ZP protein. However, non-human sequences may be used in many cases. For example non-human ZP2 and/or ZP1 may be complexed with human recombinant ZP3.

In yet another embodiment ZP1 protein is used to cross link ZP2/ZP3 into complexes formed from the three proteins. This embodiment may be carried out by forming filaments of ZP2/ZP3 and then adding ZP1, (preferably recombinant ZP1 that optionally may be made by a prokaryote or a low cost eukaryotic system such as yeast) or the ZP1 may be added before or during formation of ZP2/ZP3 strands. In a desirable embodiment genes for ZP1, ZP2 and ZP3 are co-expressed in a host cell and the complexes recovered from the cell. In an advantageous embodiment however, ZP2–ZP3 strands are formed and then ZP1 is added in vitro to form the complexes. In the future further optimized synthesis procedures for preparing ZP2/ZP3 strands will be discovered. The combined incorporation of ZP1 into these complexes is contemplated as well for some embodiments of the invention.

Complexes of rhZP2 with rhZP3 are especially desirable for many embodiments of the invention and allow greatly superior binding. Without wishing to be bound by any one theory of this embodiment of the invention, it is thought that, compared to primary binding, secondary binding is a stronger, irreversible and persistent binding because the secondary binding is mediated by proacrosin/acrosin on the inner acrosomal membrane and the ZP2 in the zona pellucida (Hyne et al., 1984; Yanagimachi, 1981). ZP2 by itself, however, cannot bind to acrosome intact spermatozoa because without acrosome reaction the inner acrosome membrane will not be exposed. An immunofluorescent study indicated that rhZP2 bound only to acrosome-reacted spermatozoa (Tsubamoto et al., 1999). Therefore, rhZP2/rhZP3 protein complexes possess the ability for both acrosome reaction induction and secondary binding. In embodiments of the invention, such complexes bind and hold spermatozoa on beads.

Most preferably two types of rhZP2/rhZP3 protein complexes are constructed. In a first type, recombinant human ZP2 (rhZP2)- recombinant human ZP3 (rhZP3) filament is made, either by integrating purified rhZP2 and rhZP3 together by denaturing followed by glutathione mediated re-folding, or by co expression of rhZP2 and rhZP3 in the same cells as outlined herein. In a second type, rhZP2–ZP3 fusion proteins are generated by fusion. In this case the hZP2 cDNA and hZP3 cDNA more efficiently utilize their function domains. Materials for embodiments of the invention such as sperm binding agents and artificial zona preferably comprise at least some of either type or even both types. Such materials yield stronger and more correct binding to sperm. Without wishing to be bound by any one theory for this embodiment of the invention, it is thought that such protein-constructions more closely mimic the natural ZP2–ZP3 filament. In yet another embodiment, such complexes further include ZP1. It further is noted that ZP2 and/or ZP1 optionally may have sequences and/or glycosylation patterns from species other than human, although human proteins are preferred generally.

It was found that purity of the prepared reagent protein is important in some embodiments. Preferably a purification system is used that combines Sepharose Q ion-exchange and nickel-histidine or cobalt-histidine mediate affinity chromatography to isolate and purify rhZP2 and rhZP2–rhZP3 fusion proteins. Sepharose Q ion-exchange chromatography is particularly desirable for initial target protein isolation and to reduce the volume of protein sample. Metal-poly-histidine mediated chromatography is highly desired in embodiments and provides a stronger metal-poly-histidine binding with minimum hydrophobic interactions, as can be determined by a skilled artisan. Also preferred is the use of a partial denaturation with urea to establish a stronger metal-polyhistidine binding by completely exposing the polyhistidine tag of rhZP2. With a stronger metal-polyhistidine binding, a stronger washing condition is applied to remove the co-purified proteins, which associate with the resin by forming non-specific interaction between metal and non-poly-histidine. Also preferred is the use of non-ionic detergents such as Tween-20 and NP-40 to remove proteins that associate with resins by non-specific hydrophobic interaction. Still further, urea mediated denaturing purification can be used for purification and is yet another embodiment of the invention. In the latter case, rhZP2 and rhZP2–rhZP3 fusion proteins purified under denaturing conditions can be renatured using oxidizing and reducing thiol agents such as glutathione (Patra et al., 2000) to restore their native structure. Example 19 describes a representative set of conditions for this embodiment of the invention.

B. Advanced Procedures for Male Infertility Tests

New advanced procedures were discovered for more accurate detection of disorders such as sperm defects. Many embodiments employ steps or treatments that more closely approximate or replicate the in vivo conditions that occur during sperm to egg recognition. Without wishing to be bound by any one theory of this embodiment of the invention it is believed that accuracy problems in previous methods for assaying male infertility were caused by lack of one or more very important biochemical agents or conditions found in the in vivo situation. In a desirable embodiment a more suitably glycosylated ZP3 is prepared and used as a reagent that binds sperm with higher specificity compared with previous reagents, thus improving both sensitivity and accuracy, and allows more rapid and more convenient advanced procedures that exploit the binding between sperm (or a sperm component) and ZP3 or ZP3/ZP2 or ZP3/ZP2/ZP1. A host cell type further was found that provides unexpectedly high production of ZP3 and is particularly desired. Still further, cell culture conditions were discovered that provide further improvements to the ZP3 protein by making the protein more similar to the in vivo protein, and which provide more accurate procedures. In desirable embodiments, of the invention cell type (uterogenital origin and mammary gland originated cell types) are particularly preferred for generating more suitable amounts and/or types of protein described herein. Also preferred are the use of low serum, low glucose medium, high density culture, and differentiated cells for generating higher amounts and/or quality of recombinant protein.

Many of the embodiments can be categorized into two types of procedures for appraising male infertility: 1) binding reactions with ZP3, ZP3/ZP2 or ZP3/ZP2/ZP1; and 2) acrosome enzyme (e.g., acrosin) release detection from activated sperm samples. In yet another embodiment, a ZP3 binding test result is combined with an AR test result in a profile that provides enhanced accuracy compared with present tests that report morphology changes. Without wishing to be bound by any one theory of this embodiment of the invention it is thought that the initial sperm to egg interaction leading to fertilization can be split into two steps, a recognition/binding step and an acrosomal release step. Detecting one or both of these steps using biochemical procedures was found to provide not only more accurate clinical results, but also faster and more convenient, and generally lower cost diagnostic methodologies as well. In most preferred embodiments such biochemical tests use one or more advanced materials described above, which further improves test results.

Binding Reactions Potentially rapid and convenient binding assays and improvements to them were discovered through exploitation of the biochemical mechanisms associated with the sperm and egg interaction. Most important in this context is the use of at least part of the ZP3 protein having an oocyte like glycosylation pattern. The phrase "at least part of" in this context means, as a minimum, the carboxyl terminal glycosylated region of ZP3, optionally as part of a larger protein and/or protein complex. In a desirable embodiment an entire human ZP3 protein is made recombinantly in a human ovarian cell line such as PA-1. The ZP3 protein may be extracted, partially purified or purified and then coated onto the solid phase by any of a number of techniques known in the art, such as those that employ covalent coupling to amino, carboxyl, or sulphydral groups of the protein, or non-covalent coupling. The ZP3 may be attached to a wide variety of solid phases may be used such as for example, paramagnetic particles, polystyrene particles, gold sol particles, selenium particles, latex, polystyrene beads, other plastic beads, sieves or membranes, plastic, glass or metal walls and the like. Typically the solid phase is washed after the coupling step.

During use, prepared sperm typically are incubated in liquid suspension with the coated solid phase and binding between sperm and the solid phase assayed. A wide variety of assay techniques are known or can be derived, based sometimes on the acrosome reaction that occurs and that spills components out of the sperm. In one embodiment however, the binding reactions and their detection occurs first at a cold temperature and the AR occurs later at a warmer temperature. The two events also can be separated chemically, using chemicals that stabilize the sperm membranes as desired to block the AR without blocking the binding reaction.

In yet other embodiments ZP3, ZP3/ZP2 complex or portions thereof are immobilized on a solid phase and contacted with extracted molecules from a sperm sample. For example, as knowledge of specific defects in sperm progresses, it will be desirable to determine binding or the presence of known allelic forms of proteins. While many such investigations can be carried out by probing DNA sequences, in some cases direct binding of (for example) sperm membrane protein to ZP3; ZP3/ZP2; or ZP3/ZP2/ZP1 may reveal still finer qualitative details of sperm samples. Example 16 shows a representative coupling of GFP-rhZP3 to carboxylate modified microspheres and rhZP2 to carboxylate modified microspheres according to an embodiment of the invention.

Artificial Zona A solid phase bead based binding assay is particularly advantageous in alleviating the complexities and attendant need for skilled personnel required in the hemizona assay test for predicting fertilizing capacity. Not only does a ZP3 or ZP3 conjugate coated bead test eliminate the need for skilled technical labor but such method was found to eliminate the need for using human zona pellucida, which is difficult to obtain, preserve and transport. During experimentation, it was found that a fluorescent labeled ZP3 or ZP3 binding site region coated solid phase advantageously may be used in a simple, yet rapid and sensitive test. A GFP-rhZP3 fusion protein was used to coat beads, and the coated beads mimicked the sperm binding function of the native zona pellucida and allowed the discrimination of spermatozoa with normal from spermatozoa having abnormal zona pellucida binding ability.

Coated particles according to this embodiment of the invention are analogous to zona and are termed "artificial zona" for convenience. It was found that GFP-rhZP3 coated agarose beads act as artificial zona for diagnostic purposes because they bind sperm. The quality of binding reveals sperm binding abnormalities in a synthetic system and can predict the fertilizing capacity of spermatozoa in the in vitro fertilization system.

An artificial zona comprises at least 1) a solid phase such as a bead, particle or other surface; and 2) attached thereto, a minimum portion of rhZP3 that contains sperm binding site that binds sperm. The minimal portion of ZP3 that has the capability of binding to human sperm arises from two binding sites on the ZP3. One site is a sugar-motif on the sperm binding domain (before the furin cleavage site) and another is an N-terminal conserved region that follows the signal peptide (25 to 50 amino acids). The sperm binding domain is determined from Wassarman's site—directly mutagenesis. The N-conserved region is based on phage display assay and on the use of computer programs that determine the region of ZP3 under selection pressure.

In this same context, and without wishing to be bound by any one theory for this embodiment of the invention, it is thought that ZP3 can be divided into the following generally contiguous domains from the amino terminus to the carboxyl terminus: the signal peptide (1–22)- short N-stretch (another sperm binding site) a—ZP domain—sperm binding domain-furin cleavage site and the transmembrane domain. In one embodiment a minimal glycosylated ZP3 is used that comprises the N-terminal conserved region, and sperm binding domain in tandem repeats or optionally fused with epitope tags such as c-Myc, Ha, V5, histidines and GFP.

A solid phase for the artificial zona reagent and test method can be made from any of a variety of materials such as latex particles (typically between 0.05 and 2000 microns in diameter), paramagnetic particles such as ferric oxide or chromium dioxide, gel particles such as agarose, Sephadex, acrylamide, polystyrene, silicon, nitrocellulose surfaces, gold particles or flat surfaces, glass particles or flat surfaces, and the like. Most preferably the solid phase is coated with purified recombinant GFP-rhZP3 fusion protein and materials, such as agarose, polystyrene and silicon are preferred to increase conjugation efficiency and to decrease non-specific sperm binding.

In advantageous embodiments, bead sizes and/or textures approximate that of a human egg, which is about 100 μm in diameter with about a 7~10 μm thickness zona with gel-like property. In a preferred embodiment agarose based beads the size of an egg (10 to 2000 microns in diameter, preferably 20 to 1000 microns, more preferably 35 to 500 microns and even more preferably 50 to 250 microns in diameter) are prepared to compare a "Hemi-zonal index (HZI)" with an "artificial zona index (AZI). In another embodiment, fluorescent micro-beads are prepared having limited drag forces and which can easily be quantified by cytometry or fluorometry, and that are well suited for use in automatic assay methods. In another cases, beads are made having other modifications such as magnetic particles with beads, which advantageously allow separation of bead-bound spermatozoa from free spermatozoa.

In a particularly desirable embodiment the solid phase is not an incompressible/hard solid but rather is soft and compressible. In a desirable embodiment the softness (compressibility in response to applied liquid pressure) is between the hardness of highly cross linked acrylamide 100 micron particles and 100 micron sized Sephadex G-300 particles. In another embodiment the softness is intermediate between that of Sephadex G-5 and Sephadex G300. In a related embodiment the particle surface is flexible enough to allow multiple binding of sperm binding sites over at least 2%, 5%, 10%, 15%, 20%, and even over 25% of the sperm surface. Particularly advantageous are artificial zona that are soft, as described here and which contain ZP3 tethered to the surface by ZP2 or other linker, allowing greater interaction between sperm and multiple binding sites on the artificial zona.

Example 17 illustrates two alternative conjugations to agarose beads, which simulate zona properties. It was found that chemical coupling gives better artificial zona. Furthermore, it was found that zona and other reagents made from GFP-rhZP3 are superior to those made from rhZP3.

As shown in Example 18, the binding conditions between artificial zona and sperm were examined by, for example, changing buffer components and by supplementing the system with ZP2 protein. Without wishing to be bound by any one theory of this embodiment of the invention, it is hypothesized that besides bioactive ZP3, the native zona pellucida and artificial produce GFP-rhZP3 coated bead share no other common components. Thus, the proper sperm binding condition for GFP-rhZP3 coated beads do not necessarily follow from that seen in the in vivo situation. Accordingly, advantageous parameters were examined and can be further examined, using the procedures shown in Example 18.

For optimizing binding condition with GFP-rhZP3 coated beads, both sperm quality and sperm binding conditions are considered and optimized in routine procedures for each type of application. In this regard, it is well known that sperm-zona interaction is dependent on sperm capacitation time. When incubated with bioactive ZP3, the binding property of sperm becomes lost due to the sperm acrosome reaction. Accordingly, both incubation time and sperm concentration are to be optimized by routine study, using the procedures described herein, and advantageously are tested using GFP-rhZP3 mediated sperm binding. Advantageously an acrosome reaction blocker is included in the binding condition. Solubilized human zona pellucida is used as a competitive reagent to study the specificity of GFP-rhZP3 for human spermatozoa binding. The hemizona assay is used as a parallel control to evaluate the sperm binding ability of GFP-rhZP3.

Generally, although GFP-rhZP3 was used in many embodiments described herein, the ZP3 binding site that is capable of binding to sperm and which is affixed to the particle or other solid phase surface may be any relevant part of the glycosylated ZP3 protein, peptide or fusion protein. In many embodiments the entire glycosylated ZP3 protein may be used for convenience. In other embodiments both ZP3 and ZP2 are bound to the solid phase surface and in yet other embodiments ZP1, ZP2 and ZP3 are bound. In another embodiment the solid phase is a particle that has ZP1, ZP2 and ZP3 layered on the surfaces, as may be accomplished by a skilled artisan in this field. In another embodiment, the particles themselves are primarily (at least 50%, 75%, 85%, 90% 90% or even 95%) comprised of protein (such as ZP3, ZP2 and/or ZP1) complexed together into large aggregates.

In a very desirable embodiment the preferred GFP-ZP3 conjugates are prepared as described herein and used as described in Example 7. In this example, ZP3 fusion protein labeled agarose beads successfully acted as artificial zona and allowed the use of a simple in vitro test to replace the standard expensive and difficult to carry out zona pellucida test. Example 8 illustrates the formation of recombinant ZP2 used for this and other embodiments of the invention.

Easy/Rapid Methods to Detect Biological Activity of Purified Protein

Presently, the binding of ZP3 to sperm is determined indirectly by its effect of blocking the binding of sperm to hemizona. Desirable embodiments of the invention, on the other hand, improve over these procedures by direct binding of a zona pellucida protein, fragment, conjugate or fusion protein to the surface of capacitated and acrosome intact sperm. Such technology, using one or more of the protein reagents described above, relies on the more rapid binding kinetics, typically between sperm binding regions of rhZP3 and sperm to make a more rapid and, in many cases, more accurate clinical diagnosis method for male infertility. In many embodiments entire rhZP3 protein, optionally conjugated or fused with other molecules such as ZP2, ZP1 and convenient detection label is preferably used.

Embodiments of these methods also employ flow cytometry for quantifying components or structural features of cells primarily by optical means. Although generally flow cytometry makes simple measurements, it can process thousands of cells in a fluid stream passing through the path of laser beams in a few seconds. Furthermore, different cell types can be distinguished by quantifying structural features. Thus, flow cytometry can count a large population of single cells of different types in a mixture.

It was discovered through ongoing experiments that when EGFP/ZP3 binds to human spermatozoa with true biospecific binding, the fusion protein remains bound to the receptor on the sperm plasma membrane after washing. In a desirable embodiment, after analyzing the sample with flow cytometry, the numbers of spermatozoa binding with EGFP/ZP3 are counted and the percentage of binding cells are assessed. The purified protein is used for a binding study.

Sperm used in such procedures typically are motile sperm selected by the "swim-up" procedure. In a desirable embodiment, semen analysis using, for example, the Hamilton-Thorn Research Sperm Analyzer is performed first to evaluate sperm motion parameters. Semen from normal donors are evaluated by national standards, divided into groups of 0.5 ml aliquots, and each aliquot washed (for example, twice with two volumes of HTF medium supplemented with 0.5% human serum albumin). Motion analysis then is carried out after a time such as after a 1-hour swim-up. In general, a minimum motility of, for example, 70% is obtained.

After the swim-up (if used), sperm samples are allowed to capacitate under suitable conditions such as, for example, 37° C. in 5% $CO_2$ for 1 hour (Oehninger et al, 1991). The sperm samples then are incubated with a desired protein, protein fragment containing a sperm binding site, conjugate or fusion protein, such as rhZP3/GFP for an additional time such as 2 hours. The incubated samples are washed (for example, with PBS twice) to remove non-specifically bound material. The specific binding is detected by any procedure useful to detect binding reactions to solid surfaces. Most preferred is the use of flow cytometry. In the case of using ZP3/GFP, the GFP vector without the ZP3 insertion is stably-transfected into PA-1 cells. The protein sample isolated from these cells may be used as a negative control.

In another embodiment, natural solubilized human ZP3 obtained from human oocytes is used to compete with a green fluorescent protein conjugated rhZP3 for sperm binding. The solubilized ZP3 in this case competes with labeled-rhZP3 for binding sites on the sperm surface thereby decreasing the number and intensity of fluorescence on the sperm cells. Data are analyzed for statistical of distribution and by student's t-test or ANOVA (with correction for multiple comparisons and repeated measures) as appropriate.

Acrosin Release Detection It was found that a more reliable and convenient method for detecting male infertility problems could be made by assaying one or more substances released during the acrosin reaction. In many of these embodiments the released substance comprises one or more molecules such as an enzyme, protein, membrane fragment, phospholipid, cholesterol, peptide, lipoprotein, nucleotide, nucleoside and glycoprotein, which are released during the acrosome reaction. In an embodiment released fragments of membranes are detected. Measurement of any of the released substances during or after acrosome reaction indicates the progression of an acrosome reaction. In a desirable embodiment two substances are detected and the amounts of each are statistically weighted, using factors that a skilled artisan may determine, to obtain a more reliable overall measurement. In yet another embodiment one or more released substances at detected at two times, before and after the acrosome reaction. In another embodiment released substances are detected at three or more different time points.

In a particularly desirable embodiment, acrosin assay sensitivity is increased by using an alternative substrate for a trypsin-like enzyme. In this embodiment Rhodamine-110 (from Molecular Probes) provided ten fold increased sensitivity over the use of substrate BAPNA. This substrate itself has no fluorescence but when cleaved by a trypsin-like enzyme, generates a fluorescent product. In another embodiment, it was found that increasing ZP3 purity, particularly beyond 75%, 80%, 85%, 90%, 95% and even above 98% provides more reliable acrosin assay results. Specific techniques described herein, individually and in combination, such as ion-exchange, 6×-histidine affinity column, immunoaffinity column and hydrophobic interaction chromatography are particularly desirable for improving purity to above 80% and can give improved method results.

Advantageously such acrosome assay using highly purified rhZP3 can replace the complicated and time-consuming acrosome reaction detection method in determining sperm acrosome reaction level. In one embodiment of a method, sample sperm are incubated with purified rhZP3 and if the acrosin activity from the supernatant is close to that of the untreated sperm group, then this indicates that the sperm donor (typically a fertility patient) has a problem of non-induction of acrosome reaction by bioactive ZP3. On the other hand, if the acrosin activity from rhZP3 treated group is significantly higher than that from an untreated group, then the patient is normal in this aspect of sperm function.

Example 1 describes an easy to carry out acrosin reaction that uses optical density changes that occur after binding and the ensuing acrosin reaction. In preferred embodiments, acrosin reaction is assayed by setting up incubation conditions up to formation of a pellet and supernatant, as exemplified in example 1, but using a more sensitive detection system. A highly desirable embodiment in this context utilizes an ELISA-type of assay. In this embodiment a sample may be divided into two portions. One portion is analyzed based on sperm number; and the other based quality of biochemistry. For example proteins may be immobilized on surfaces such as in wells. Examples of proteins include lectin (WGA and PSA), anti-sperm surface protein or ZP3 to detect acrosome intact sperms. Desirably an acrosome reaction blocker may be included as needed. Further reagents useful for this embodiment may include anti-CD46, SBTI (soybean trypsin inhibitor), ZP2, and anti-acrosin to detect the acrosome lost sperm. After washing, the sperm may be simply counted inside the well or another procedure used such as application of a DNA dye to quantify sperm number and thereby determine the number of acrosome intact sperm (AI) and acrosome lost (AL) sperm. Preferably an acrosome reaction value is measured as a % value and is equal to AL/(AI+AL).

In a further embodiment released substance may be detected specifically, and preferably immunochemically, for example, with one, (more preferably two) or more anti-acrosin antibodies to qualify the amount of acrosin released in supernatant after induction of the acrosome reaction. An acrosin antibody can be replaced or supplemented with an antibody against alkaline phosphatase, or against another enzyme or biomolecule from the acrosome. Alternatively, a binding agent (such as an antibody) specific for a phospholipid such as an anti-phosphotidyl-serine, or anti-phosphotidyl-inositol phospholipid may be used to detect released components of the plasma membrane itself.

Acrosome scoring system Acrosin accounts for almost 20% of the total acrosomal protein. Unfortunately however, there is no generally reliable assay method using acrosin activity as an indicator of AR. A complication in this regard was found to be the presence of acrosin inhibitors. The antitryptic activity of acrosin arises from the human seminal plasma inhibitors (HUSI) I and II (E. Fink, et. Al, 1971), (H. Schiessler, et al, 1974). Both inhibitors greatly interfere with acrosin activity. Despite the problems, the "photometric enzyme method" has been used to assay acrosin. Generally, according to this method, a sperm sample is treated with triton X-100 for lysis followed by conversion of proacrosin to acrosin. Although this method can measure total amount of acrosin activity, the measured value generally is not very accurate. Thus the test is not suitable to detect acrosome reaction of human sperm.

A new method was discovered based on the fact that the acrosome reaction is a progressive phenomenon. That is, several morphological changes take place when spermatozoa acrosomes react. It was found that merely determining the percentage of acrosome reacted spermatozoa to monitor the acrosome reaction did not adequately reveal the course of the acrosome reactin. Furthermore, an acrosome scoring system was found that measures continuously the changing morphology during AR. This scoring system was used and compared with a previous system of measuring the percentage of reacted and/or unreacted acrosomes. The acrosome scoring method was found to provide more correct clinical results.

According to an embodiment at least two different morphologies, or observed spermatozoa "types" are quantitated and different weighting given to counts of spermatozoa exhibiting the morphologies. In another embodiment at least three different morphologies are quantitated and different weighting given. In another embodiment at least four different morphologies are quantitated. In yet another embodiment at least 5, 10 or more different morphologies are quantitated. The identification or quantitation of individual spermatozoa conveniently may be carried out by microscope visualization after, for example staining. More conveniently the process may be automated with a solid state imaging device and software that recognizes the types and automatically counts spermatozoa in different types. Example 4 demonstrates a representative set of conditions and results for carrying out this embodiment of the invention.

Assay by binding of High Quality Reagent to sperm: Example using ZFP/ZP3 Embodiments of the invention include methods that rely on direct binding of one or more "High Quality Reagent" (properly glycosylated peptide or protein corresponding to at least the amino terminal end of ZP2, optionally complexed with another protein or readout chemistry) to sperm. This embodiment is made possible high quality properly glycosylated binding region of ZP3. Accordingly partial or whole ZP3, ZP3/ZP2 complex, ZP3/ZP2/ZP1 complex, ZP2-protein such as ZP3/GFP and other complexes optionally with detection reagents may be used to determine male infertility by direct binding. Many embodiments require a three step procedure. One, a high quality protein reagent is provided (e.g. synthesized or purchased). Two, the reagent is incubated with prepared sperm. Three, the portion of reagent bound to sperm is detected after an optional wash. Detection typically is carried out by fluorometric or other optical assay.

This embodiment was exemplified with ZP3/GFP. ZP3/GFP prepared as described herein was used successfully for binding tests. The motile sperm samples were incubated with GFP/ZP3 for different time periods. The binding of sperm and GFP/ZP3 was measured after one, two and three hours of incubation. After purification, the concentration of fusion protein was expressed as the amount of GFP in the protein sample ([GFP] per batch of fusion protein). In a desirable protocol, GFP only was used as negative control, for GFP only and fusion protein treated sperm sample, GFP concentration was normalized to be the same (final 5 µg/ml of GFP), GFP only should show no binding, on the other hand, GFP/ZP3 show binding with sperm. After one hour about 23% of sperm showed fluorescence. After 2 hours about 28% showed fluorescence and after 3 hours about 42% of sperm showed fluorescence. Incubation with the fusion protein alone showed sperm binding, whereas GFP alone showed no binding. As the incubation period increased the percentage of binding sperm increased, indicating a time dependency for human sperm binding with the fusion protein.

Dose dependency of High Quality Reagent binding to sperm: Example of GFP/ZP3 GFP/ZP3 was found to bind to sperm in a dose dependency relationship and is particularly useful as a reagent in many embodiments. A desirable concentration range for using this conjugate typically is from 1 ng/ml to 10 mg/ml, more preferably 100 ng/ml to 100 ug/ml and in some embodiments from 1 to 15 ug/ml. For example, in order to determine how the concentration of fusion protein affect the binding of sperm with one batch of GFP/ZP3, a dose dependency assay was set up. The percent sperm showing fluorescence from FACS was assayed for a dose test of 1.0, 2.0, 3.0, 4.0, 5.0, 7.5, and 10.0, 12.5 µg/ml fusion protein. The data showed a dose response for sperm binding with GFP/ZP3. The sperm binding increased with the increase of fusion protein concentration, and the binding curve started to level off at around 5 µg/ml of fusion protein GFP/ZP3. Other reagents for binding may be used at similar concentration and conditions and can be determined by routine optimization.

Enterokinase digestion to assay sperm binding Enterokinase digestion is useful to study the quality of prepared high quality reagent such as GFP/ZP3 and for diagnostic methods of assay for sperm binding. An important feature of embodiments of the invention is to detect binding of recombinant ZP3 to human sperm as true biological binding and not a result from an artificial cause such as another co-purified protein that facilitates binding of recombinant GFP/ZP3 to the human sperm surface. In one embodiment, enterokinase from Enterokinase Max is used to digest purified fusion protein GFP/ZP3.

A wide range of digestion conditions may be used as will be appreciated by a skilled artisan. In one pilot study for example, a series of different units of enzyme were used in the digestion and the digestion was completed in a 37° C. water bath. Meanwhile, another sample with the same amount of protein but with no enzyme added was used as a control to see if some protease acts at 37° C. to cleave fusion protein. Western blot using ZP3 antibody was carried out to verify the efficiency of protein digestion. In Western Blot, besides all digestion protein samples, one sample with original undigested protein was used as a control to determine if fusion protein has been fully digested. The undigested and digested proteins were used for the sperm binding test. The digested protein resulted in a decrease in sperm binding, complete digestion of fusion protein resulted in almost no sperm binding; furthermore, low dosage of enzyme resulted in incomplete digestion of fusion protein, and there were still about 20% sperm showing binding. These data indicated that the sperm binding analyzed by FACS is a ZP3 mediated phenomenon. There was a dose dependency relation between dose of enterokinase used and the sperm-binding outcome.

In one embodiment, two doses of enterokinase are used in digestion to determine a dose effect on fusion protein digestion and from that, to derive sperm binding. This embodiment is exemplified in Example 10, which used western blot with ZP3 antibody. Under the conditions used in that example, 1U of enterokinase completely cleaved GFP from the fusion protein, which decreased sperm binding to 10%, while the undigested protein showed 53.6% sperm binding. For a 0.5U enterokinase digested protein sample, about 60% GFP was digested from the fusion protein, and the corresponding treated sperm sample showed 20% sperm binding. Each different type of reagent may be similarly optimized based on its specific chemical characteristics and the teachings provided herein.

In a set of experiments, enzyme digestion was repeated four times and sperm binding was tested by flow cytometry. The digested fusion protein showed a dramatic decrease of sperm binding in the test. There was some non-specific signal detected in the digested fusion protein sample when analyzed by flow cytometry. The dose of GFP/ZP3 in this test was 5 µg/ml, GFP (5 µg/ml) only and NT (non transfected)+GFP were set as negative control. Sperm treated with GFP/ZP3 resulted in 50.02±4.51% binding, whereas GFP only and NT+GFP did not show any binding.

Immunofluorescence to assay sperm binding As an alternative approach, immunofluorescence may be performed to directly visualize sperm binding with ZP3 conjugated to a fluor such as GFP, Alexa 448 or fluorescein or with ZP3/ZP2 conjugated to such kind of fluor. In this embodiment typically the conjugate such as a fusion protein is incubated with sperm. To improve sensitivity and convenience immunofluorescence may be used for amplifying the optical signal through the application of an antibody directed against the conjugate such as an anti-GFP antibody.

This embodiment was demonstrated by incubating sperm with GFP/ZP3, anti-GFP-Alexa 488, and comparison with ZP3 treated human spermatozoa. The GFP/ZP3 treated sperm that bound ZP3 were easily identified by green fluorescence over the sperm acrosome region, whereas sperm without ZP3 treatment showed no fluorescence. Of course, other optical detection systems can be used as well such as colorigenic and chemiluminescence systems.

Immunofluorescence microscopy to identify GFP/ZP3 binding with human sperm. After incubation of sperm with or without fusion protein, fixed sperm sample was probed with Alexa 488 conjugated anti-GFP antibody, which gave green fluorescence under fluorescence microscope. With the treatment of GFP/ZP3, some sperm showed binding with ZP3, which can be identified by the green fluorescence over the sperm acrosome region; those without GFP/ZP3 treatment and those treated with GFP alone did not show any green fluorescence.

Detect other released substance from the AR In preferred embodiments one or more other substances released during the acrosome reaction from reacted sperm are detected. A variety of substances are useful, including, for example, membranes of acrosome cap fragments, phospholipids, cholesterol, protein, peptides, and any other potential substance which released or changed during acrosome reaction. In a preferred embodiment a dye is added that stains spermatozoa before acrosome reaction. After treatment with an acrosome reaction inducer the effect of the dye may be determined by colorimetry, reflectance spectroscopy, fluorescence and the like. Other methods will be readily understood. For example, membrane fragments can be assayed in supernatant after centrifugation.

In a particularly useful embodiment a combination of detecting two or more released substances is used for greater accuracy. The released substance may be any material that can be differential between acrosome intact, acrosome reacting or acrosome reacted spermatozoa. A diagnostic kit is particularly useful having components (stains, fluids, instruction manual, controls, calibrators) for use in determining male infertility. In one embodiment a kit contains a solid phase particle reagent coated with a reagent described herein that is capable of binding to sperm. The kit further may comprise a solution for suspension of the particles, and one or more calibrators. In another embodiment a kit is provided that contains one or more biochemicals for detecting a substance released during the acrosome reaction.

The following examples are presented to illustrate some embodiments of the invention and are not meant to limit the scope of the claims in any way.

EXAMPLES

Commonly Used Procedures

The following general techniques are used in combination with one or more of the following examples.

Motile sperm preparation by swim-up or Percoll separation Human semen with normal parameters (WHO, 1987) is obtained from healthy donors from a donor insemination program. Freshly ejaculated spermatozoa from healthy donors are obtained by masturbation after at least 2 days of abstinence. After liquefying the ejaculate by putting it in a 37° C. incubator for at least thirty minutes, sperm samples are subjected to CASA analysis for assessing spermatozoa motility and concentration. A Hamilton-Thorn Research Sperm Analyzer is routinely used to evaluate sperm motion parameters. Samples having >40 million sperm/ml, >60% initial progressive motility and >14% normal morphology (strict criteria) are used in the experiments. Motion analysis is conducted after suspending sperm pellets in HTF medium.

Swim-up procedure After complete liquefaction and semen analysis, a standard swim-up procedure is used to select the motile spermatozoa. Semen was divided into 0.5 ml aliquots, placed at the bottom of 15 ml centrifuge tubes; then each aliquot was diluted with two volumes of Human Tubal Fluid (HTF; Irvine Scientific, Santa Ana, Calif., USA) containing 0.5% Human Serum Albumin (HSA); the sperm suspension was centrifuged for eight minutes at 400×g. The pellet was washed for a second time. The final pellet is then overlaid with 500 µl of HTF/0.5%HSA and all tubes were incubated at 37 C. under 5% $CO_2$, at an angle of 30° for one hour to allow sperm to swim from semen into medium. The overlying layer containing motile sperm is thereafter recovered for ongoing experiments.

Percoll separation Spermatozoa are isolated by discontinuous Percoll (Pharmacia) gradient separation (90% and 40% layers) using human tubal fluid supplemented with 0.5% Human Serum Albumin as diluents. Two milliliters of semen are carefully placed on Percoll layers, after centrifugation at 400×g for 20 minutes, purified population of highly motile (from 90% layer) is recovered, washed in HTF/0.5% HSA medium and centrifuged at 380×g for 10 minutes. The supernatant is discarded, and the pellet is re-suspended in HTF medium supplemented with 0.5% HSA. The final suspension is then readily subjected to motility analysis. Generally at least 90% motility is obtained.

Capacitation of sperm Motile sperm samples are incubated at 37° C. in 5% $CO_2$ for 3 more hours in the HTF/0.5%HSA, to allow capacitation.

Flow cytometry Flow cytometry is employed to test the binding activity of fusion proteins such as EGFP/ZP3 to acrosome-intact spermatozoa. Motile sperm are used in all experiments. In each test, sperm only and sperm incubated with recombinant EGFP (25 microgram/ml; Clontech) are set as the control. Capacitated sperm (2 million) are incubated with EGFP or purified recombinant fusion protein such as EGFP/ZP3 at 37 C. in 5% CO2, 95% air for a specific period as needed in the experiment. The sperm are then divided into two aliquots, one as a non-washed sample, and the other is washed with PBS twice. The wash is done by suspending the sperm pellet in 1 ml PBS and centrifuged at 600×g for 8 minutes.

Both washed and unwashed sperm samples are re-suspended in 600 microliters PBS for analysis by FACScan (Becton Dickinson Immunocytometry Systems, Mountain View, Calif.). Measurements are performed at a sample flow rate of 250–300 events/second and 15,000 events are analyzed for each sample. A gate is set on dot plot distributions of forward versus 90-degree scatter to exclude debris and clumps. Sperm that give fluorescent signals above the control EGFP are deemed positive. Data are expressed as percentage of sperm displaying fluorescence.

Example 1

This example illustrates acrosin activity detection as applied to measuring rhZP3. The procedure may be used in combination with other procedures and with improved reagents such as ZP3/ZP2 conjugates, and can be modified as will be appreciated by skilled readers.

Semen is incubated at 37° for 30 min to liquefy it. Basic parameters of the semen then are measured.

The liquefied semen is added to the top of a 90%/40% Percoll bilayers. The preparation is centrifuged at 500 g for 20 min and the supernatant discarded. The pellet is washed with HTF (human tubal fluid), which includes 0.5% HSA. The material is then centrifuged at 500 g for ten minutes and the supernatant discarded. Basic semen parameters are measured and the sperm concentration is adjusted to 20 million per milliliter. This is incubated 5 hours at 37° for capacitation; the sperm is aliquoted to 500 μL each, and Ca ionophore A23187 is added to a final concentration of 10 uM, 5 uM, 2.5 uM in separate reactions, which are incubated 1 hour at 37°. The pellet and supernatant are separated at 500 g for 10 min and the pellet washed 3 times with PBS. This is resuspended in 100 μL dd$H_2O$. The pellet/supernatant is adjusted to pH 4.0 with 0.1M HCl, incubated 10 minutes and then substrate added in 1 mL buffer solution (pH 7.8). The optical densities of the samples are measured at 405 nM every 15 min for 2 hours. The data are fit to a liner regression model to extract the slope, $Y=a+bX$, where Y is OD value and X is measured time intervals.

This procedure was used to evaluate recombinant human ZP3 as described above. The recombinant human ZP-3 induced the acrosome reaction at 30 ng/mL (i.e. minimally effective dose for sperm-zona pellucida binding inhibition in the hemizona assay) relative to control conditions (sperm culture medium or culture medium from non-transfected PA-1 cells: 19%±4.1% live acrosome-reacted sperm vs 9.2%±3.8% and 10.2%±2.7% live acrosome reacted sperm, respectively. Dong et al 2001).

Example 2

This example shows the effects of pH on the activity of acrosin released from acrosome reacted sperm. In this procedure, the acrosin supernatant is adjusted to pH 4 in order to remove the negative effect of acrosin inhibitors. FIG. 5 demonstrated after adjustment of the pH to 4, there was a significant increase of acrosin activity. When pH decreased from pH 5.6 to pH 4.0, the activity increased 10 times.

Example 3

This example shows that acrosin activity is much higher in calcium ionophore induced acrosome reacted sperm than in sperm without calcium ionophore induction. In this procedure, an initial supernatant is collected from calcium ionophore induced acrosome reacted semen samples. The acrosin activity is tested from the samples and was not found to differ appreciably between samples and controls. However, as optical density measurements continued from the supernatant acrosin released from acrosome reacted sperm increased with time. Portions of the same semen samples were simultaneously tested for acrosome reaction by PSA staining, which when assayed will also show a correlation useful for diagnostic testing. Both measurements thus may be used to correlate calcium iionophore induced concentration and the activity of acrosin released from acrosome reacted sperm.

Example 4

This example demonstrates the use of weighted acrosome measurements for improved accuracy. A representative example of this method is as follows. In a first step a group of prepared sperm that have undergone acrosome reaction and histological staining with a fluorescent material are classified by their exhibited pattern of morphological changes into four categories: 1) non acrosome reacted, which can be visualized by fluorescence located in the entire sperm acrosomal region (Table 1); 2) sperm in the early stages of AR, which are visualized by fluorescence in a clearly damaged sperm acrosome, 3) sperm in the middle stages of AR, which are recognized as having fluorescence in the sperm equatorial segment, and 4) sperm that have undergone complete acrosome reaction and are identified as having no fluorescence stain in the sperm head. (See Arts et al, 1994 for further details useful for this example).

In a second step, each type is given a score. In this example, Type I has fluorescence in the acrosomal region, indicating intact acrosome; Type II has fluorescence in a clearly damaged acrosome; Type III has fluorescence in the equatorial segment; and Type IV has no detectable fluorescence in the head. Each type, in the representative example is given a score as follow. Type I has 0 points, Type II has 1 point, Type III has 1.5 points and Type IV has 2 points. Of course different numbers of types may be scored and different weighting systems may be used, depending on knowledge of the system used and the conditions and reagents used for scoring each type. In this example, the sperm are examined under a fluorescence microscope and the percentage of each category is recorded. To determine the total AR score, the percentage of each category type is multiplied by the appropriate point and added together as shown in the equation below and in

TABLE 1

0 × (% of Type I) + 1 × (% of Type II) + 1.5 × (% of Type III) + 2 × (% of Type IV) = Total AR score

|  | I | II | III | IV | AR percentage |
|---|---|---|---|---|---|
| ZP3 induced AR | 59% | 12% | 22% | 7% | 29% |
| Score of ZP3 induced AR | 0 | 12 | 33 | 14 | 59 |
| Ca-ionophore 10 uM | 60% | 7% | 18% | 15% | 32% |
| Score Ca-ionophore 10 uM | 0 | 7 | 27 | 30 | 64 |
| Negative control | 79% | 10% | 7% | 4% | 11% |
| Score of Negative control | 0 | 10 | 10.5 | 8 | 28.5 |

It was found that the total AR score more accurately reflects the process of acrosome reactivity among sperm samples than previous techniques that do not weight the morphological results.

Example 5

This example demonstrates rhZP3 purification. A wheat germ agglutinin was used for a chromatography initial isolation step. The isolated glycoproteins were further purified by DEAE-ion exchange chromatography. Typically 0.2 to 0.6 mg of recombinant ZP3 containing glycoprotein were be isolated from one liter of media. In a preferred embodiment, a six-histidine tag was added to the C-terminus of the rhZP3 via genetic engineering and a Ni-NTA affinity column from (QIAGEN) was used for further purification.

Alternatively or in addition Fast Performance Liquid Chromatography (FPLC) with a Resource Q column alternatively is used for further purification. Western blot analysis of this FPLC mediated purification can be used to check purity, or SDS-PAGE electrophoresis, with staining by coomassie blue. Such procedure has shown, by densitometer scanning analysis, that prepared rhZP3 accounted for 80% to 90% of the total purified proteins. Thus, 0.2 milligram to 0.4 milligrams or more of rhZP3 typically was purified from one liter of culture medium.

Example 6

This example demonstrates sperm capacitation optimization. The time course study of sperm capacitation in combination with rhZP3 was evaluated. After different periods of capacitation, sperm were treated with rhZP3 (30 ng/ml) for thirty minutes to trigger the acrosome reaction. The results revealed an increase in the percentage of acrosome-reacted sperm as the capacitation time lengthened up to 8 ~10 hours. In many embodiments with rhZP3 an approximate 4 hour capacitation time is preferred because at this time frame the sperm are 99% alive as compared to 86%, 82% and 66% of live sperm for 8, 12 and 24 hours of capacitation time respectively. Experiments were performed after 4 hours of capacitation. The ratio of acrosome-reacted spermatozoa increased by 1.5 fold, after incubation with 30 ng/mL rhZP3, as compared to controlled conditions. This increased activity is much stronger than the increased activity produced after incubation with rhZP3 made by CHO cells. The CHO cell product induced a similar percentage of acrosome reaction in human sperm following 24-hour sperm capacitation at a dose of 15–20 ng/μl (van Duin et al, 1994).

Example 7

This example demonstrates the formation of an artificial zona and its use for a more convenient and rapid test for male fertility. Purified GFP-rhZP3 was prepared as described herein was immobilized on 100 micron diameter agarose beads that had been precoated with nickel ion (Qiagen) as is known in the art. Spermatozoa were capacitated for 3 hours at 37 degrees centigrade in the presence of 5% carbon dioxide and then incubated with the GFP-rhZP3 coated beads for 30 minutes. Binding was determined by microscopy. Spermatozoa were found bound to agarose beads coated with GFP-rhZP3.

In other studies, recombinant GFP-rhZP3 is coated on beads made of different material such as agarose, polystyrene and silicon, to lower non-specific sperm binding. Optionally affinity conjugation using wheat germ agglutinin, nickel, cobalt and anti-GFP antibody precoated beads and a wide variety of chemical conjugation methods are used for improved protein binding.

In yet other studies, solid phases are prepared having immobilized GFP-rhZP2 and GFP-rhZP3 complexes. In yet another embodiment, rhZP2 and rhZP3 are constructed in a manner that mimics the natural ZP2–ZP3 filament.

Example 8

This example illustrates the expression of recombinant human ZP2. To study the expression of human ZP2 in bacteria cells, different expression vectors were constructed according to its domain structure. Briefly, the PCR generated fragment of human ZP2 N-terminal 103–618 bp was subcloned into the pRSET bacteria expression vector with 6×His-Xpress tag at the N-terminal to construct pZ2N. Using restriction enzyme digestion, the fragment of human ZP2 C-terminal 847–2235 bp was subcloned in pRSET vector with 6×His-Xpress tag at the N-terminal to make pZ2C. Combined with PCR and restriction enzyme digestion, the fragment of human ZP2 (103–1847 bp) without signal peptide and C-terminal after protease cleavage site was subcloned in pRSET vector with 6×His-Xpress tag at the N-terminal to generate pZP2. All constructs were confirmed by DNA sequencing or restriction enzyme digestion analysis.

The constructs were then transformed into BL21 (DE3) pLysS bacteria cells. The expressed recombinant human ZP2 proteins were purified under denatured condition by Ni-NTA spin column and analyzed by SDS-PAGE and Western blot with customized human ZP2 polyclonal antibody and Xpress monoclonal antibody. Major protein bands with expected molecular weights (pZ2N: 22.8 kDa, pZ2: 73.5 kDa, pZ2C: 61.2 kDa) were detected and confirmed by Western blot with antibodies against human ZP2 and Xpress. Human ZP2 and ZP3 can form dimers. The rhZP3 protein was expressed in bacteria cells but the expressed protein experienced some degradation. Therefore, both rhZP2 and rhZP3 expression vectors but with different selection markers were co-transformed into BL21 (DE3)pLysS cells. Expressed proteins are purified under native condition and analyzed on native protein gel and Western blot to show that coexpressed rhZP2 and rhZP3 can form dimers that are more stable, easier to purify and easier to store.

To express recombinant human ZP2 protein in mammalian cells, rhZP2 expression vectors were constructed. pZ2 vector was generated by PCR and restriction enzyme digestion from human ZP2 cDNA before the protease cleavage site and subcloned into pcDNA6a with V5-6×His tag at the C-terminal end. In order to easily monitor the production and purification of rhZP2 protein, fluorescent protein tag—DsRed was generated by PCR and inserted between hZP2 and V5-6×His tag to construct pZ2DsRed. These constructs were stable-transfected into 293 cells and clones were selected by blasticidin. Their expressions were detected by RT-PCR.

To boost the expression of rhZP2 in mammalian cells, the dhfr gene was inserted into a pZ2 vector and then stably-transfected into CHO/dhfr$^-$ cells. Under CHO/dhfr$^-$ selection system, stably-transfected genes are amplified and show greatly increased protein expression level.

Example 9

This example demonstrates the effects of agonists on inducing acrosome reaction by rhZP3. The acrosome reaction was studied in response to purified rhZP3, natural solubilized human ZP and the calcium ionophore. The data (see Table 2) show that all agonists enhanced the percentage of acrosome reacted sperm when compared to control conditions (i.e., culture medium alone or protein purified from non-transfected PA-1 cells).

TABLE 2

Percentage of acrosome-reacted sperm as determined by FITC-PSA.

| | Negative control | Non-transfected ("NT", 30 ng/ml) | Calcium ionophore (5 μM) | rhZP3 (30 ng/ml) | Solubilized zona (0.5 ZP/μl) |
|---|---|---|---|---|---|
| % Acrosome reacted-sperm | 7.7 (3.2) | 9.5 (2.4) | 22.5 (4.1)* | 18.3 (1.4)* | 14.8 (6.2)* |
| % Sperm viability | 95.1 (2.6) | 98.0 (1.0) | 96.5 (2.0) | 96.7 (3.2) | 97.2 (2.5) |

*P < 0.05 compared to control conditions
Mean (±SEM), n = 29 ejaculates from 11 different donors, 3 different purification lots of rhZP3.

Example 10

Cells are grown in culture dishes (150 mm). Approximately, 100–300 ug of rhZP3/GFP from 1 liter of conditioned medium are produced each week. This amount of protein is enough to test 50–60 sperm samples. In order to produce large amount of protein for future commercialization, a continuous culture system is made. To increase the expression of rhZP3/GFP and make it easy for protein purification, different serum free media are tested. A starting condition is MEM/F12 with 5% FBS. This is gradually decreased with step percentages of FBS between 5% to 4.5, 4.0, 3.5, 3.0, 2.5, 2.0, 1.5, 1.0, 0.5, and 0%. The stable-transfected cells become established in serum-free medium after 2–3 months. After establishing the suspension culture conditions, a bioreactor is used for industrial production of rhZP3/GFP.

After testing with medium containing GFP/ZP3, a purification scheme using multiple column chromatography was simplified to the use of two columns, a wheat germ agglutinin column and a nickel Ni-NTA column. The combined use of these columns allowed purity levels to exceed 60% with limited loss. Additional columns such as an immunoaffinity column are used to further purify GFP/ZP3 to more than 90%. Further use of FPLC provides automation options and consistency, and to stream line the purification procedure.

Example 11

In this example prepared rhZP3/GFP was further purified for a sperm binding study. A hexahistide inserted in the front of the fusion protein sequence was relied on for purification by nickel chelated affinity column (Ni-NTA). To facilitate the purification, a Blue Affi-gel was used to remove albumin and protease from the culture medium. The WGA column was applied to catch glycoprotein from the medium though Blue gel. The proteins eluted from the WGA column were applied to the equilibrated Ni-NTA resin in a batch purification procedure in a pilot experiment to check which concentration of imidazole can be used for eluting the target protein. Different concentrations of imidazole are used to elute protein, i.e., 20 mM, 40 mM, 80 mM, 100 mM, 160 mM and 200 mM. By using these methods, a 60~70% purity of GFP/ZP3 was purified. To further purify the rhZP3/GFP, FPLC an immunoaffinity chromatography is employed.

Using a combination of WGA and Ni-NTA chromatography, a 60~70% purity of GFP/ZP3 was acquired. The SDS-PAGE revealed that this purified protein sample contains some other minor proteins. Most of these proteins have molecular weights from 20 to 60 kD. In order to remove the low molecular weight proteins, the FPLC system (Amersham Pharmacia Biotech, NJ, U.S.A.) equipped with Superdex 200 (fractionation range: $1 \times 10^4$–$6 \times 10^5$) gel filtration column (Amershame Pharmacia Biotech, N.J., U.S.A.) may be applied. Additional purity of rhZP3/GFP is possible with FPLC. Furthermore, use of the FPLC system can lead to greater flexibility and automation.

Example 12

In order to reach a higher purity of rhZP3/GFP an anti-hZP3 immunoaffinity chromatography step is employed. Using a protein analysis program a human specific 14 amino acid-epitope was identified that is located at the C-terminus of hZP3 was identified. Synthesis and production of polyclonal antiserum against this oligopeptide was carried out by Biosynthesis (Lewisville, Tex.). Specificity studies of rabbit antiserum revealed that the anti-hZP3–14 antiserum showed a good specificity as determined by Western blot analysis. The anti-hZP3 immunoaffinity column is prepared by immobilizing anti-hZP3 on a Sepharose 4B resin with a routine conjugating procedure. The protein samples are passed through the anti-hZP3 immunoaffinity column after adjustment of protein concentration to 800 μg/ml, to minimize protein precipitation in the column. The column is washed with 20-column volume of 20 mM Tris-HCl (pH 7.4) buffer, containing 0.5% Tween 20 to remove non-specific bound proteins. The column is then washed with 5-column volumes of 20 mM Tris-HCl (pH 7.4) buffer. The resin bound proteins are eluted with 50 mM Acetic Acid, pH 3.0. The pH of the eluted solution is brought to pH 7.4 immediately with 1M Tris-HCl (pH 9.5) buffer. The eluted proteins are concentrated with Centricon with 30 kD cut off (Amicon, Mass.). The concentrated protein sample is dialyzed against PBS, pH 7.4. The dialyzed protein sample is stored at 4° C. or −20° C. for extended storage. Biological activity of the purified material is assayed and found to be higher in specific activity than unpurified material.

Example 13

This example illustrates the construction of rhZP2 and rhZP3 expression systems, and rhZP2/rhZP3 co-expression systems.

Since the hZP2 signal peptide is cleaved after protein synthesis a histidine tag was introduced at the downstream of the signal sequence of hZP2 to form a histidine tagged fusion protein. Since the signal sequence of hZP2 and a set of sequence of six histidine tag together are too long for generating the oligonucleotide, a pair of PCR primers were designed to introduce the BamHI restriction digest site at upstream and the Hind III restriction digest site at downstream of hZP2 signal sequence. Another pair of PCR primers were designed to generate a DNA fragment having a Hind III restriction digest site and six histidine codon at upstream and a XhoI restriction digest site at downstream of hZP2 cDNA excluding the N-terminal signal sequence and the C-terminal transmembrane-like domain. These two PCR products were digested with the Hind III restriction enzyme and then ligated to form the Signal sequence-6 Histidine-rhZP2cDNA excluding the N-terminal signal sequence and the C-terminal transmembrane-like domain fragment, which is flanked by upstream BamHI restriction digest site and downstream XhoI restriction digest site. The generated DNA fragment was cloned at downstream of the CMV promoter of pcDNA 3.1 vector with hygromycin as the selection marker.

Since the hZP3 signal peptide is cleaved after protein synthesis, a histidine tag was introduced downstream of the signal sequence of hZP3 to form a histidine tagged fusion protein. A pair of PCR primers were designed to produce a DNA fragment of hZP3 cDNA excluding the N-terminal signal sequence and the C-terminal transmembrane-like domain that was flanked by upstream Hind III restriction digest site and downstream XhoI restriction digest site. The oligonucleotide of BamHI restriction digest site, hZP3 signal sequence, 6-histidine tag sequence and Hind III restriction digest site was annealed with its compliment oligonucleotide to form a double strand DNA fragment to have the arrangement of BamHI restriction digest site-hZP3 signal sequence-six histidine tag sequence-Hind III restriction digest site. This DNA fragment and the truncated hZP3 DNA fragment were digested with Hind III restriction enzyme and then annealed. The generated DNA fragment was cloned at downstream of the CMV promoter of pcDNA 3.1 vector with the Neomycin as select marker.

The rhZP2 and rhZP3 vectors were co-transfected into the PA-1 cell and 293 cells with the Superfect™ reagent (Qiagen, Hilden, Germany). Twenty-four hours after transfection, the cocktail containing 1000 μg/ml of G418 and 500 μg/ml of Hygromycin was used for selecting stable co-transfected cell clones.

A pair of primers were designed to introduce the upstream BamH I and sequence of six histidine tag and downstream the sequence for enterokinase K and Hind III restriction digest site to the rhZP2cDNA fragment corresponding to hZP2, excluding the N-terminal signal sequence and the C-terminal transmembrane-like domain. Another pair of primers was designed to introduce the upstream Hind III restriction digest site and downstream Xho I restriction digest site to the rhZP3 cDNA fragment corresponding to hZP3, excluding the N-terminal signal sequence and the C-terminal transmembrane-like domain. These two cDNA fragments were digested with Hind III restriction enzyme and then ligated. The generated DNA fragment [BamH I restriction site-six histidine tag-rhZP2 (excluding the N-terminal signal sequence and the C-terminal transmembrane-like domain)-enterokinase K-rhZP3 (excluding the N-terminal signal sequence and the C-terminal transmembrane-like domain)] was cloned at downstream of the CMV promoter of pcDNA 3.1/neomycin vector. The stable transfected cell lines were selected with 1000 μg/ml of G418.

The rhZP2–ZP3 fusion protein, rhZP2–rhZP3 filament, rhZP2, and rhZP3 were isolated from the culture medium by the following methods. The culture medium were concentrated with the Ultrafiltration chamber (Amerco) equipped with YM-10 ultrafiltration disk membrane (Amerco) followed by dialyzed against the Ni-NTA binding buffer (50 mM PBS, 300 mM NaCl, pH 8.3). The Ni-NTA affinity chromatography (Qiagen) was performed under the batch binding condition with end-to-end shaking at 4° C. overnight. After binding, the Ni-NTA resin was washed with 5 column volumes of Ni-NTA binding buffer containing 4 mM Imidazole. The resin bound proteins were eluted from the Ni-NTA resin with the Ni-NTA binding buffer containing 200 mM of Imidazole.

A combination of CM-Affi-Gel-Blue Gel (Bio-Rad), Wheat Germ Agglutinin (WGA)(Vector Laboratories. Inc., Burlingame, Calif.), and Ni-NTA affinity chromatography was used as an alternative way of purification of these glycoproteins. The culture medium was passed through the combination of CM-Affi-Gel-Blue Gel (Bio-Rad), Wheat Germ Agglutinin (Vector). The CM-Affi-Gel-Blue Gel will remove the albumin and some proteases from the culture medium. WGA bound glycoproteins were eluted by using WGA washing buffer (20 mM PBS, 150 mM NaCl, pH 7.3) containing 500 mM of N-acetyl-D-glucosamine. The eluted glycoproteins were dialyzed against the Ni-NTA binding buffer overnight with change buffer twice. The Ni-NTA affinity chromatography (Qiagen) was performed under the batch binding condition with end-to-end shaking at 4° C. overnight. After binding, the Ni-NTA resin was washed with 5 column volumes of Ni-NTA binding buffer containing 4 mM Imidazole. The resin bound proteins were eluted from the Ni-NTA resin with the Ni-NTA binding buffer containing 200 mM of Imidazole.

The isolated glycoproteins were analyzed with the SDS-PAGE electrophoresis and 2-D electrophoresis followed by western blotting. A Hoefer SE 220 minigel electrophoresis apparatus (Hoefer Pharmacia Biothch Inc., San Francisco, Calif.) and a discontinuous SDS gel system were used to perform electrophoresis. Twenty milliliter of 8% separating gel mix [9.4 ml of $H_2O$, 5.3 ml of 30% Acrylamide mix (Bio-Rad), 1.5 ml of 1.5 M Tris, pH 8.8 (Fisher), 100 μl of 10% APS (Sigma), 200 μl of 10% SDS (Sigma), 12 μl of TEMED (Sigma)] was poured between the glass plates. The separating gel was overlayed with water saturated n-Butanol and after 40 minutes to 1 hour this overlay n-Butanol was removed and replaced with 8 ml of 4% stacking gel mix (5.5 ml of $H_2O$, 1.3 ml of 30% Acrylamide mix, 1 ml of 1M Tris, pH 6.8, 80 μl of 10% APS, 80 μl of 10% SDS, 8 μl of TEMED) (Naito, et. al., 1973). Five microgram of glycoprotein were dissolved in the denature treatment buffer (0.0625 M Tris-Cl, 2% SDS, 10% glycerol, 5% 2-mercaptoethanol, pH 6.8) and loaded into the well. Rainbow colored protein molecular weight markers (Amersham Life Science, Little Chalfont Buckinghamshire, England) were used to determine the molecular weight of protein samples. Running buffer (0.025 M Tris, 0.192 M Glycine (Fisher), 0.1% SDS) was poured into the upper and lower reservoirs.

Gels were run at 25 mA constant current until the dye front reached the bottom of the gel. The gel was stained with Coomassie Blue stain solution (0.025% coomassie blue R-250 (Sigma), 40% Methanol (Fisher), 7% Acetic Acid (Fisher)) and destained with destaining solution I (50% Methanol, 10% Acetic Acid), which was followed by destaining solution II (5% Methanol, 7% Acetic Acid). To confirm the purity of the purified recombinant proteins the Two-dimensional electrophoresis was performed by using a Tube Gel Adaptor Kit (Hoefer). Isoelectric focusing gels were made in glass tubing (7.5 cm×1.5 mm inside diameter) sealed at the bottom with Parafilm. To prepare 5 ml of isoelectric focusing gel mixture: 2.75 g of Urea (Fisher) was added to a 100 ml side arm flask, then 665 µl of 30% Acrylamide (Bio-Rad), 1 ml of 10% (w/v) Nonidet P-40 (NP-40) (Sigma), 985 µl of $H_2O$+200 µl of Ampholines, pH range 3 to 5 (Bio-Rad),+50 µl of Ampholines, pH range 3 to 10 (Bio-Rad).

The mixture of solution was swirled until the urea was completely dissolved, then 10 µl of 10% ammonium persulfate (Sigma) were added and the solution was degassed under vacuum for about 1 minute. Immediately after addition of 7 µl of TEMED (Sigma), the solution was loaded into the gel tubes. The gel was overlayed with gel overlay solution (8 M Urea) and after 1 to 2 hours this overlay solution was removed and replaced with 5 µl sample buffer (9.5 M Urea, 2% (w/v) NP-40, 2% Ampholines (comprised of 1.6% pH range 3 to 5 and 0.4% pH range 3 to 10) and 5% 2-mercapto-ethanol (Fisher)). The tubes were then loaded into the adaptor and all unused bottom ports was sealed off by inserting a cone-shaped stopper (Hoefer). The lower reservoir was filled with 0.01 M $H_3PO_4$ and the upper reservoir was filled with 0.02 M NaOH which should be extensively degassed to remove $CO_2$. The gels were then prerun at 300 volts for 30 minutes. The power was turned off, the upper reservoir was emptied, sample buffer was removed from the surface of the gels, and the samples prepared with the sample buffer were loaded. The samples were overlayed with sample overlay solution (9 M Urea, 2% (w/v) NP-40, 1% Ampholines (comprised of 0.8% pH range 3 to 5 and 0.2% pH range 3 to 10)) then 0.02 M NaOH, and the chamber was refilled. After the samples were loaded, the gels were run at 400 volts for 12 hours and then at 800 volts for 1 hour. The gels were removed from the tubes and equilibrated with SDS sample buffer (10% (w/v) glycerol (Fisher), 5% 2-mercaptoethanol, 2.3% (w/v) SDS, and 62.5 mM Tris-HCl, pH 6.8, 0.1% bromphenol blue (Sigma)) at room temperature for 40 minutes with shaking. The Hoefer SE 220 minigel electrophoresis apparatus (Hoefer) and discontinuous SDS gel system were used to perform the second dimension electrophoresis.

Twenty milliliters of 8% separating gel mix [9.4 ml of $H_2O$, 5.3 ml of 30% Acrylamide mix (Bio-Rad), 1.5 ml of 1.5 M Tris, pH 8.8 (Fisher), 100 µl of 10% APS (Sigma), 200 µl of 10% SDS (Sigma), 12 µl of TEMED (Sigma)] was poured between the glass plates. The separating gel was overlayed with water saturated n-Butanol and after 1 to 2 hours this overlay n-Butanol was removed and replaced with 8 ml of 4% stacking gel mix (5.5 ml of $H_2O$, 1.3 ml of 30% Acrylamide mix, 1 ml of 1M Tris, pH 6.8, 80 µl of 10% APS, 80 µl of 10% SDS, 8 µl of TEMED). The cylindrical isoelectric focusing gel was placed on the stacking gel and fixed with 1% agarose gel which was prepared with running buffer (0.025 M Tris, 0.192 M Glycine (Fisher), 0.1% SDS). Gels were run at 25 m amp constant current until the dye front reaches the bottom of the gel. The gel was stained in Coomassie Blue stain solution.

The proteins separated with either SDS-PAGE electrophoresis or 2-D electrophoresis were wet transferred from gel to hybond ECL nitrocellulose membrane (Amersham) that was performed at 100 Volts for 2.5 hours at 4° C. with the transfer buffer (25 mM Tris-HCl; 192 mM glycine (Fisher); 20% methanol (Fisher), pH 8.3). After transferring, the nitrocellulose membrane was blocked with blocking buffer [5% Non-Fat-Dry Milk, 0.1% Tween 20 in PBS, pH 7.3] at room temperature for 3 hours by gently shaking. The antibodies against the hZP2 or hZP3 were used as primary antibody, which was diluted at 1:5000 in blocking buffer. Blocked nitrocellulose membrane was incubated in the primary antibody solution at room temperature for one and half hour with gentle shaking. The nitrocellulose membrane was washed with washing PBS containing 0.4% Tween 20 for 15 minutes three times with fresh changes of the washing buffer. The secondary antibody [goat anti-rabbit IgG-HRP antibody conjugate (Amersham)] was diluted by the washing buffer A at 1:2000 dilution.

After washing with washing buffer, the nitrocellulose membrane was incubated in secondary antibody solution at room temperature for one hour. The membrane was washed with washing buffer B (PBS containing 0.3% Tween 20) for fifteen minutes three times with fresh changes which was followed by washing buffer C (PBS containing 0.1% Tween 20) for five minutes three times with fresh changes of the washing buffer. The nitrocellulose membrane was exposed to the detection solution [detection reagent 1 and detection reagent 2 (1:1, v/v) (Amersham)]. The membrane was placed with protein side face to film and exposed in the film cassette for 30 to 60 seconds. The film was developed with a Konica developing machine. For a sperm binding assay, an aliquot of semen (0.5 ml) was diluted with 1 ml of Ham's F-10 medium (Gibco) supplemented with 0.5% heat-inactivated human serum albumin (HSA). The sperm were centrifuged (5 minutes, 300×g), and then washed a second time. The final pellet was overlaid with 0.5 ml of F-10 medium with HSA and incubated at 37° C., 5% $CO_2$ in air to achieve a separation of the motile sperm fraction. After 1 hour, the sperm supernatant was removed and used for the sperm binding assay. One 100 µl droplet of the control sperm suspension (500,000 motile sperm/ml) was incubated with rhZP2 in an eppendorf tube.

A second eppendorf tube was similarly prepared with a droplet of the sperm suspension incubated with rhZP2–ZP3 fusion protein or rhZP2–rhZP3 filament for 30 minutes. Spermatozoa were fixed on the assay slide and probed with fluorescent-labeled anti-hZP2 antibody. Assay slides were read using an epifluorescent microscope at 400× magnification; duplicate were evaluated for each treatment and time analyzed, assessed blindly by two different experienced observers and results averaged. At least 200 cells were evaluated per slide for each factor. The binding index was calculated by the following formula: A= The number of spermatozoa show rhZP2–ZP3 fusion protein positive in 100 observed spermatozoa or the number of spermatozoa show rhZP2–rhZP3 filament positive in 100 observed spermatozoa from the same ejaculation. B= The number of spermatozoa show rhZP2 positive in 100 observed spermatozoa from the same ejaculation. C=The number of spermatozoa show rhZP2 positive in 100 observed spermatozoa from the same ejaculation treated with ionophore A23187 wherein (A−B)/C×100=Sperm Binding Index (%).

Example 14

This example illustrates materials and methods for monitoring the acrosome reaction. Initially, optimal AR conditions are established for a physiological acrosome inducer for the period during capacitation and AR interval. The interval of capacitation for sperm before AR, especially under rhuZP3 induction, has not been established. 3 to 6 hours may be a reasonable interval; nevertheless, AR induced by $Ca^{2+}$ ionophore A23187 was not in this interval. Solubilized ZP and $Ca^{2+}$ ionophore induced AR must have different capacitation and optimized condition (Bielfeld et al, 1994). It has been found that sperm capacitation in BSA will increase the sperm membrane preparation before AR occurs; therefore, an optimal culture medium (w/o Albumin, $Ca^{2+}$) of capacitation will enhance the AR result. Before rhuZP3 is purified, there is not enough ZP to determine the optimal condition of human sperm AR under physiological conditions.

The following studies are carried out: (1) incubate post-washed sperm in HTF or Ham's F-10 with/without $Ca^{2+}$ for 2,3,4,6 and 20 hours then induce AR using different inducers ($Ca^{2+}$ ionophore A23187, progesterone and rhZP3), (2) incubate capacitation sperm with different inducers for 0.5, 1, 2, 3, 4 and 20 hours. FITC-PSA, CTC and released enzyme are used to compare those results.

A reliable method for detecting released enzyme during AR is established using the acrosin measurement procedure of Kennedy et al, 1989 and acid phosphatase procedure of Salzberger et al, 1992. ELISA-like assays (Margalit et al, 1997) are used to detect the content of the released enzyme. In particular, the relationship between morphological change and released enzyme during AR is determined using several staining methods to identify the acrosome status of sperm (such as FITC-PSA, FITC-PNA, FITC-CD46, FITC-ConA). FITC-CD46,FITC-PNA, and FITC-PSA, which can identify different stages of AR (CarverWard et al, 1997). These staining methods are used for the same samples to determine the percentage of AR at different stages. Furthermore, chlortetracycline (CTC) assay is used to determine the time course of capacitation and AR in human sperm using rhuZP3 and $Ca^{2+}$ ionophore A23187 as inducers (Ward et al, 1984, Lee et al, 1987, Perry et al, 1995). These procedures generate data that indicate that sperm undergo AR via several stages. It is seen that different enzymes are released enzymes at different morphological stages.

Example 15

This example illustrates AR detection via released enzyme. Staining specimens, reading slides and detecting AR is a labor-intensive and subjective procedure. The released enzyme, instead are used to detect AR. Acrosin and acid phosphatase are used for this approach. Liberated enzyme under rhuZP3-induced AR is quantitated as will be appreciated by a skilled artisan and provides an objective method for detecting AR functionally, as follows. Enzyme as an Marker of AR

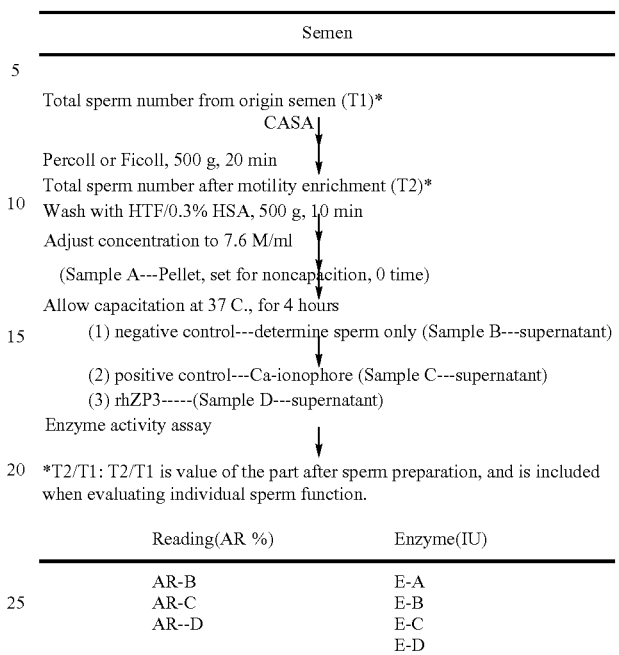

| Semen |
|---|
| Total sperm number from origin semen (T1)* |
| CASA ↓ |
| Percoll or Ficoll, 500 g, 20 min |
| Total sperm number after motility enrichment (T2)* |
| Wash with HTF/0.3% HSA, 500 g, 10 min |
| Adjust concentration to 7.6 M/ml |
| (Sample A---Pellet, set for noncapacition, 0 time) |
| Allow capacitation at 37 C., for 4 hours |
| (1) negative control---determine sperm only (Sample B---supernatant) |
| (2) positive control---Ca-ionophore (Sample C---supernatant) |
| (3) rhZP3-----(Sample D---supernatant) |
| Enzyme activity assay ↓ |

*T2/T1: T2/T1 is value of the part after sperm preparation, and is included when evaluating individual sperm function.

| Reading(AR %) | Enzyme(IU) |
|---|---|
| AR-B | E-A |
| AR-C | E-B |
| AR--D | E-C |
| | E-D |

| Result table | | | |
|---|---|---|---|
| Specimen | Reading | Enzyme | Note |
| Sample A | | E-A | After motility enrichment, Sperm basic enzyme level - before capacitation, set E-A zero time |
| Sample B | AR-B | E-B | After capacitation, set E-B negative control |
| Sample C | AR-C | E-C | After capacitation, set E-C positive control |
| Sample D | AR-D | E-D | After capacitation, set E-D rhZP3 |

Sample A:
Sample A is sperm obtained before capacitation
E-A is the value of enzyme which is contained in the sperm and released after Triton X-100 treatment.
Sample B:
Sample B is the negative control, sperm medium only
AR-B is the reading value of % AR in medium; therefore, there are 2 × $10^{-7}$/ml X AR-B acrosome-reacted sperm. This data is the basal AR.
E-B is the enzyme level in the supernatant of sperm-only sample. It should contain the enzyme which is released by spontaneous AR.
E-B, therefore, should have a positive relationship with AR-B
Sample C:
Sample C is obtained from the positive control of AR (induced by A-23187 10 uM)
AR-C % is the reading value of % AR; therefore, there are 2 × $10^{-7}$/ml × AR-C % acrosome reacted sperm.
E-C is the enzyme level in the supernatant of post-AR sample, it should contain the enzyme which is released by acrosome-reacted sperm.
E-C, therefore, should have a positive relationship with AR-C %
Sample D:
Sample D obtained from rhZP3, or progesterone, or another chemical which can induce physiological AR.
AR-D % is the reading value of % AR which is induced by rhZP3 (or progesterone), therefore, there are 2 × $10^{-7}$/ml × AR-D % acrosome-reacted sperm.
E-E is the enzyme level in the supernatant of a post-AR sample, and it should contain the enzyme which is released by AR.
E-E, therefore, should have a positive relationship with AR-D %
To compare positive control, E-D/E-B represents the efficiency of rhZP3 to induce AR.

The data obtained are analyzed as follows. The relationships between morphological reading (AR-B, AR-C, AR-D) and enzyme reading (E-B, E-C, E-D) are established by using different approach: Morphological reading are made, including the use of electron microscopy, multiple histochemical stains, labeled lectins, and labeled antibodies, CTC and flow cytometry. All these assays depend on those membrane changes that lead to complete or partial loss of the acrosomal cap. Enzyme readings are carried out, E-A is the basic enzyme reading, and is a reference for individual variation, therefore, E-D/E-A is the relative value of each sample. In another method Enzyme activity is determined using a gelatinolysis technique (Henkel et al, 1995) which contained with rhZP3 as physiological induced. Halo diameter, halo formation rate can be an indictor of enzyme activity. (T2/T1)×(E-D/E-A) or (T2/T1)×(E-D/E-B) could be the simple formula to detect sperm function.

Example 16

This example illustrates binding of protein to carboxylate modified microspheres. In one experiment purified GFP-rhZP3 glycoprotein was dialyzed against conjugation buffer overnight with a buffer change. The GFP-rhZP3 was concentrated to reach a final concentration above 1 mg/ml with Centricon 30. Then 0.4 mg of EDC (1-ethyl-3-(3-dimethylaminopropyl)-carbodiimide and 0.6 mg NHS (N-hydroxysuccinimide) were added to 1 ml of beads in conjugation buffer containing 40 microliters of 5 micron beads or 20 microliters of 0.2 micron beads. Beads were allowed to react for 15 minutes at room temperature. Beads were separated from the reaction solution by centrifugation. The activated beads were re-suspended in 1 ml of concentrated GFP-rhZP3. The proteins were allowed to react for 2 hours at room temperature. Hydroxylamine was added to a final concentration of 10 mM to quench the reaction, which regenerates the original carboxylates. Coated beads were separated from the reaction mixture with centrifugation and washed with conjugation buffer twice. The GFP-rhZP3 conjugated beads were re-suspended in Ham's F-10 containing 5% HAS and stored at 4 degrees centigrade.

Prepared beads are successfully used in an artificial zona assay. An aliquot of semen (0.5 ml) was diluted with 1 ml of Ham's F-10 medium (Gibco) supplemented with 0.5% heat inactivated human serum albumin (HSA). The sperm were centrifuged for 5 minutes at 300 g and washed twice. The final pellet was overlaid with 0.5 ml of F-10 medium with HSA and incubated at 37 degrees C. in 5% carbon dioxide in air to achieve a separation of the motile sperm fraction. After 1 hour, motile spermatozoa were recovered and capacitated in 37 degrees C. 5% carbon dioxide for 24 hours. One 100 microliter droplet of the control sperm suspension (500,000 motile sperm/ml) was incubated with artificial zona in a Petri dish under oil for 3 hours. After co-incubation, each artificial zona was removed and pipetted five times to dislodge loosely attached sperm. The number of sperm tightly bound to the outer surface was counted. The number of artificial zona bound sperm is compared with the number of control sperm from the hemizona assay in a percentage manner to evaluate the sperm binding capability of artificial zona.

The hemizona assay is employed as a parallel assay to evaluate the binding ability of GFP-rhZP3 coated agarose beads. An aliquot of semen is processed as described above. Both sperm and artificial zona are processed as described above. For each hemizona pair, the HZI was calculated as follows: (number of test sperm bound to the hemizona/number of fertile sperm bound to hemizona)×100. The number of sperm bound to the hemizona from donor and patient samples is used as a control to evaluate the sperm binding ability of artificial zona.

Purified rhZP2 glycoproteins are dialyzed against conjugation buffer overnight with one buffer change. The rhZP2 was concentrated to a final concentration above 1 mg/ml with a Centricon 30 pressure cell. Then 0.4 mg of EDC (1-ethyl-3-(3-dimethylaminopropyl)-carbodiimide and 0.6 mg NHS (N-hydroxysuccinimide) were added to 1 ml of beads in conjugation buffer containing 40 microliters of 5 micron beads or 20 microliters of 0.2 micron beads. Beads were allowed to react for 15 minutes at room temperature. Beads were separated from the reaction solution by centrifugation. The activated beads were re-suspended in 1 ml of concentrated rhZP2 and GFP-rhZP3. The proteins were allowed to react for 2 hours at room temperature. Hydroxylamine was added to a final concentration of 10 mM to quench the reaction, which regenerates the original carboxylates. Coated beads were separated from the reaction mixture by centrifugation and washed with conjugation buffer twice. The GFP-rhZP3 conjugated beads were re-suspended in Ham's F-10 containing 5% HAS and stored at 4 degrees centigrade. Prepared beads are successfully used in an artificial zona assay Example 17

In this example, GFP-rhZP3 is affinity conjugated and also chemically coupled to approximately agarose beads. Affinity conjugation is carried out using metal and anti-GFP antibody pre-coated beads. This procedure was found to be easy and straightforward and also to provide a unique orientation of GFP-rhZP3 on the bead. By using the N-terminal poly-histidine tag or the GFP portion of GFP-rhZP3 as coating sites for affinity coating, the sperm-binding site of the rhZP3, which located on the C-terminal of rhZP3, was exposed to spermatozoa. In other preparations immuno-beads are prepared that rely on a layer of antibody that is specific for a protein such as GFP-rhZP3 that can bind spermatozoa. In an alternative step, GFP-rhZP3 was chemically coupled to beads. The purified GFP-rhZP3 glycoprotein was first dialyzed against conjugation buffer overnight with one buffer change. The GFP-rhZP3 was concentrated to a the final concentration above 1 mg/ml with Centricon 30. Then 0.4 mg EDC (1-ethyl-3-(3-dimethylaminopropyl)-carbodiimide) and 0.6mg NHS (N-hydroxysuccinimide ) were added to 1 ml of beads in conjugation buffer containing 40 μl of 5 μm beads or 20 μl of 0.2 μm beads. Beads were allowed to react for 15 minutes at room temperature. Beads were separated from the reaction solution with centrifuge. The activated beads were resuspended in 1 ml of concentrated GFP-rhZP3. The proteins were allowed to react for 2 hours at room temperature. Hydroxylamine was added to a final concentration of 10 mM to quench the reaction, which regenerate the original carboxyls). Coated beads were separated from thee reaction mixture with centrifugation and washed with conjugation buffer twice. The GFP-rhZP3 conjugated beads were re-suspended in Ham's F-10 containing 5% HSA and stored at 4° C. It was discovered that compared to affinity coating, particles made by chemical conjugation form a higher coating density. Moreover, chemical conjugation is seen to provide a stronger (covalent) bond between protein and beads. In order to expose the C terminal of rhZP3, the conjugation site is established between the carboxyl groups of beads and the amino group of GFP-rhZP3. The GFP-rhZP3 was advantageously found to provide more conjugate sites compared to the use of rhZP3 only.

Example 18

This example shows optimization of binding conditions of human spermatozoa to GFP-rhZP3 coated beads. A sperm binding assay was carried out as follows. An aliquot of semen (0.5 ml) was diluted with 1 ml of Ham's F-10 medium (Gibco) supplemented with 0.5% heat-inactivated human serum albumin (HSA). The sperm were centrifuged (5 minutes, 300×g), and then washed twice. The final pellet was overlaid with 0.5 ml of F-10 medium with HSA and incubated at 37° C., 5% $CO_2$ in air to achieve a separation of the motile sperm fraction. After 1 hour, motile spermatozoa were recovered and capacitated in 37° C., 5% $CO_2$ for 24 hours. One 100 µl droplet of the control sperm suspension (500,000 motile sperm/ml) was incubated with ZP3 coated bead/artificial zona in a Petri dish under oil for 3 hours. After co-incubation, each artificial zona was removed and pipetted five times to dislodge loosely attached sperm. The number of sperm tightly bound to the outer surface was counted. The number of artificial zona bound sperm is compared with the number of control sperm from the hemizona assay in a percentage manner to evaluate the sperm binding capability of artificial zona.

A hemizona assay is to be carried out as a parallel assay to evaluate the binding ability of GFP-rhZP3 coated agarose beads. An aliquot of semen (0.5 ml) is diluted with 1 ml of Ham's F-10 medium (Gibco) supplemented with 0.5% heat-inactivated human serum albumin (HSA). Sperm are centrifuged (5 minutes, 300×g), and then washed with Ham's F-10 twice. The final pellet is overlaid with 0.5 ml of F-10 medium with HSA and incubated at 37° C., 5% $CO_2$ in air to achieve a separation of the motile sperm fraction. After 1 hour, motile spermatozoa are recovered and capacitated in 37° C., 5% $CO_2$ for 24 hours. After capacitation, sperm sample are ready for use in a HZA. One 100 µl droplet of the control sperm suspension (500,000 motile sperm/ml) is placed in a Petri dish under oil. Spermatozoa and hemizona are incubated for 3 hours (37° C., 5% $CO_2$ in air). After co-incubation, each hemizona is removed and pipetted five times to dislodge loosely attached sperm (Hodgen et. al., 1988; Oehninger et al., 1991). The number of sperm tightly bound to the outer surface are counted. For each hemizona pair, the HZI is calculated as follows: (number of test sperm bound to the hemizona/number of fertile sperm bound to hemizona)×100 (Burkman, et al.,1988). The number of sperm bound on the hemizona from donor and patient sperm sample are used as controls to evaluate the sperm binding ability of artificial zona.

Example 19

This example illustrates unfolding/refolding of rhZP21rhZP3. Samples of rhZP2 and rhZP3 that were purified as described herein were dialyzed against 100 mM Tris/HCl buffer at pH 12. The unfolding of these proteins was further optimized by adding urea to a final concentration of 2M. Each protein solution was incubated at room temperature for 30 minutes. The pH of each protein solution was adjusted down to 8.5 by adding 1M HCl followed by extensive dialysis at 4° C. against the renaturation buffer (20 mM Tris buffer, pH 8.5 containing 1 mM EDTA, 1 mM reduced glutathione, 0.1 mM oxidized glutathione and 10% sucrose) overnight. (Patra et al., 2000)

Example 20

This example illustrates coating of rhZP2–rhZp3 fusion protein and of rhZP2–rhZP3 filament on beads. The purified rhZP2–rhZP3 fusion glycoproteins or rhZP2–rhZP3 filament were dialyzed against conjugation buffer overnight with one buffer change. Proteins were concentrated to a final concentration of above 1 mg/ml with a Centricon 30 concentrator. Then, 0.4 mg EDC (1-ethyl-3-(3-dimethylaminopropyl)-carbodiimide) and 0.6 mg NHS (N-hydroxysuccinimide ) were added to 1 ml of beads in conjugation buffer containing 40 µl of 5 µm beads or 20 µl of 0.2 µm beads. The mixtures were reacted for 15 minutes at room temperature. Beads were separated from the reaction solution with centrifuge. The activated beads were resuspended in 1 ml of concentrated rhZP2 and GFP-rhZP3. Proteins were allowed to react for 2 hours at room temperature. Hydroxylamine was added to a final concentration of 10 mM to quench the reaction (this method of quenching hydrolyzes any unreacted NHS present on the surface of beads and results in regeneration of the original carboxyls). The coated beads were separated with centrifugation and washed with conjugation buffer twice. The conjugated beads were resuspended in Ham's F-10 containing 5% HSA and stored at 4° C.

Example 21

This example shows the use of GFP-rhZP3 coated agarose beads to mediate sperm binding. Purified GFP-rhZP3 was immobilized on Nickel-NTA agarose beads (Qiagen, 100 µm in diameter) and used to replace zona in a sperm binding assay. The binding conditions of the hemizona assay were used for assay of bead binding to sperm.

Using these conditions, spermatozoa capacitated for 3 hours at 37° C. in the presence of 5% $CO_2$ were incubated with the GFP-rhZP3 coated beads for 30 minutes. Nickel-NTA beads alone or incubated with a pool of low GFP-rhZP3 activity was used as a negative control. After washing with a pipette up and down a few times, sperm bound to beads with and without ZGP-rhZP3 was calculated. The sperm bound to beads were clearly seen as black dots. The control beads that lacked the GFP-rhZP3 coating showed no black dots, as the Nickel-NTA beads revealed no specific binding with sperm. When incubated with GFP-rhZP3-Nickel-NTA, a specific binding between sperm and beads (black dots) was observed. However, different numbers of sperm were bound on each beads, which ranged from a few per bead to hundreds of sperm per bead.

Of course, changes and modifications to the embodiments presented herein are readily understood by the skilled artisan after reading this specification and furthermore, such changes and modifications may be practiced within the scope of the appended claims. Each patent, patent application and publication cited herein is incorporated by reference in its entirety.

REFERENCES

Aarons D, Boettger-Tong H, Holt G, Poirier G R. (1991) Acrosome reaction induced by immunoaggregation of a proteinase inhibitor bound to the murine sperm head. Mol Reprod Dev., 30, 258–64.

Arts E G, Kuiken J, Jager S. A new method to detect acrosome-reacted spermatozoa using biotinylated soybean trypsin inhibitor.Fertil Steril November 1994;62(5): 1044–55.

Austin, C. R. (1960) Capacitation and the release of hyaluronidase from spermatozoa. J. Reprod. Fertil., 3, 310–311.

Barratt, C. L. R. and Hornby, D. P. (1995) Induction of the acrosome reaction by rhuZP3. Human sperm acrosome reaction. Colloque INSERM, John Libey Eurotext, Paris, No. 236, 105–122.

Barratt, C. L. R., Whitmarsh, A., Homby, D. P., Clements, S., Cooke, I. D. and Moore, H. D. M. (1994).

Barros C, Crosby J A, Moreno R D, Early steps of sperm-egg interactions during mammalian fertilization; Cell Biol Int, January 1996; 20 (1): 33–9.

Beebe, S. J., Leyton, L., Burks, D., Ishikawa, M., Fuerst, T., Dean, J. and Saling, P. (1992) Recombinant mouse ZP3 inhibits sperm binding and induces the acrosome reaction. Dev. BioL, 151, 48–54.

Bercegeay S., Jean, M. and Barriere, P. (1995) Composition of human zona pellucida as revealed by SDS-PAGE after silver staining. Mol. Reprod. Dev., 41, 355–259.

Bielfeld P, Anderson R A, Mack S R, De Jonge C J, Zaneveld L J.. Are capacitation or calcium ion influx required for the human sperm acrosome reaction? Fertil Steril December 1994;62(6):1255–61.

Bleil J. D. and Wassarman P. M. (1980) Structure and function of the y zona pellucida: Identification and characterization of the mouse oocyte's zona pellucida. Dev. BioL, 76, 185–203.

Bleil J D, Wassarman P M. (1986) Autoradiographic visualization of the mouse egg's sperm receptor bound to sperm. J. Cell Biol.,102, 1363–71.

Bleil J D, Wassarman P M. (1988) Identification of a secondary sperm receptor in the mouse egg zona pellucida: role in maintenance of binding of acrosomereacted sperm to eggs. Dev. BioL,128, 376–85.

Bleil, J. D. and Wassarman, P. M. (1988) Galactose at the nonreducing terminus of O-linked oligosaccharides of mouse egg zona pellucida glycoprotein ZP3 is essential for the glycoprotein's sperm receptor activity. Proc. Nad. Acad. Sci. USA, 85, 6778–6782.

Bleil, J. D., and Wassarman, P. M. (1980) Mammalian sperm-egg interaction: identification of a glycoprotein in mouse egg zona pellucida possessing receptor activity for sperm. Cell, 20:3, 873–882.

Bleil, J. D., and Wassarman, P. M. (1983) Sperm-egg interactions in the mouse: sequence of events and induction of the acrosome reaction by a zona pellucida glycoprotein. Dev. Biol., 95, 317–324.

Brewis, I. A., Clayton, R. and Barratt, C. L. R. (1996) Characterization of the calcium influx and the acrosome reaction in human spermatozoa in response to recombinant ZP3. Mol. Human Reprod., 2, 583–589.

Burks, D. J., Carballada, R., Moore, H. D., and Saling, P. M. (1995) Interaction of a tyrosine kinase from human sperm with the zona pellucida at fertilization. Science, 269:5220 83–86.

Carver-Ward J A, Moran-Verbeek I M, Hollanders J M Comparative flow cytometric analysis of the human sperm acrosome reaction using CD46 antibody and lectins. J Assist Reprod Genet February 1997;14(2):111–9.

Chalfie, M. & Kain, S.; Eds. (1998) Green Fluorescent Protein: Properties, Applications, and Protocols (Wiley-Liss, New York)

Chamberlin M E, Dean J.(1990) Human homology of the mouse sperm receptor. Proc. Nad. Acad. Sci. USA, 87, 6014–6018.

Chamberlin, M. E. and Dean, J. (1990) Human homology of the mouse sperm receptor. Proc. Nad. Acad. Sci. USA, 87, 6014–6018.

Chapman, N. R. and Barratt, C. L. R. (1996) The role of carbohydrates in spermatozoa-zona pellucida adhesion. Mol. Human Reprod., 2, 767–774.

Chapman, N. R. and Barratt, C. L. R. (1997) Sperm-zona interaction and recombinant DNA technology. Mol. Human Reprod., 3, 646–650.

Cheng F P, Fazeli A, Voorhout W F, Marks A, Bevers M M, Colenbrander B. Use of peanut agglutinin to assess the acrosomal status and the zona pellucida-induced AR in stallion spermatozoa. J Androl November–December 1996;17(6):674–82.

Chuang A T, Howards S S; Male infertility, Evaluation and nonsurgical therapy, Urologic Clinics of North America, 1998, vol 25, no 4, 703–13.

Clark, G. F., Oehninger, S., and Seppala, M. (1996) Role for glycoconjugates in cellular communication in the human reproduction system. Mol. Hum. Reprod., 2, 513–517.

Clark, G. F., Patankar, M. S., Hinsch, K. D. and Oehninger, S. (1995) New concepts in human sperm-zona pellucida interaction. Hum. Repro., 10(Suppl. 1), 31–37.

Cross, N. L., Morales, P., Overstreet, J. W. and Hanson, F. W. (1988) Induction of acrosome reactions by the human zona pellucida. Biol Reprod 38:1 235–44.

Dean J. (1992) Biology of mammalian fertilization: role of the zona pellucida. J Clin Invest. 89, 1055–9.

Dell, A., Morris, H. R., Easton, R. L. (1995) Structural analysis of the oligosaccharides derived from glycodelin, a human glycoprotein with potent immunosuppressive and contraceptive activities. J. Biol. Chem., 270, 2411624126.

Dong K W, Chi T F, Juan Y W, Chen C W, Lin Z, Xiang X Q, Mahony M, Gibbons W E, Oehninger S. Characterization of the biological activities of recombinant human zona pellucida protein 3 expressed in human ovarian teratocarcinoma (PA-1) cells. Am J Obstet Gynecol 184: 835–44; 2001.

Dong, K. W., Chi, T. F., Juan, Y. W., Chen, C. W., Lin, Z., Xiang, X. Q., Mahony, M., Gibbons, W. E., Oehninger, S. (2001) Characterization of the biologic activities of recombinant human zona pellucida protein 3 expressed in human ovarian teratocarcinoma (PA-1) cells. Am. 1. Obstet. GynecoL, 184, 83 5–844.

Dunbar, B. S., Avery, S., Lee, V., Prasad, S., Schwalm, D., Schwoebel, E., Skinner, S., and Wilkins, B. (1994) The mammalian zona pellucida: its biochemistry, immunochemistry, molecular biology, and developmental expression. Reprod Fertil Dev, 6:3 331–347.

Dunbar, B. S., Liu, C., and Sammons, D. W. (1981) Identification of the three major proteins of porcine and rabbit zona pellucida by high resolution two dimensional gel electrophoresis: comparison with serum, follicular fluid, and ovarian cell proteins. Bio Reprod, 24:5 1111–1124.

Esterhuizen A D, Franken D R, Lourens J G H, van Rooyen L H; Clinical importance of zona pellucida induced acrosome reaction and its predictive value for IVF. Hum Reprod;16(1):138–44, 2001.

Ficsor G, Ginsberg L C, Oldford G M, Snoke R E, Becker R W; Gelatin-substrate film technique for detection of acrosin in single mammalian sperm; Fertil Steril 39:548–52, 1983.

Flach, J., Bossie, M., Vogel, J., Corbett, A., Jinks, T., Willins, D. A. & Silver, P. A. (1994) A yeast RNA-binding protein shuttles between the nucleus and the cytoplasm. Mol. Cell. Biol. 14:8399–8407.

Florman, H. M. and Wassarman, P. M. (1985) O-linked oligosaccharides of mouse egg ZP3 account for its sperm receptor activity. Cell, 41, 313–324.

Franken D R, Bastiaan H S, Kidson A, Wranz P, Habenicht U F; Zona pellucida mediated acrosome reaction and sperm morphology. Andrologia; 29:3117; 1997.

Fukuda, M. N., Dell, A., Oates, J. E. and Fukuda, M. (1985) Embryonal lactosaminoglycan. The structure of branched lactosaminoglycans with novel disialosyl (sialyl alpha 29 sialyl) terminals isolated from PA I human embryonal carcinoma cells. J Biol. Chem., 260, 6623–6631.

Furukawa, T., Ozawa, M., Huang, R. P. and Muramatsu, T. (1990) A heparin binding protein whose expression increases during differentiation of embryonal carcinoma cells to parietal endoderm cells: cDNA cloning and sequence analysis. J. Biochem. (Tokyo), 108: 297–302.

Gibbons W E, Oehninger S. Characterization of the biological activities of recombinant human zona pellucida protein 3 expressed in human ovarian teratocarcinoma (PA-1)cells. Am J Obstet Gynecol 184:835–44;2001 Glycosylation of human recombinant ZP3 is necessary to induce the human acrosome reaction. [Abstr. No. 033] Hum. Reprod., 9 (Suppl.).

Hartmann, J. F., Gwatkin, R. B. and Hutchison, C. F. (1972) Early contact interactions between mammalian gametes in vitro: evidence that vitellus influences adherence between sperm and zona pellucida. Proc. Natl. Acad Sci. USA, 69, 2767–2769.

Henkel R, Franken D R, Habenicht U F, Zona pellucida as physiological trigger for the induction of AR. Andrologia August–September 1998;30(45):275–80.

Henkel R, Muller C, Miska W, Schill W B, Kleinstein J, Gips H. Acrosin activity of human spermatozoa by means of a simple gelatinolytic technique: a method useful for IVF. J Androl 16(3):272–7, 1995.

Hook E. B. Rate of chromosomal abnormalities at different maternal ages, (1981) Obstet Gynecol 58: 282.

Hyne, R N., Higginson, R., Kohhnan, D. and Lopata, A. (1984) Sodium requirement for capacitation membrane fusion during the guinea pig acrosome reaction. J. Reprod FertiL, 70, 83–94.

Inouye, S. & Tsuji, F. 1. (1994b) Evidence for redox forms of the Aequorea green fluorescent protein. FEBS Letters 351:211–214.

Jaiswal B S, Eisenbach M, Tur-Kaspa I; Detection of partial and complete AR in human spermatozoa: which inducers and probes to use? Mol Hum. Reprod 1999; vo15 no.3 214–9.

Jones R (1990) Identification and functions of mammalian sperm egg recognition molecules during fertilization. J. Reprod FertiL, 42, 89–105.

Kennedy W P, Kaminski J M, Van der Ven H H, Jeyendran R S, Reid D S, Blackwell J, Bielfeld P, Zaneveld L J. A simple, clinical assay to evaluate the acrosin activity of human spermatozoa. J Androl May–June 1989;10(3): 221–31.

Kinloch, R. A., Ruiz-Seiler, B. and Wassarman, P. M. (1991) Genomic organization and polypeptide primary structure of zona pellucida glycoprotein hZP3, the hamster sperm receptor. Dev. Biol., 145, 203–204.

Kinloch, R. A., Ruiz-Seiler, B., and Wassarman, P. M. (1990) Genomic organization and polypeptide primary structure of zona pellucida glycoprotein hZP3, the hamster sperm receptor [published erratum appears in Dev Biol May 1991; 145(1): 203]. Dev. Biol. 142:2, 414–421.

Koehler, J. K. (1981) Surface alterations during the capacitation of mammalian spermatozoa. Am. J. PrimatoL, 1, 131–141.

Kohn F M, Mack S R, Schill W B, Zaneveld L J. Detection of human sperm AR: comparison between methods using double staining, Pisum sativum agglutinin, concanavalin A and transmission electron microscopy Hum Reprod 1997 April; 12(4):714–21.

Lee M A, Trucco G S, Bechtol K B, Wummer N, Kopf G S, Blasco L, Storey B T; Capacitation and acrosome reactions in human spermatozoa monitored by a chlortetracycline assay. Fertil Steril 48:649–58,1987.

Lee, V. H., Schwoebel, E., Prasad, S., Cheung, P., Timmons, T. M., Cook, R., and Dunbar, B. S. (1993) Identification and structural characterization of the 75-kDa rabbit zona pellucida protein. JBiol Chem 268:17 12412–12417.

Leyton, L. and Saling, P. (1989) Evidence that aggregation of mouse sperm receptors by ZP3 triggers the acrosome reaction. J. Cell BioL, 108, 2163–2168.

Liang, L., Chamow, S. M. and Dean, J. (1990) Oocyte-specific expression of mouse ZP-2: Developmental regulation of the zona pellucida genes. Mol. Cell. BioL, 10, 1507–1515.

Liang, L. F., and Dean, J. (1993) Conservation of mammalian secondary sperm receptor genes enables the promoter of the human gene to function in mouse oocytes. Dev Biol 156:2 399–408.

Liu D Y, Baker H W, A simple method for assessment of the human AR of spermatozoa bound to the zona pellucida: lack of relationship with ionophore A23187-induced AR. Hum Reprod 11(3) 551–7, 1996.

Macek, M. B., Lopez, L. C., Shur, B. D. (1991) Aggregation of beta-1,4galactosyltransferase on mouse sperm induces the acrosome reaction. Dev Biol., 147, 440–4.

Macek, M. B., Shur, B. D. (1988) Protein-carbohydrate complementary in mammalian gamete recognition. Gamete Res. 20:1, 93–109.

Mack S, Bhattacharyya A K, Joyce C, van der Ven H, Zaneveld L J, Acrosomal enzymes of human spermatozoa before and after in vitro capacitation.; Biol Reprod 1983 June; 28(5): 1032–42.

Mackenna A; Int J Androl 1995 June; 18 Suppl 1:58–61.

Margalit I, Rubinstein S, Breitbart H, A novel method for evaluating the acrosomal status of mammalian spermatozoa. Arch Androl 39: 87–99, 1997.

Marshall, J., Molloy, R., Moss, G. W. J., Howe, J. R. & Hughes, T. E. (1995) The jellyfish green fluorescent protein: a new tool for studying ion channel expression and function. Neuron 14:211–215.

Mcllhinney, R. A. J. and Patel, S. (1983) Characterization of the fibronectin synthesized by human germ cell tumors. Cancer Research, 43, 1282–1288.

Menken J. Trussell J. and Larsen 1. J. (1985) Age and infertility Science 233: 1389.

Morris, H. R., Dell, A., Easton, R. ., Panico, M., Koistinen, H., Koistinen, R., Oehninger, S., Patankar, M. S., Seppala, M., Clark, G. F. (1996) Genderspecific glycosylation of human glycodelin affects its contraceptive activity. J. Biol. Chem. 271:50, 32159–67.

Mortillo, S. and Wassarman, P. M. (1991) Differential binding of gold-labeled zona pellucida glycoproteins mZP2 and mZP3 to mouse sperm membrane components. Development, 113,141–149.

Oehninger, S., Acosta, A. A., and Hodgen, G. D. (1990) Antagonistic and agonistic properties of saccharide moieties in the hemizona assay. Fertil. Steril., 55, 165–169.

Oehninger, S., Acosta, A. A., Veeck, L. L., Brzyski, R., Kruger, T. F., Muasher, S. J., and Hodgen, G. D. (1991) Recurrent failure of in vitro fertilization: Role of the hemizona assay in the sequential diagnosis of specific sperm-oocyte defects. Am. J. Obstet. Gynecol., 164, 1210–1215.

Oehninger, S., Coddington, C. C., Hodgen, G. D., and Seppala, M. (1995) Factors affecting fertilization: endometrial placental protein 14 reduces the capacity of human spermatozoa to bind to the human zona pellucida. Fertil. Steril., 63, 377–383.

Oehninger, S., Franken, D., and Kruger, T. (1997) Approaching the next millennium: how should we manage andrology diagnosis in the intracytoplasmic sperm injection era? Fertil Steril, 67, 434–6.

Oehninger, S., Patankar, M., Seppala, M. and Clark, G. F. (1998) Involvement of selectin-like carbohydrate binding specificity in human gamete interaction. Andrologia, 30, 269–274.

Oehninger, S., Smith, E. K. and Stoughton, K. (1992) England diagnostic significance of sperm-zona interaction. In Reproductive Medicine Review., 1, 57–81.

Oehninger, S., Stecker, J. F., and Acosta, A-A. (1992) Male infertility: the impact of assisted reproductive technologies. Curr Opin Obstet Gynecol, 4, 185–96.

O'Farrell, P. H. (1975) High resolution two-dimensional electrophoresis of proteins. J. Biol Chem., 250, 4007–4021.

Ozgur, K., Patankar, M., Oehninger, S. and Clark, G. F. (1998) Direct evidence for the involvement of carbohydrate sequences in human sperm-zona pellucida binding. Mol. Hum. Reprod., 4, 318–324.

Patankar, M. S., Oehninger, S. and Barnett, T. et al. (1993) A revised structure for fucoiddin may explain some of its biological activities. J. Biol. Chem., 268, 21770–21776.

Patankar, M. S., Ozgur, K., Oehninger, S., Dell, A., Morris, H., Seppala, M. and Clark, G. F. (1997) Expression of glycans linked to natural killer cell inhibition on the human zona pellucida. Mol. Hum. Reprod., 3, 501–505.

Patra, A. K., Gahlay, G. K., Reddy, B. V., Gupta, S. K., and Panda, A. K. (2000) Refolding, structural transition and spermatozoa-binding of recombinant bonnet monkey (Macaca radiata) zona pellucida glycoprotein-C expressed in *Escherichia coli*. Eur J Biochem., 267, 7075–81.

Perry R L, Naeeni M, Barratt C L, Warren M A, Cooke I D. A time course study of capacitation and the acrosome reaction in human spermatozoa using a revised chlortetracycline pattern classification. Fertil Steril 1995 July; 64(1):150–9.

Pietrobon E O, Dominguez L A, Vincenti A E, Burgos M H, Fornes M W; Detection of the mouse AR by acid phosphatase. Comparison with chlortetracycline and electron microscopy. J Androl January–February 2001; 22(1):96–103.

Prasad, S. V., Wilkins, B., Skinner, S. M. and Dunbar, B. S. (1996) Evaluating zona pellucida structure and function using antibodies to rabbit 55 kDa ZP protein expressed in baculovirus expression system. Mol. Reprod. Dev., 43, 519–529.

Prasher, D. C., Eckenrode, V. K., Ward, W. W., Prendergast, F. G. & Cormier, M. J. (1992) Primary structure of the Aequorea victoria green fluorescent protein. Gene 111: 229–233.

Ringuette, M. J., Sobieski, D. A., Chamow, S. M., and Dean, J. (1986) Oocytespecific gene expression: molecular characterization of a cDNA coding for ZP3, the sperm receptor of the mouse zona pellucida. Proc Natl Acad Sci USA, 83:12 4341–4345.

Russell L, Peterson R N, Freund M; Morphologic characteristics of the chemically induced AR in human spermatozoa. Fertil Steril, 1979 July; 32(1):87–92.

Saling, P. M. (1989) Mammalian sperm interaction with extracellular matrices of the egg. Oxf Rev Reprod Biol, 11, 339–388.

Saling, P. M. (1991) How the egg regulates sperm function during gamete interaction: facts and fantasies. Biol Reprod, 44: 246–251.

Saling, P. M., Sowinski, J. and Storey, B. T. (1979) An ultrastructural study of epididymal mouse spermatozoa binding to zona pellucida in vitro: sequential relationship to the acrosome reaction. J. Exp. Zool., 209, 229–238.

Salzberger Z, Lewin L M, Shalgi R. Loss of acid phosphatase from rat spermatozoa as a method for assessing the acrosome reaction. Andrologia 24:155–9, 1992.

Schwoebel, E., Prasad, S., Timmons, T. M., Cook, R., Kimura, H., Niu, E. M., Cheung, P., Skinner, S., Avery, S. E., Wilkins, B., et al (1991) Isolation and characterization of a full-length cDNA encoding the 55-kDa rabbit zona pellucida protein. J. Biol. Chem., 266:11, 7214–7219.

Shalgi R, Raz T. (1997) The role of carbohydrate residues in mammalian fertilization. Histod Histopathol, 12, 813–22

Steams, T. (1995) The green revolution. Curr. Biol. 5:262–264.

Tesarik J, ESHRE Workshop on advanced diagnostic andrology, Hum Reprod vol. 11 no.7:1463–79, 1996.

Tesarik J, ESHRE Workshop on advanced diagnostic andrology, Hum Reprod vol.II no.7:1463–79, 1996.

Thillai-Koothan, P., van Duin, M., and Aitken, R. J. (1993) Cloning, sequencing and oocyte-specific expression of the marmoset sperm receptor protein, ZP3. Zygote 1:2 93–101.

Timmons, T. M., Maresh, G. A., Bundman, D. S., Dunbar, B. S. (1987) Use of specific monoclonal and polyclonal antibodies to define distinct antigens of the porcine zonae pellucidae. Biol. Reprod. 36:5 1275–87.

Toner J. P. and Flood J. T. (1993) Fertility after the ago of 40 Obstet Gynecol N Amer 20:261.

Topfer-Petersen E, Cechova D, Henschen A, Steinberger M, Friess A E, Zucker A, Cell biology of acrosomal proteins; Andrologia 1990;22 Suppl 1:110–2.

Tsubamoto H, Hasegawa A, Nakata Y, Naito S, Yamasaki N, Koyama K. (1999) Expression of recombinant human zona pellucida protein 2 and its binding capacity to spermatozoa. Biol. Reprod.,61, 1649–54.

Van Duin, M., Polman, J., De Breet, T. M., Ginneken, K. V., Bunschoten, H., Grootenhuis, A., Brindle, J. and Aitken, J. (1994) Recombinant human zona pellucida protein ZP3 produced by Chinese hamster ovary cells induces the human sperm acrosome reaction and promotes sperm-egg fusion. Biol. Reprod., 51, 670–617.

Varki, A. (1993) Biological roles of oligosaccharides: all of the theories are correct. Glycobiology, 3, 97–130.

Varki, A. (1993) Biological roles of oligosaccharides: all of the theories are correct. Glycobiology, 3, 97–130.

Wang, S. & Hazelrigg, T. (1994) Implications for bed mRNA localization from spatial distribution of exu protein in Drosophila oogenesis. Nature 369:400–40.

Ward C R, Storey BTDetermination of the time course of capacitation in mouse spermatozoa using chlortetracycline fluorescence assay. Dev Biol 1984 August; 104(2): 287–96.

Wassarman, P. M. (1988) Zona pellucida glycoproteins. Ann. Rev. Biochem., 57, 5–442.

Wassarman, P. M. (1990 a) Profile of a mammalian sperm receptor. Development, 108, 1–17.

Wassarman, P. M. (1990 b) Regulation of mammalian fertilization by zona pellucida glycoproteins. J Reprod. Fertil. Suppl, 42, 79–87.

Wassarman, P. M. and Litscher, E. S. (1995) Sperm-egg recognition mechanisms in mammals. Current Topics in Dev. Biol., 30, 1–19.

Wassarman, P. M. and Mortillo, S. (1991) Structure of the mouse egg extracellular coat, the zona pellucida. Int. Rev. CytoL, 130, 85–110.

Whitmarsh, A. J., Woolnough, M. J., Moore, H. D. M. (1996) Biological activity of recombinant human ZP3 produced in vitro: potential for a sperm function test. Mol. Human Reprod., 2, 911–919.

Yanagimachi, R., Okada, A., Tung, K. S. (1981) Sperm autoantigens and fertilization: II. Effects of anti-guinea pig sperm autoantibodies on spermovum interactions. Biol Reprod., 24, 512–8.

Yurewicz, E. C., Pack, B. A., Armant, D. R., and Sacco, A. G. (1993) Porcine zona pellucida ZP3 alpha glycoprotein mediates binding of the biotin-labeled M(r) 55,000 family (ZP3) to boar sperm membrane vesicles. Mol. Reprod. Dev., 36:3, 382–389.

We claim:

1. A reagent for testing male infertility, comprising a recombinantly produced glycosylated human sperm binding zona pellucida protein or peptide complexed to a detection agent, wherein the protein or peptide is selected from the group consisting of a protein consisting of the amino acid sequence of SEQ ID NO: 1, a peptide consisting of amino acid residues 308 to 348 of SEQ ID NO: 1, a peptide consisting of amino acid residues 200 to 351 of SEQ ID NO: 1, a peptide consisting of amino acid residues 14 to 351 of SEQ ID NO: 1.

2. A reagent for testing male infertility, comprising a recombinantly produced glycosylated human sperm binding zona pellucida protein complexed to a detection agent, wherein the protein is fusion protein comprising ZP2 and a protein or peptide selected from the group consisting of a protein consisting of the amino acid sequence of SEQ ID NO: 1, a peptide consisting of amino acid residues 308 to 348 of SEQ ID NO: 1, a peptide consisting of amino acid residues 200 to 351 of SEQ ID NO: 1, a peptide consisting of amino acid residues 14 to 351 of SEQ ID NO: 1.

3. A reagent for testing male infertility, comprising a recombinantly produced glycosylated human sperm binding zona pellucida protein complexed to a detection agent, wherein the protein is a protein complex comprising ZP2 and a protein or peptide selected from the group consisting of a protein consisting of the amino acid sequence of SEQ ID NO: 1, a peptide consisting of amino acid residues 308 to 348 of SEQ ID NO: 1, a peptide consisting of amino acid residues 200 to 351 of SEQ ID NO: 1, a peptide consisting of amino acid residues 14 to 351 of SEQ ID NO: 1.

4. A reagent as described in claim 1, 2 or 3, wherein the detection agent is selected from the group consisting of: green fluorescence protein, a fluor, an enzyme, beta galactosidase, alkaline phosphatase, horseradish peroxidase, an antigenic peptide, Alexa488, fluorophore-green fluorescence protein conjugate, a peptide that comprises hemagglutinin, a peptide that comprises V5, a peptide that comprises Myc, and biotin.

5. A reagent as described in claim 1, 2 or 3, wherein the glycosylated sperm binding zona pellucida protein or peptide is prepared by culture of a human ovarian cell line, uterogenital origin cell line or a mammary cell line.

6. A reagent as described in claim 5, wherein the cell line is PA-1 cells.

7. A reagent as described in claim 1, 2 or 3, wherein the protein or peptide comprises recombinantly produced ZP2 capable of forming a ZP2/ZP3 protein complex upon incubation with ZP3.

8. A reagent as described in claim 1, 2 or 3, wherein the protein or peptide comprises ZP2/ZP3 protein complex capable of binding specifically to human sperm, wherein said ZP2 and ZP3 proteins are recombinantly produced from a heterologous gene in a host cell.

9. A reagent as described in claim 8, wherein the molar ratio of ZP3 to ZP2 is equal to or greater than 1.

10. A reagent as described in claim 1, 2 or 3, further comprising human ZP2.

11. A reagent as described in claim 1, 2 or 3, wherein the protein or peptide comprises purified human ZP2/ZP3 protein complex, wherein said ZP2 and ZP3 proteins are recombinantly produced from a heterologous gene in a host cell.

12. A kit for testing male infertility, comprising the reagent of claim 1, 2 or 3, and at least a buffer salt or salt solution.

13. A reagent as described in claim 1, 2 or 3, wherein the glycosylated sperm binding zona pellucida protein or peptide is prepared by culture of human embryonic kidney 293 cells.

14. A method for detecting infertility of a male, comprising the step of contacting the reagent of claim 1, 2 or 3, with a sperm sample of the male and detecting said reagent bound to sperm.

15. A method for detecting infertility of a male, comprising: a) providing a reagent as described in claim 1, 2 or 3; b) contacting a sperm sample of the male with the reagent for a period of time sufficient to allow binding between the glycopeptide and the sperm; and c) detecting the detection agent bound to sperm.

16. A method as described in claim 15, wherein the detection agent is an antigen, and detection step c) comprises incubating with a fluorescence labeled antibody to generate a fluorescence signal associated with bound detection agent.

17. A method as described in claim 16, wherein the fluorescence labeled antibody is Alexa 488 or an antibody coupled to a dye that recognizes an antigenic site on the reagent.

18. A method as described in claim 14, wherein the reagent is ZP3/GFP.

19. A method as described in claim 15, further comprising the step of washing the contacted sperm sample of step b) before step c).

* * * * *